(12) United States Patent
Mertens et al.

(10) Patent No.: US 10,941,207 B2
(45) Date of Patent: Mar. 9, 2021

(54) FUSION PROTEIN COMPRISING THREE BINDING DOMAINS TO 5T4 AND CD3

(71) Applicant: BIOTECNOL LIMITED, Hertfordshire (GB)

(72) Inventors: Nico Mertens, Melsele (BE); Philip Jeffrey Cunnah, Cascais (PT); Ana Rita Da Fonseca Ricardo, Cascais (PT)

(73) Assignee: CHIOME BIOSCIENCE, INC, Tokyo (JP)

( * ) Notice: Subject to any disclaimer, the term of this patent is extended or adjusted under 35 U.S.C. 154(b) by 486 days.

(21) Appl. No.: 15/536,121

(22) PCT Filed: Dec. 21, 2015

(86) PCT No.: PCT/EP2015/080795
§ 371 (c)(1),
(2) Date: Jun. 14, 2017

(87) PCT Pub. No.: WO2016/097408
PCT Pub. Date: Jun. 23, 2016

(65) Prior Publication Data
US 2017/0342160 A1    Nov. 30, 2017

(30) Foreign Application Priority Data
Dec. 19, 2014    (EP) .................................... 14199493

(51) Int. Cl.
*C07K 16/00*    (2006.01)
*C07K 16/30*    (2006.01)
*C07K 16/28*    (2006.01)
*A61K 39/00*    (2006.01)

(52) U.S. Cl.
CPC .......... *C07K 16/30* (2013.01); *C07K 16/2809* (2013.01); *A61K 2039/505* (2013.01); *C07K 2317/24* (2013.01); *C07K 2317/31* (2013.01); *C07K 2317/522* (2013.01); *C07K 2317/55* (2013.01); *C07K 2317/56* (2013.01); *C07K 2317/622* (2013.01); *C07K 2317/624* (2013.01); *C07K 2317/64* (2013.01); *C07K 2317/92* (2013.01); *C07K 2317/94* (2013.01)

(58) Field of Classification Search
None
See application file for complete search history.

(56) References Cited

FOREIGN PATENT DOCUMENTS

| CN | 101490085 A | 7/2009 |
| WO | WO 91/09967 A1 | 7/1991 |
| WO | 2013/041687 A1 | 3/2013 |
| WO | 2013/163427 A1 | 10/2013 |

OTHER PUBLICATIONS

Almagro & Fransson, Frontiers in Bioscience 2008; 13:1619-33 (Year: 2008).*
De Genst et al., Dev Comp Immunol 2006; 30:187-98 (Year: 2006).*
Yoshinaga et al., J. Biochem 2008; 143:593-601 (Year: 2008).*
Mertens, Nico, "Tribodies: Fab-scFv Fusion Proteins as a Platform to Create Multi-functional Pharmaceuticals," Bispecific Antibodies, Chapter 8, (ed. R. Kontermann), SpringerLink, pp. 135-149 (Jul. 1, 2011).
PCT International Search Report of PCT/EP2015/080795 dated Apr. 8, 2016.
PCT Written Opinion of PCT/EP2015/080795 dated Apr. 8, 2016.
Burks et al., "In vitro scanning saturation mutagenesis of an antibody binding pocket", Proc. Natl. Acad. Sci., 1997, 94:412-417.
Chen et al., "In vitro scanning saturation mutagenesis of all the specificity determining residues in an antibody binding site", Protein Engineering, 1999, 12(4): 349-356.
Forsberg et al., "Identification of Framework Residues in a Secreted Recombinant Antibody Fragment That Control Production Level and Localization in *Escherichia coli*", The Journal of Biological Chemistry, Issue of May 9, 1997, 272(19): 12430-12436.

* cited by examiner

*Primary Examiner* — Meera Natarajan
(74) *Attorney, Agent, or Firm* — James S. Keddie; Bozicevic, Field & Francis LLP

(57) ABSTRACT

The present invention relates to a bispecific binding molecule comprising three binding domains, wherein a first and/or a second binding domain are capable of binding to the extracellular 5T4 antigen and the remaining binding domain(s) is (are) capable of binding to the CD3 receptor complex on T cells. Moreover, the invention relates to a nucleic acid sequence encoding fusion protein, a vector comprising said nucleic acid sequence and a host cell transformed or transfected with said vector. Furthermore, the invention relates to a process for the production of the fusion protein of the invention, a medical use of said fusion protein and a kit comprising said fusion protein.

7 Claims, 26 Drawing Sheets
Specification includes a Sequence Listing.

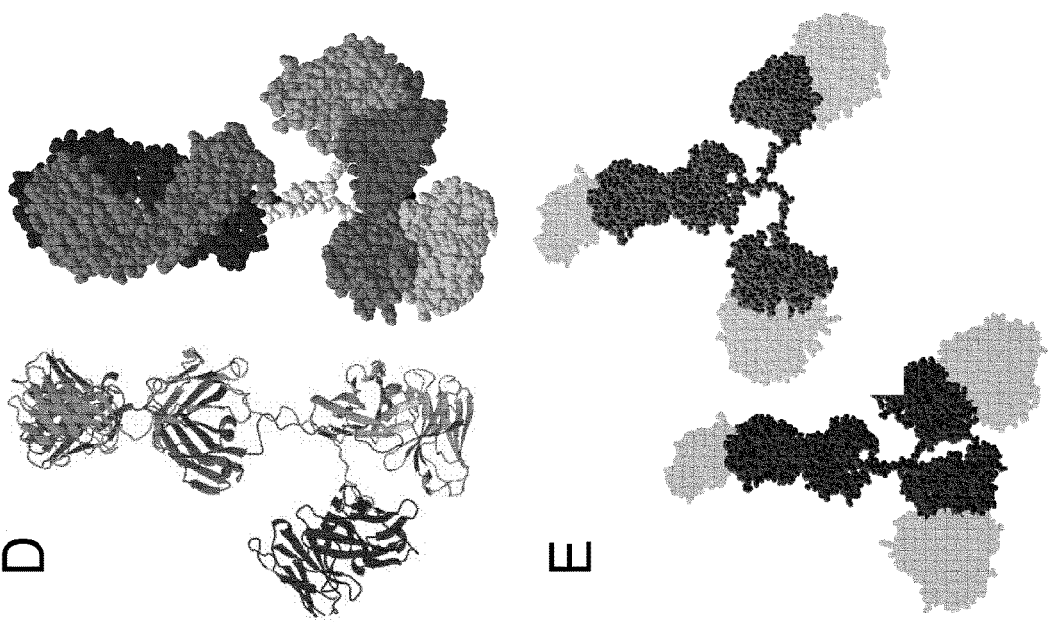
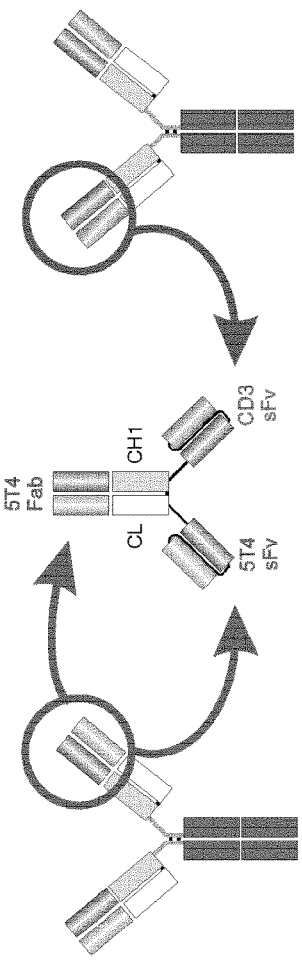
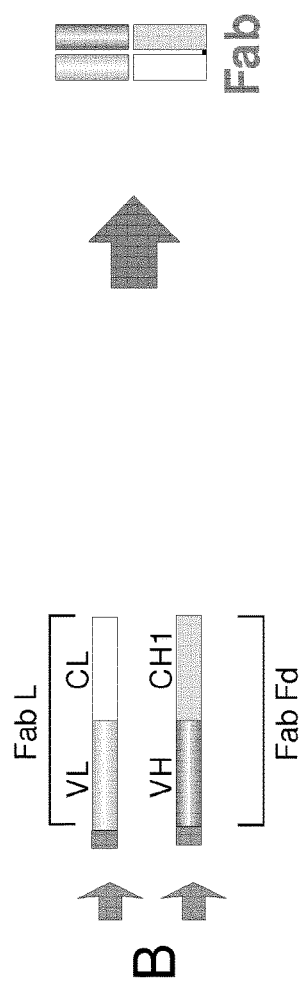
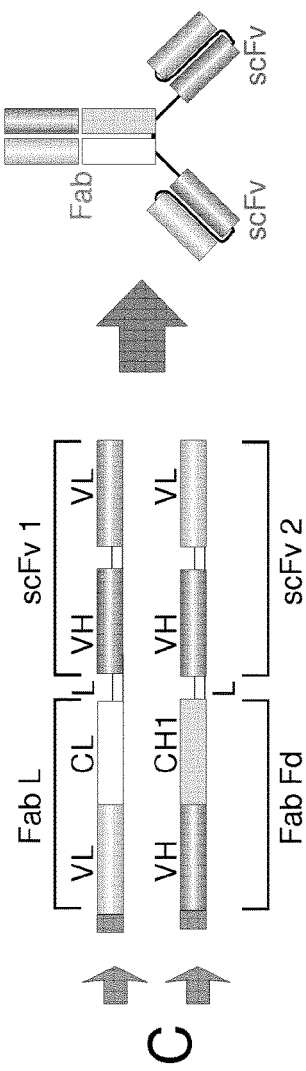
FIG 1A

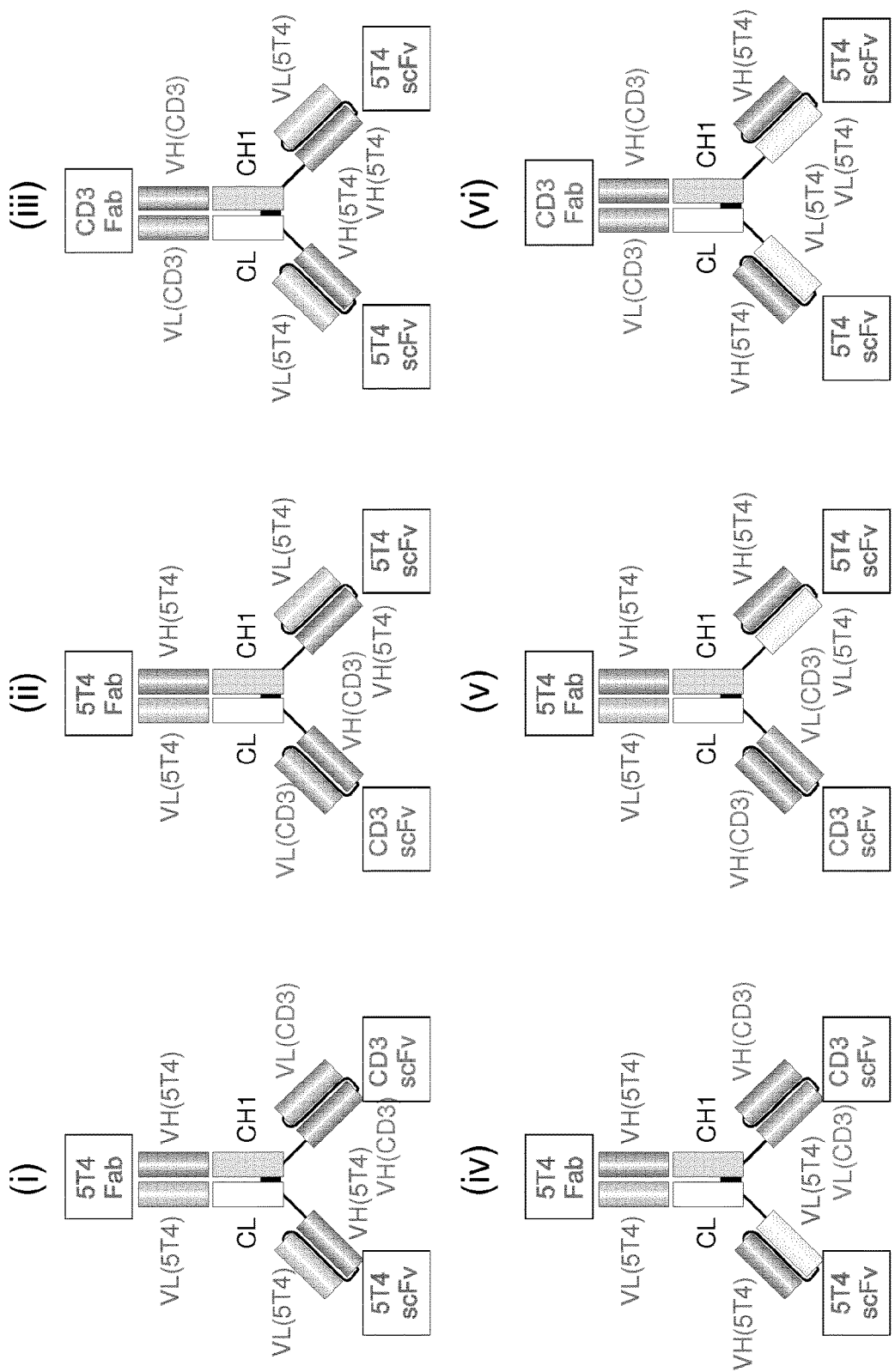

FIG 3
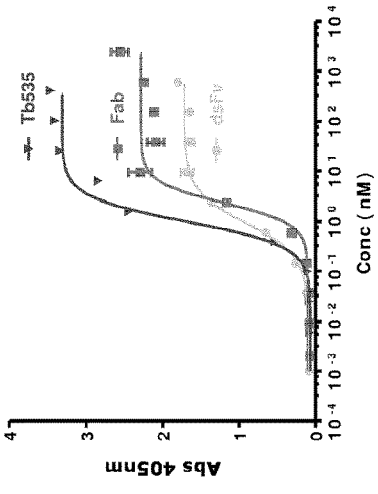
A. Tribody as a Fab-(dsFv)₂ fusion protein Tb535
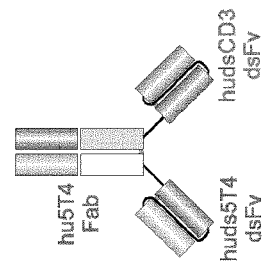
B. $K_D$ comparison of components and other formats (BiTE / IgG)
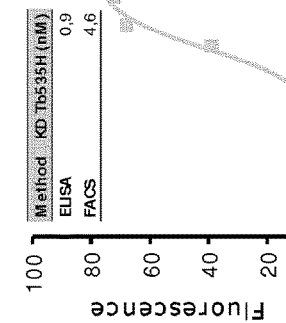
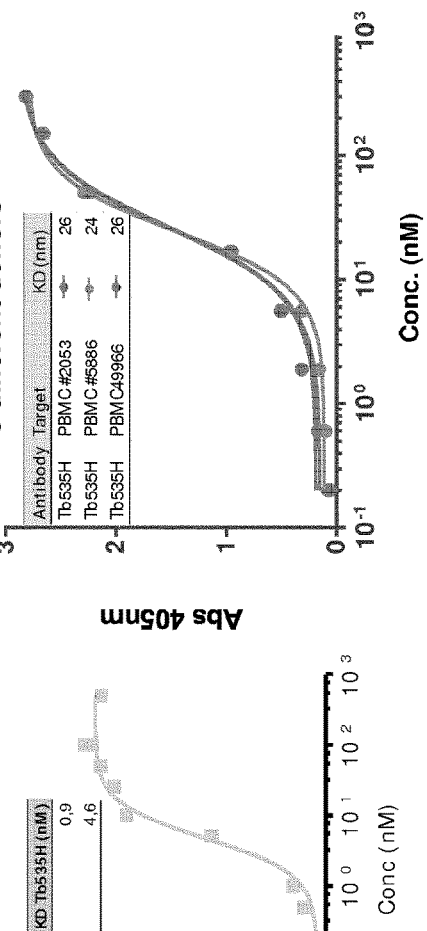
C. ELISA on 5T4 protein
E. FACS Titration on 5T4+ cells (MSTO-211H)
F. Tb535 binding to PBMC: 3 different donors
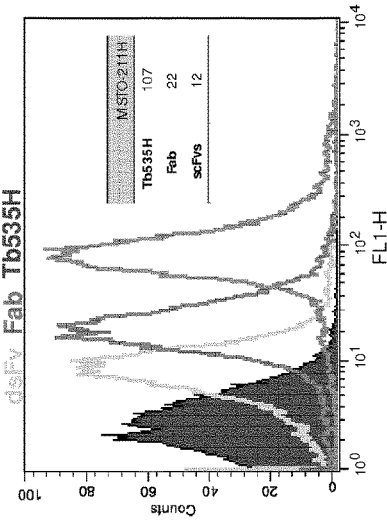
D. FACS Decoration on 5T4+ cells (MSTO-211H)

FIG 4A

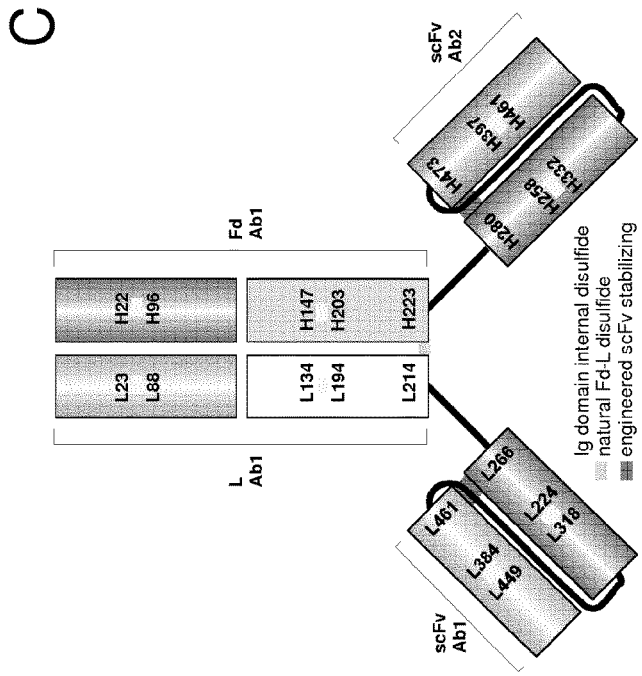

>H
QVQLVQSGAEVKKPGASVKVSCKASGYSFTSYYMHWVKQSPGQGLEWIGR
INPNNGVTLYNQKFKDRVTMTRDTSISTAYMELSRLRSDDTAVYYCARST
MITNYVMDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQT
YICNVNHKPSNTKVDKKVEPKSCDKTHTGPGGSPGQVQLVQSGAELKKP
GASVKVSCKASGYTFIRYTMHWVRQAPGQCLEWMGYINPSRGYTNYNQKF
KDKATLTADKSTSTAYMELRSLRSDDTAVYYCARYDDHYSLDYWGQGTL
VTVSSASGGGGSGGGGSGGGGSAGDIQLTQSPSILSASVGDRVTITCRAS
SSVSYMNWYQQKPGKAPKRWIYDTSKVAGVPYRFSGSGSGTEYTLTISS
MQPEDFATYYCQQWSSNPLTFGQGTKVEIKSG

>L
DIVMTQSPDSLAVSLGERATINCKASQSVSNDVAWYQQKPGQPPKLLIYY
TSSRYAGVPDRPSGSGSGTDFTLTISSLQAEDVAVYYCQQDYNSPPTFGG
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGECGPGGGSPGQVQLVQSGAEVKKPGASVKVSCKASGYS
FTSYYMHWVKQSPGQCLEWIGRINPNNGVTLYNQKFKDRVTMTRDTSIST
AYMELSRLRSDDTAVYYCARSTMITNYVMDYWGQGTLVTVSSASGGGGSG
GGGSGGGGSAGDIVMTQSPDSLAVSLGERATINCKASQSVSNDVAWYQQK
PGQPPKLLIYYTSSRYAGVPDRFSGSGSGTDFTLTISSLQAEDVAVYYCQ
QDYNSPPTFGCGTKLEIKSG

Disulfide-isoforms (BOLT-SDS-PAGE)

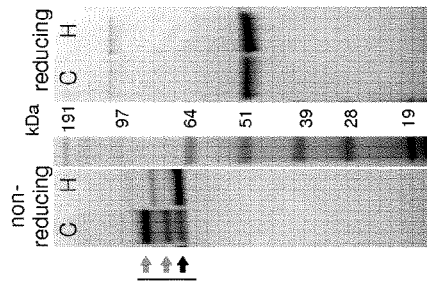

C: Tb535C H: Tb535H

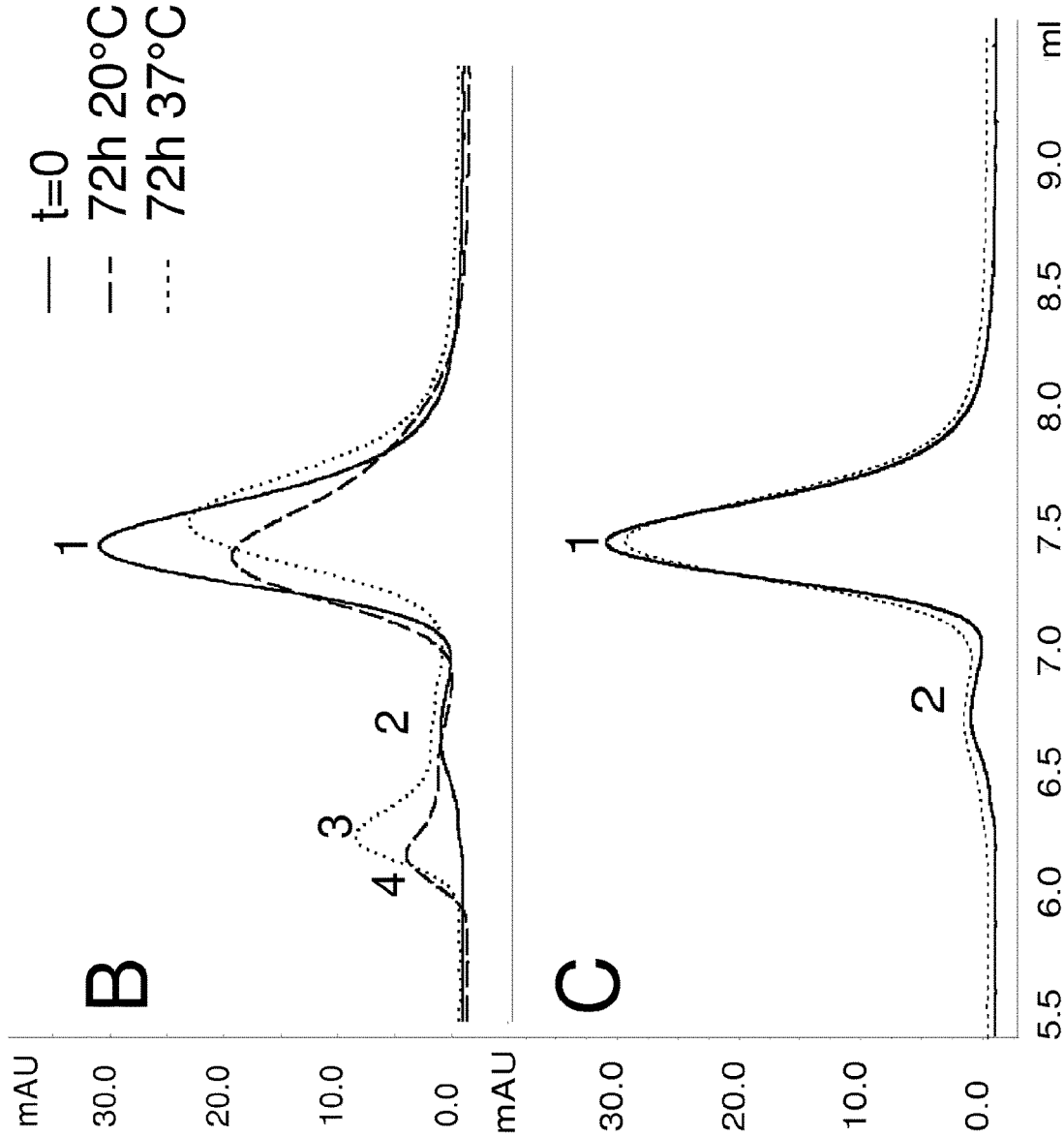

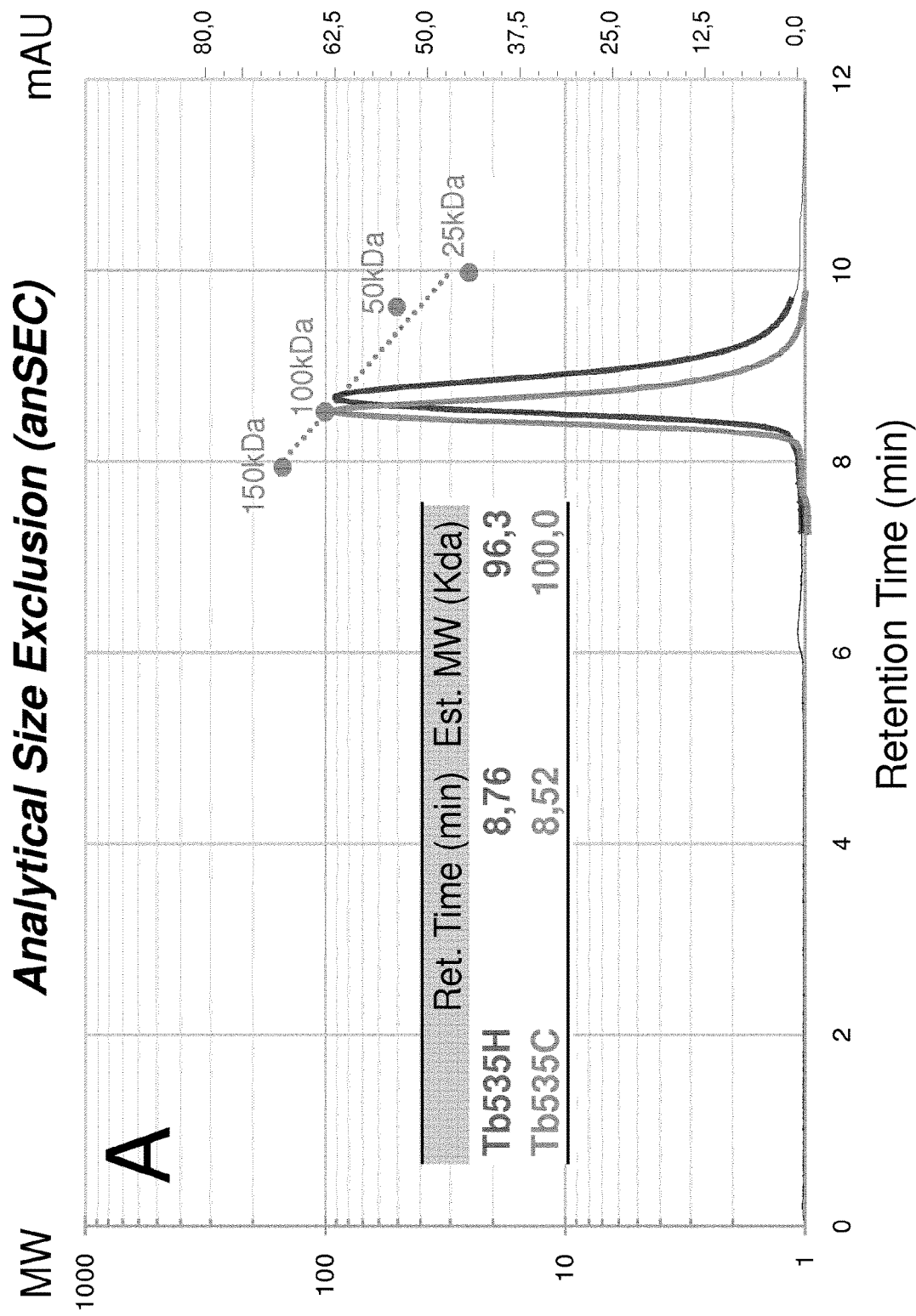

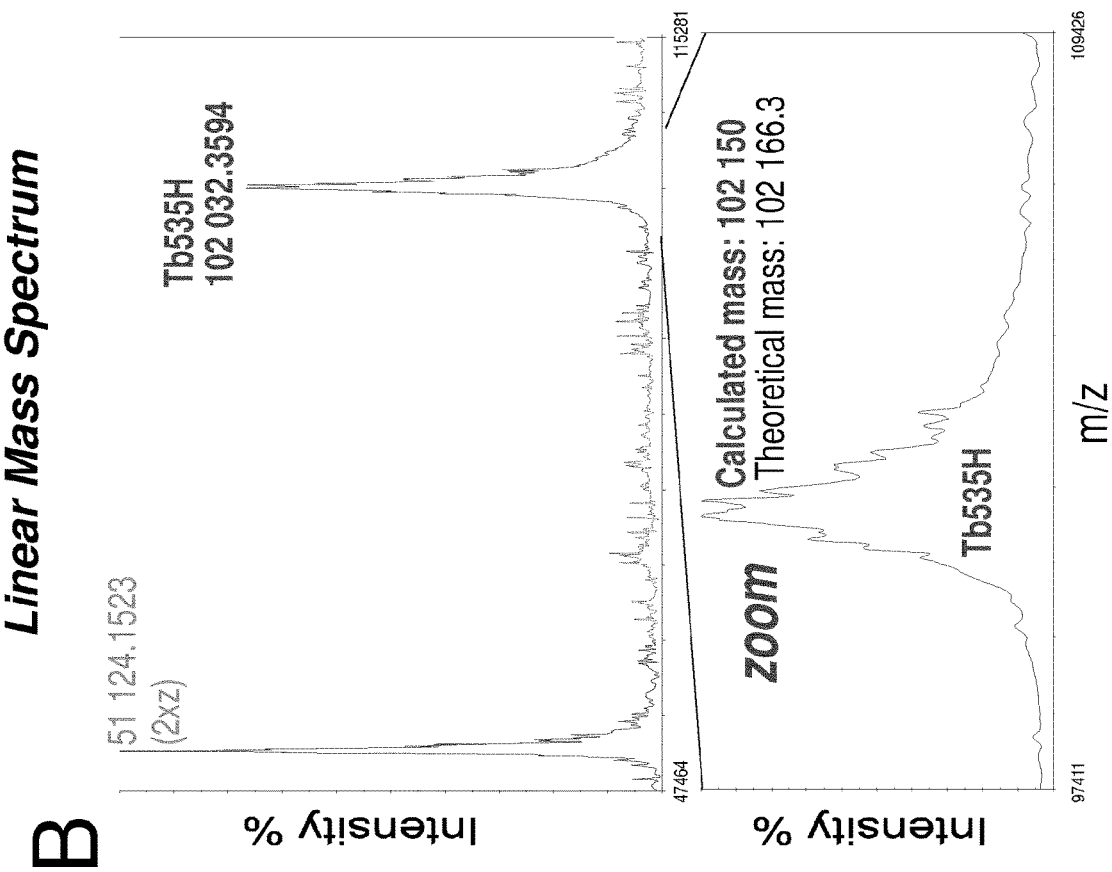

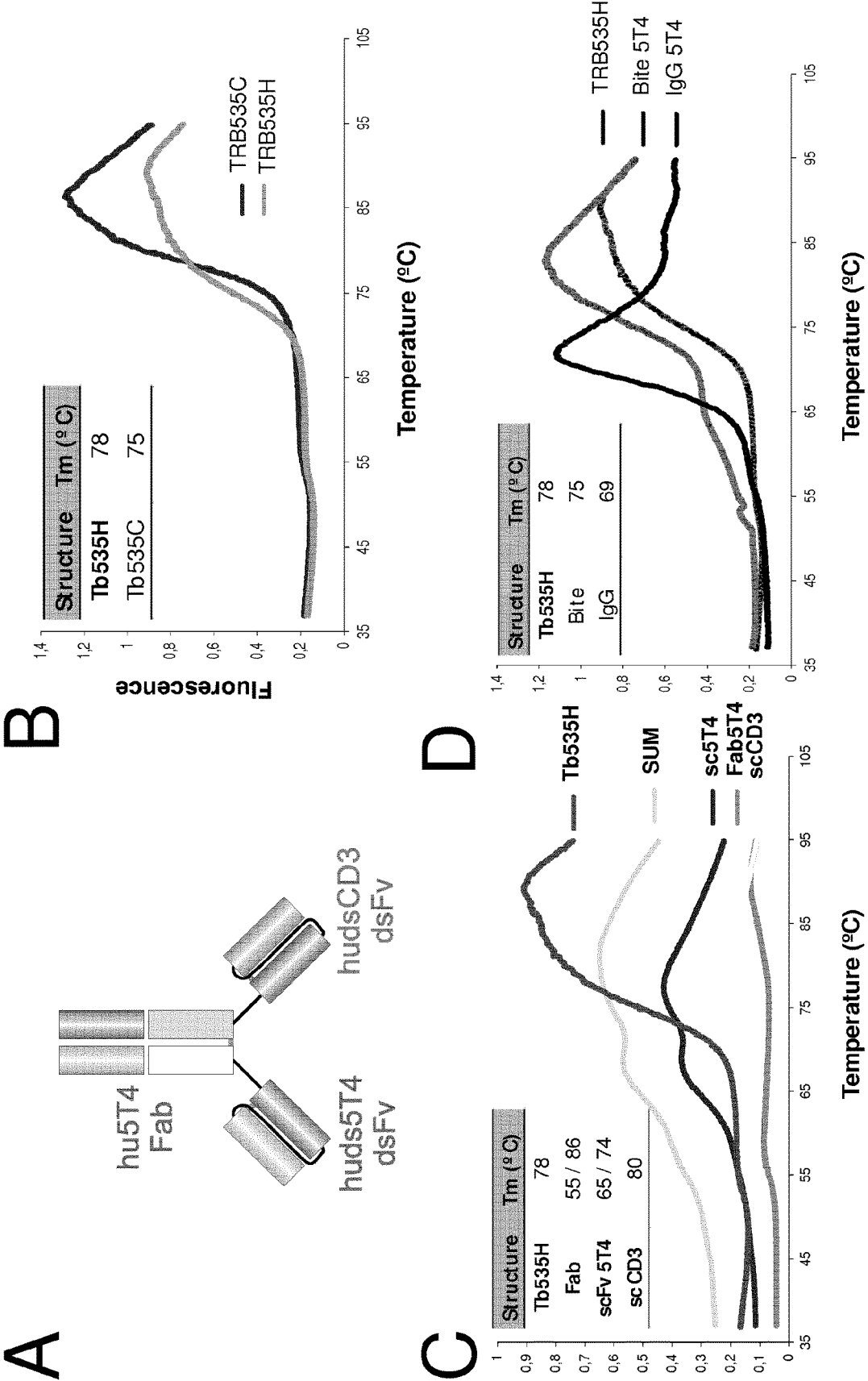

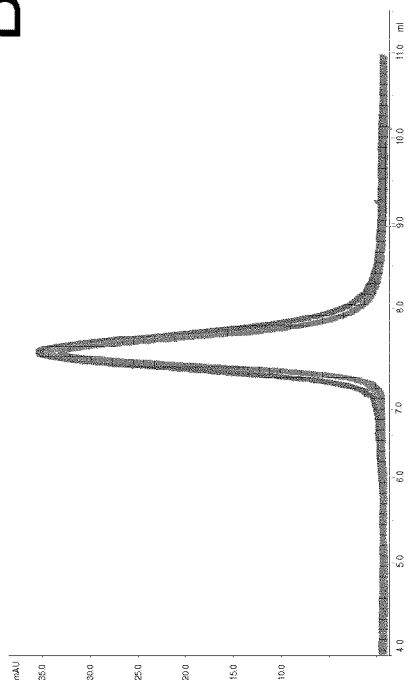
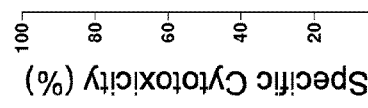
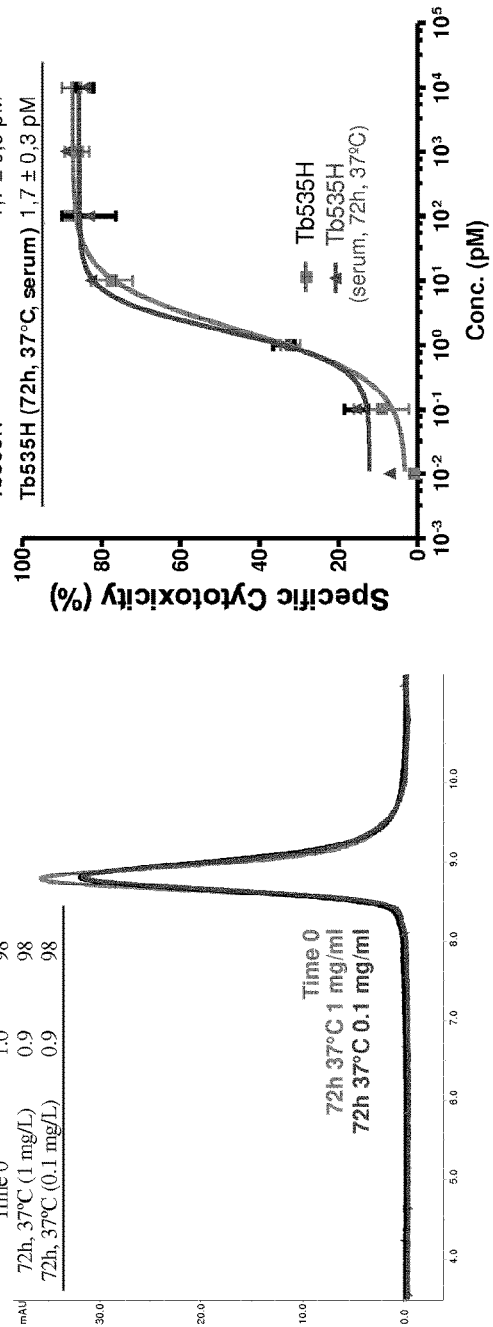
FIG 6B

FIG 10
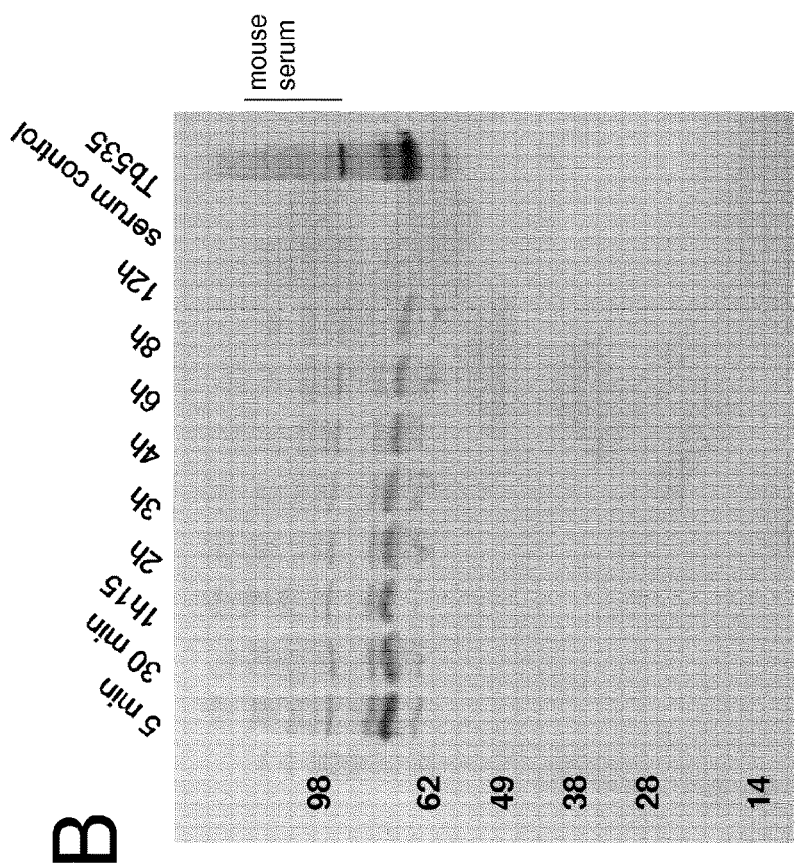
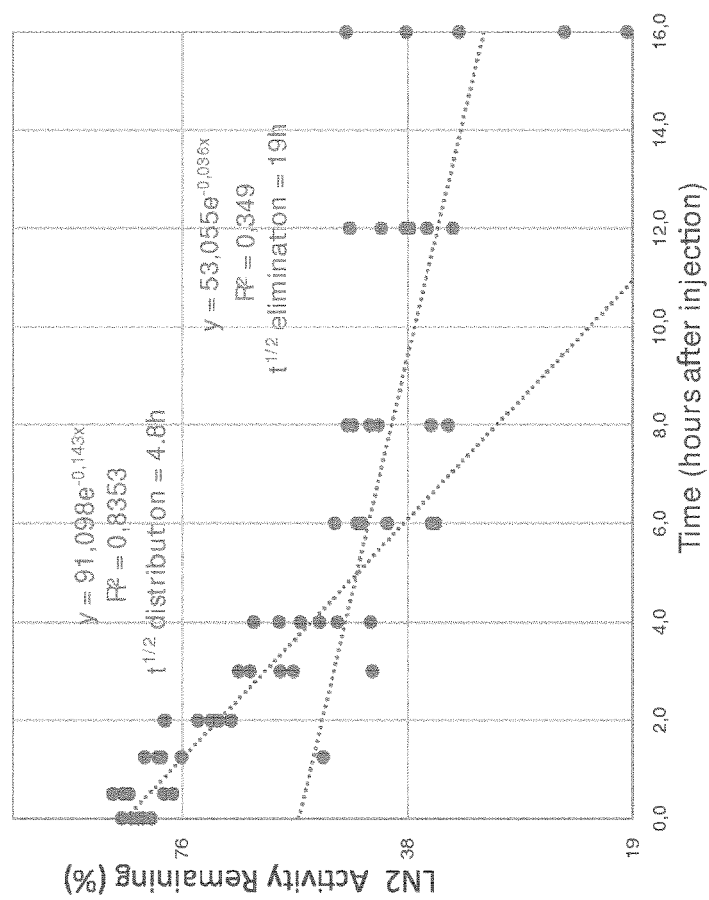

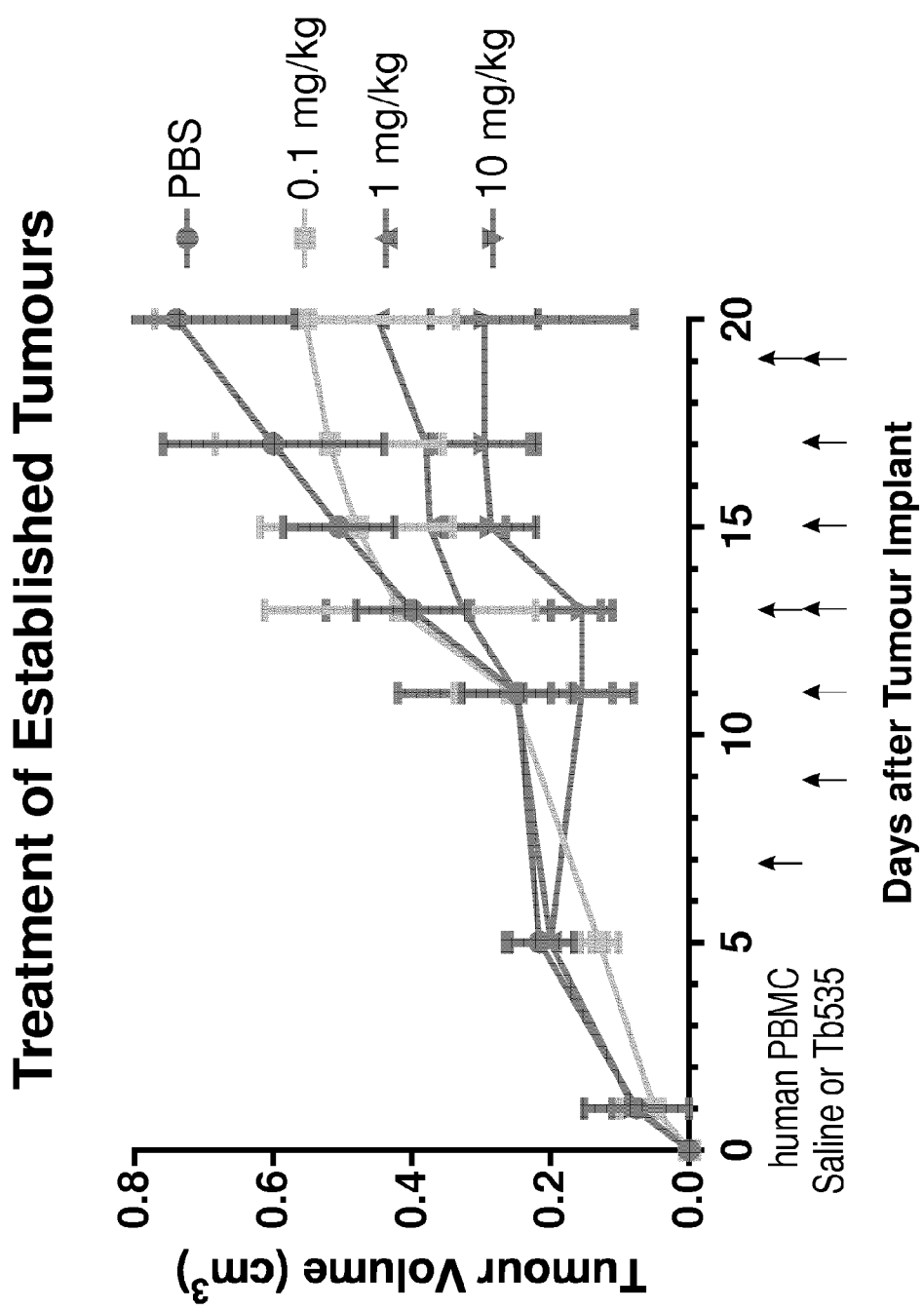

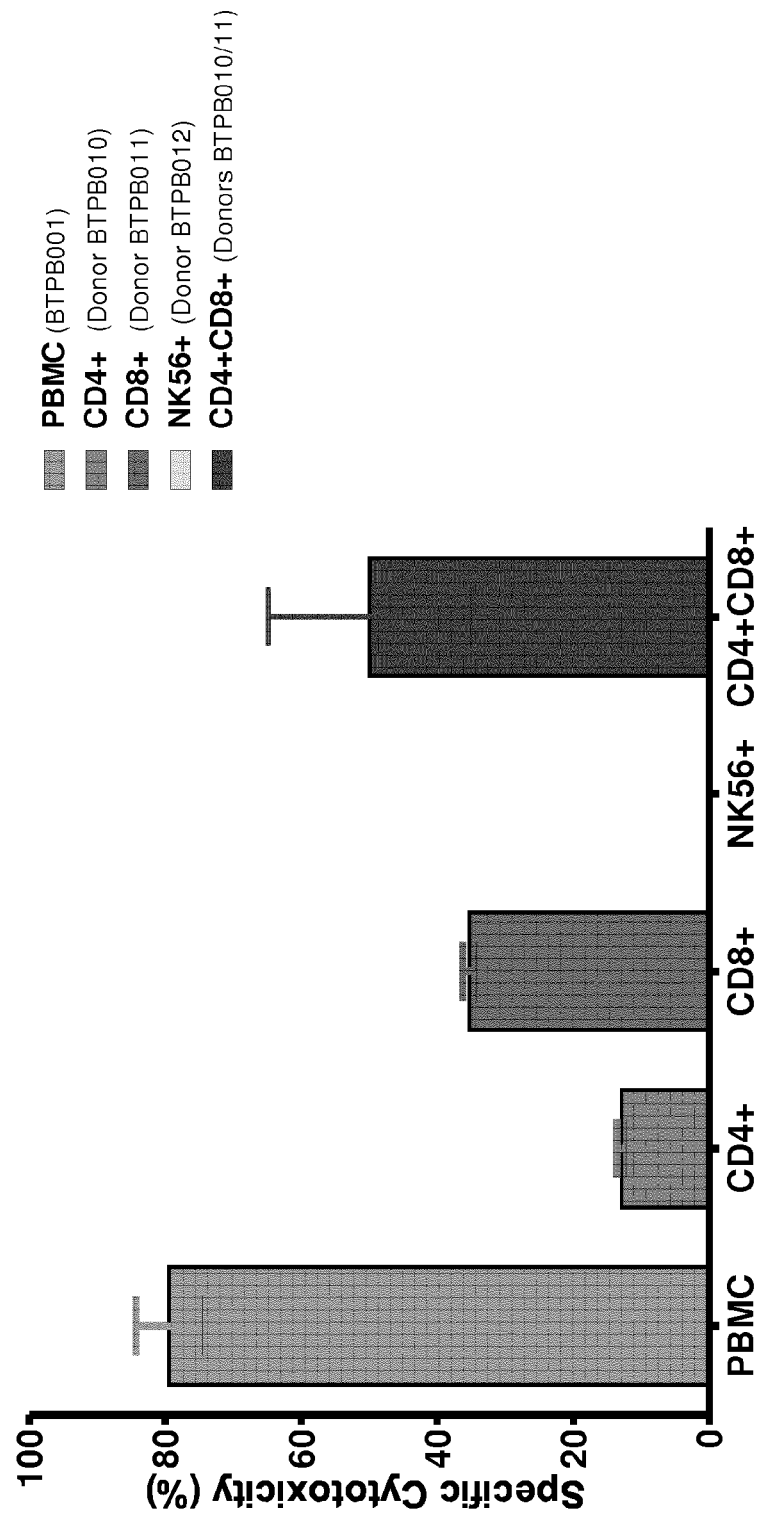

SEQUENCE LISTING

<160> NUMBER OF SEQ ID NOS: 64

<210> SEQ ID NO 1
<211> LENGTH: 120
<212> TYPE: PRT
<213> ORGANISM: Artificial
<220> FEATURE:
<223> OTHER INFORMATION: Artificial sequence part of the fusion protein

<400> SEQUENCE: 1

```
Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser His Gly Lys Ser Leu Glu Trp Ile
        35                  40                  45

Gly Arg Ile Asn Pro Asn Asn Gly Val Thr Leu Tyr Asn Gln Lys Phe
    50                  55                  60

Lys Asp Lys Ala Ile Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Thr Met Ile Thr Asn Tyr Val Met Asp Tyr Trp Gly Val
                100                 105                 110

Thr Thr Ser Val Thr Val Ser Ser
        115                 120
```

<210> SEQ ID NO 2
<211> LENGTH: 120
<212> TYPE: PRT
<213> ORGANISM: Artificial
<220> FEATURE:
<223> OTHER INFORMATION: Artificial sequence part of the fusion protein

<400> SEQUENCE: 2

```
Glu Val Gln Leu Gln Gln Ser Gly Pro Asp Leu Val Lys Pro Gly Ala
1               5                   10                  15
```

```
Ser Val Lys Ile Ser Cys Lys Ala Ser Gly Tyr Ser Phe Thr Gly Tyr
            20                  25                  30

Tyr Met His Trp Val Lys Gln Ser Pro Gly Lys Gly Leu Glu Trp Ile
        35                  40                  45

Gly Arg Ile Asn Pro Asn Asn Gly Val Thr Leu Tyr Asn Gln Lys Phe
    50                  55                  60

Lys Asp Lys Ala Thr Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Thr Met Ile Thr Asn Tyr Val Met Asp Tyr Trp Gly Gln
            100                 105                 110

Gly Thr Ser Val Thr Val Ser Ser
        115                 120

<210> SEQ ID NO 3
<211> LENGTH: 120
<212> TYPE: PRT
<213> ORGANISM: Artificial
<220> FEATURE:
<223> OTHER INFORMATION: Artificial sequence part of the fusion protein

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Lys Gln Ser Pro Gly Gln Gly Leu Glu Trp Ile
        35                  40                  45

Gly Arg Ile Asn Pro Asn Asn Gly Val Thr Leu Tyr Asn Gln Lys Phe
    50                  55                  60

Lys Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Thr Met Ile Thr Asn Tyr Val Met Asp Tyr Trp Gly Gln
            100                 105                 110

Gly Thr Leu Val Thr Val Ser Ser
        115                 120

<210> SEQ ID NO 4
<211> LENGTH: 120
<212> TYPE: PRT
<213> ORGANISM: Artificial
<220> FEATURE:
<223> OTHER INFORMATION: Artificial sequence part of the fusion protein

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Asn Gly Val Thr Leu Tyr Asn Gln Lys Phe
    50                  55                  60

Lys Asp Arg Val Thr Met Thr Arg Asp Thr Ser Ile Ser Thr Ala Tyr
65                  70                  75                  80
```

Met Glu Leu Ser Arg Leu Arg Ser Asp Asp Thr Ala Val Tyr Tyr Cys
                85                  90                  95

Ala Arg Ser Thr Met Ile Thr Asn Tyr Val Met Asp Tyr Trp Gly Gln
            100                 105                 110

Gly Thr Leu Val Thr Val Ser Ser
        115                 120

<210> SEQ ID NO 5
<211> LENGTH: 120
<212> TYPE: PRT
<213> ORGANISM: Artificial
<220> FEATURE:
<223> OTHER INFORMATION: Artificial sequence part of the fusion protein

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Asn Gly Val Thr Leu Tyr Asn Gln Lys Phe
    50                  55                  60

Lys Asp Arg Val Thr Ile Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Met Ile Thr Asn Tyr Val Met Asp Tyr Trp Gly Gln
            100                 105                 110

Gly Thr Leu Val Thr Val Ser Ser
        115                 120

<210> SEQ ID NO 6
<211> LENGTH: 120
<212> TYPE: PRT
<213> ORGANISM: Artificial
<220> FEATURE:
<223> OTHER INFORMATION: Artificial sequence part of the fusion protein

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Tyr Met His Trp Val Lys Gln Ser Pro Gly Gln Gly Leu Glu Trp Ile
        35                  40                  45

Gly Arg Ile Asn Pro Asn Asn Gly Val Thr Leu Tyr Asn Gln Lys Phe
    50                  55                  60

Lys Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Thr Met Ile Thr Asn Tyr Val Met Asp Tyr Trp Gly Gln
            100                 105                 110

Gly Thr Leu Val Thr Val Ser Ser
        115                 120

```
<210> SEQ ID NO 7
<211> LENGTH: 120
<212> TYPE: PRT
<213> ORGANISM: Artificial
<220> FEATURE:
<223> OTHER INFORMATION: Artificial sequence part of the fusion protein

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Tyr Met His Trp Val Lys Gln Ser Pro Gly Gln Gly Leu Glu Trp Ile
            35                  40                  45

Gly Trp Ile Asn Pro Asn Ser Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Thr Met Ile Thr Asn Tyr Val Met Asp Tyr Trp Gly Gln
                100                 105                 110

Gly Thr Leu Val Thr Val Ser Ser
        115                 120

<210> SEQ ID NO 8
<211> LENGTH: 120
<212> TYPE: PRT
<213> ORGANISM: Artificial
<220> FEATURE:
<223> OTHER INFORMATION: Artificial sequence part of the fusion protein

<400> SEQUENCE: 8

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ser Phe Thr Gly Tyr
                20                  25                  30

Tyr Met His Trp Val Arg Gln Ala Pro Gly Gln Gly Leu Glu Trp Met
            35                  40                  45

Gly Arg Ile Asn Pro Asn Asn Gly Val Thr Leu Tyr Asn Gln Lys Phe
        50                  55                  60

Lys Asp Lys Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Ser Thr Met Ile Thr Asn Tyr Val Met Asp Tyr Trp Gly Gln
                100                 105                 110

Gly Thr Leu Val Thr Val Ser Ser
        115                 120

<210> SEQ ID NO 9
<211> LENGTH: 120
<212> TYPE: PRT
<213> ORGANISM: Artificial
<220> FEATURE:
<223> OTHER INFORMATION: Artificial sequence part of the fusion protein

<400> SEQUENCE: 9

Gln Val Gln Leu Val Gln Ser Gly Ala Glu Val Lys Lys Pro Gly Ala
1               5                   10                  15
```

-continued

Ser Val Lys Val Ser Cys Lys Val Ser Gly Tyr Ser Phe Thr Gly Tyr
            20                  25                  30

Tyr Met His Trp Val Arg Gln Ala Pro Gly Lys Gly Leu Glu Trp Met
            35                  40                  45

Gly Arg Ile Asn Pro Asn Asn Gly Val Thr Leu Tyr Asn Gln Lys Phe
50                      55                  60

Lys Asp Lys Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ser Thr Met Ile Thr Asn Tyr Val Met Asp Tyr Trp Gly Gln
                100                 105                 110

Gly Thr Leu Val Thr Val Ser Ser
            115                 120

<210> SEQ ID NO 10
<211> LENGTH: 120
<212> TYPE: PRT
<213> ORGANISM: Artificial
<220> FEATURE:
<223> OTHER INFORMATION: Artificial sequence part of the fusion protein

<400> SEQUENCE: 10

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Arg Gly Gln Arg Leu Glu Trp Ile
            35                  40                  45

Gly Arg Ile Asn Pro Asn Asn Gly Val Thr Leu Tyr Asn Gln Lys Phe
50                      55                  60

Lys Asp Lys Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Ser Thr Met Ile Thr Asn Tyr Val Met Asp Tyr Trp Gly Gln
                100                 105                 110

Gly Thr Leu Val Thr Val Ser Ser
            115                 120

<210> SEQ ID NO 11
<211> LENGTH: 120
<212> TYPE: PRT
<213> ORGANISM: Artificial
<220> FEATURE:
<223> OTHER INFORMATION: Artificial sequence part of the fusion protein

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Arg Leu Glu Trp Met
            35                  40                  45

Gly Arg Ile Asn Pro Asn Asn Gly Val Thr Leu Tyr Asn Gln Lys Phe
50                      55                  60

Lys Asp Lys Val Thr Ile Thr Arg Asp Thr Ser Ala Ser Thr Ala Tyr

```
                65                  70                  75                  80
Met Glu Leu Ser Ser Leu Arg Ser Glu Asp Thr Ala Val Tyr Tyr Cys
                    85                  90                  95

Ala Arg Ser Thr Met Ile Thr Asn Tyr Val Met Asp Tyr Trp Gly Gln
                100                 105                 110

Gly Thr Leu Val Thr Val Ser Ser
            115                 120
```

<210> SEQ ID NO 12
<211> LENGTH: 120
<212> TYPE: PRT
<213> ORGANISM: Artificial
<220> FEATURE:
<223> OTHER INFORMATION: Artificial sequence part of the fusion protein

<400> SEQUENCE: 12

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Gly Tyr
                20                  25                  30

Tyr Met His Trp Val Arg Gln Ala Pro Gly Gln Gly Leu Glu Trp Met
            35                  40                  45

Gly Arg Ile Asn Pro Asn Asn Gly Val Thr Leu Tyr Asn Gln Lys Phe
        50                  55                  60

Lys Asp Lys Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Ser Thr Met Ile Thr Asn Tyr Val Met Asp Tyr Trp Gly Gln
                100                 105                 110

Gly Thr Leu Val Thr Val Ser Ser
            115                 120
```

<210> SEQ ID NO 13
<211> LENGTH: 120
<212> TYPE: PRT
<213> ORGANISM: Artificial
<220> FEATURE:
<223> OTHER INFORMATION: Artificial sequence part of the fusion protein

<400> SEQUENCE: 13

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ser Phe Thr Gly Tyr
                20                  25                  30

Tyr Met His Trp Val Arg Gln Ala Pro Gly Gln Gly Leu Glu Trp Met
            35                  40                  45

Gly Arg Ile Asn Pro Asn Asn Gly Val Thr Leu Tyr Asn Gln Lys Phe
        50                  55                  60

Lys Asp Lys Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Ser Thr Met Ile Thr Asn Tyr Val Met Asp Tyr Trp Gly Gln
                100                 105                 110

Gly Thr Leu Val Thr Val Ser Ser
            115                 120
```

```
<210> SEQ ID NO 14
<211> LENGTH: 120
<212> TYPE: PRT
<213> ORGANISM: Artificial
<220> FEATURE:
<223> OTHER INFORMATION: Artificial sequence part of the fusion protein

<400> SEQUENCE: 14

Gln Val Lys Leu Gln Gln Ser Gly Pro Gly Leu Val Thr Pro Ser Gln
1               5                   10                  15

Ser Leu Ser Ile Thr Cys Thr Val Ser Gly Tyr Ser Phe Thr Gly Tyr
                20                  25                  30

Tyr Met His Trp Val Arg Gln Ser Pro Gly Gln Gly Leu Glu Trp Leu
            35                  40                  45

Gly Arg Ile Asn Pro Asn Asn Gly Val Thr Leu Tyr Asn Gln Lys Phe
        50                  55                  60

Lys Asp Lys Lys Ser Ile Ser Lys Asp Asn Ser Lys Ser Gln Val Phe
65                  70                  75                  80

Leu Lys Met Asn Ser Leu Gln Ala Asp Asp Thr Ala Val Tyr Tyr Cys
                85                  90                  95

Ala Arg Ser Thr Met Ile Thr Asn Tyr Val Met Asp Tyr Trp Gly Gln
            100                 105                 110

Gly Thr Thr Val Thr Val Ser Ser
        115                 120

<210> SEQ ID NO 15
<211> LENGTH: 120
<212> TYPE: PRT
<213> ORGANISM: Artificial
<220> FEATURE:
<223> OTHER INFORMATION: Artificial sequence part of the fusion protein

<400> SEQUENCE: 15

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Phe Thr Gly Tyr
                20                  25                  30

Tyr Met His Trp Val Arg Gln Pro Pro Gly Lys Gly Leu Glu Trp Ile
            35                  40                  45

Gly Arg Ile Asn Pro Asn Asn Gly Val Thr Leu Tyr Asn Gln Lys Phe
        50                  55                  60

Lys Asp Lys Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Thr Met Ile Thr Asn Tyr Val Met Asp Tyr Trp Gly Gln
            100                 105                 110

Gly Thr Leu Val Thr Val Ser Ser
        115                 120

<210> SEQ ID NO 16
<211> LENGTH: 107
<212> TYPE: PRT
<213> ORGANISM: Artificial
<220> FEATURE:
<223> OTHER INFORMATION: Artificial sequence part of the fusion protein

<400> SEQUENCE: 16

Asp Ile Val Met Thr Gln Thr Pro Thr Phe Leu Leu Val Ser Ala Cys
```

```
                1               5                   10                  15
Asp Arg Val Thr Ile Thr Cys Lys Ala Ser Gln Ser Val Ser Asn Asp
                20                  25                  30

Val Ala Trp Tyr Gln Gln Lys Pro Gly Gln Ser Pro Thr Leu Leu Ile
            35                  40                  45

Ser Tyr Thr Ser Ser Arg Tyr Ala Gly Val Pro Asp Arg Phe Ile Gly
        50                  55                  60

Ser Gly Tyr Gly Thr Asp Phe Thr Phe Thr Ile Ser Thr Leu Gln Ala
65                  70                  75                  80

Glu Asp Leu Ala Val Tyr Phe Cys Gln Gln Asp Tyr Asn Ser Pro Pro
                85                  90                  95

Thr Phe Gly Gly Gly Thr Lys Leu Glu Ile Lys
            100                 105

<210> SEQ ID NO 17
<211> LENGTH: 108
<212> TYPE: PRT
<213> ORGANISM: Artificial
<220> FEATURE:
<223> OTHER INFORMATION: Artificial sequence part of the fusion protein

<400> SEQUENCE: 17

Ala Ser Ile Val Met Thr Gln Thr Pro Thr Ser Leu Leu Val Ser Ala
1               5                   10                  15

Gly Asp Arg Val Thr Ile Thr Cys Lys Ala Ser Gln Ser Val Ser Asn
                20                  25                  30

Asp Val Ala Trp Tyr Gln Gln Lys Pro Gly Gln Ser Pro Lys Leu Leu
            35                  40                  45

Ile Ser Tyr Thr Ser Ser Arg Tyr Ala Gly Val Pro Asp Arg Phe Ser
        50                  55                  60

Gly Ser Gly Tyr Gly Thr Asp Phe Thr Leu Thr Ile Ser Ser Val Gln
65                  70                  75                  80

Ala Glu Asp Ala Ala Val Tyr Phe Cys Gln Gln Asp Tyr Asn Ser Pro
                85                  90                  95

Pro Thr Phe Gly Gly Gly Thr Lys Leu Glu Ile Lys
            100                 105

<210> SEQ ID NO 18
<211> LENGTH: 107
<212> TYPE: PRT
<213> ORGANISM: Artificial
<220> FEATURE:
<223> OTHER INFORMATION: Artificial sequence part of the fusion protein

<400> SEQUENCE: 18

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asn Asp
                20                  25                  30

Val Ala Trp Tyr Gln Gln Lys Pro Gly Gln Ser Pro Lys Leu Leu Ile
            35                  40                  45

Ser Tyr Thr Ser Ser Arg Tyr Ala Gly Val Pro Asp Arg Phe Ser Gly
        50                  55                  60

Ser Gly Ser Gly Thr Asp Phe Thr Leu Thr Ile Ser Ser Leu Gln Ala
65                  70                  75                  80

Glu Asp Val Ala Val Tyr Phe Cys Gln Gln Asp Tyr Asn Ser Pro Pro
                85                  90                  95
```

Thr Phe Gly Gly Gly Thr Lys Leu Glu Ile Lys
            100                 105

<210> SEQ ID NO 19
<211> LENGTH: 107
<212> TYPE: PRT
<213> ORGANISM: Artificial
<220> FEATURE:
<223> OTHER INFORMATION: Artificial sequence part of the fusion protein

<400> SEQUENCE: 19

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asn Asp
            20                  25                  30

Val Ala Trp Tyr Gln Gln Lys Pro Gly Gln Pro Pro Lys Leu Leu Ile
        35                  40                  45

Tyr Tyr Thr Ser Ser Arg Tyr Ala Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Asp Tyr Asn Ser Pro Pro
                85                  90                  95

Thr Phe Gly Gly Gly Thr Lys Leu Glu Ile Lys
            100                 105

<210> SEQ ID NO 20
<211> LENGTH: 107
<212> TYPE: PRT
<213> ORGANISM: Artificial
<220> FEATURE:
<223> OTHER INFORMATION: Artificial sequence part of the fusion protein

<400> SEQUENCE: 20

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Gly Ile Arg Asn Asp
            20                  25                  30

Leu Gly Trp Tyr Gln Gln Lys Pro Gly Gln Pro Pro Lys Leu Leu Ile
        35                  40                  45

Tyr Tyr Thr Ser Ser Arg Tyr Ala Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Asp Tyr Asn Ser Pro Pro
                85                  90                  95

Thr Phe Gly Gly Gly Thr Lys Leu Glu Ile Lys
            100                 105

<210> SEQ ID NO 21
<211> LENGTH: 107
<212> TYPE: PRT
<213> ORGANISM: Artificial
<220> FEATURE:
<223> OTHER INFORMATION: Articial sequence part of the fusion protein

<400> SEQUENCE: 21

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asn Asp

```
            20                  25                  30

Val Ala Trp Tyr Gln Gln Lys Pro Gly Gln Pro Pro Lys Leu Leu Ile
        35                  40                  45

Tyr Ala Ala Ser Ser Leu Gln Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Asp Tyr Asn Ser Pro Pro
                85                  90                  95

Thr Phe Gly Gly Gly Thr Lys Leu Glu Ile Lys
            100                 105

<210> SEQ ID NO 22
<211> LENGTH: 107
<212> TYPE: PRT
<213> ORGANISM: Artificial
<220> FEATURE:
<223> OTHER INFORMATION: Artificial sequence part of the fusion protein

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Arg Leu Ile
        35                  40                  45

Tyr Tyr Thr Ser Arg Tyr Ala Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Asp Tyr Asn Ser Pro Pro
                85                  90                  95

Thr Phe Gly Gly Gly Thr Lys Leu Glu Ile Lys
            100                 105

<210> SEQ ID NO 23
<211> LENGTH: 107
<212> TYPE: PRT
<213> ORGANISM: Artificial
<220> FEATURE:
<223> OTHER INFORMATION: Artificial sequence part of the fusion protein

<400> SEQUENCE: 23

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asn Asp
            20                  25                  30

Val Ala Trp Tyr Gln Gln Lys Pro Gly Gln Pro Pro Lys Leu Leu Ile
        35                  40                  45

Tyr Tyr Thr Ser Arg Tyr Ala Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Asp Tyr Asn Ser Pro Pro
                85                  90                  95

Thr Phe Gly Gly Gly Thr Lys Leu Glu Ile Lys
            100                 105
```

<210> SEQ ID NO 24
<211> LENGTH: 107
<212> TYPE: PRT
<213> ORGANISM: Artificial
<220> FEATURE:
<223> OTHER INFORMATION: Artificial sequence part of the fusion protein

<400> SEQUENCE: 24

Glu Ile Val Met Thr Gln Ser Pro Ser Thr Leu Ser Ala Ser Val Gly
1               5                   10                  15

Asp Arg Val Ile Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Tyr Thr Ser Ser Arg Tyr Ala Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Gln Asp Tyr Asn Ser Pro Pro
                85                  90                  95

Thr Phe Gly Gln Gly Thr Lys Leu Thr Val Leu
            100                 105

<210> SEQ ID NO 25
<211> LENGTH: 105
<212> TYPE: PRT
<213> ORGANISM: Artificial
<220> FEATURE:
<223> OTHER INFORMATION: Artificial sequence part of the fusion protein

<400> SEQUENCE: 25

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Ser Asn Asp
            20                  25                  30

Val Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp His Phe
                85                  90                  95

Gly Gln Gly Thr Lys Val Glu Ile Lys
            100                 105

<210> SEQ ID NO 26
<211> LENGTH: 119
<212> TYPE: PRT
<213> ORGANISM: Artificial
<220> FEATURE:
<223> OTHER INFORMATION: Artificial sequence part of the fusion protein

<400> SEQUENCE: 26

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile

```
            35                  40                  45
Gly Tyr Ile Asn Pro Ser Arg Gly Tyr Thr Asn Tyr Asn Gln Lys Val
 50                  55                  60

Lys Asp Arg Phe Thr Ile Ser Arg Asp Asn Ser Lys Asn Thr Ala Phe
 65                  70                  75                  80

Leu Gln Met Asp Ser Leu Arg Pro Glu Asp Thr Gly Val Tyr Phe Cys
                 85                  90                  95

Ala Arg Tyr Tyr Asp Asp His Tyr Cys Leu Asp Tyr Trp Gly Gln Gly
                100                 105                 110

Thr Pro Val Thr Val Ser Ser
            115

<210> SEQ ID NO 27
<211> LENGTH: 119
<212> TYPE: PRT
<213> ORGANISM: Artificial
<220> FEATURE:
<223> OTHER INFORMATION: Artificial sequence part of the fusion protein

<400> SEQUENCE: 27

Gln Val Gln Leu Val Gln Ser Gly Gly Gly Val Val Gln Pro Gly Arg
 1               5                  10                  15

Ser Leu Arg Leu Ser Cys Lys Ala Ser Gly Tyr Thr Phe Thr Arg Tyr
                 20                  25                  30

Thr Met His Trp Val Arg Gln Ala Pro Gly Lys Gly Leu Glu Trp Ile
             35                  40                  45

Gly Tyr Ile Asn Pro Ser Arg Gly Tyr Thr Asn Tyr Asn Gln Lys Val
 50                  55                  60

Lys Asp Arg Phe Thr Ile Ser Arg Asp Asn Ser Lys Asn Thr Ala Phe
 65                  70                  75                  80

Leu Gln Met Asp Ser Leu Arg Pro Glu Asp Thr Gly Val Tyr Phe Cys
                 85                  90                  95

Ala Arg Tyr Tyr Asp Asp His Tyr Ser Leu Asp Tyr Trp Gly Gln Gly
                100                 105                 110

Thr Pro Val Thr Val Ser Ser
            115

<210> SEQ ID NO 28
<211> LENGTH: 119
<212> TYPE: PRT
<213> ORGANISM: Artificial
<220> FEATURE:
<223> OTHER INFORMATION: Artificial sequence part of the fusion protein

<400> SEQUENCE: 28

Asp Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Arg Tyr
                 20                  25                  30

Thr Met His Trp Val Arg Gln Ala Pro Gly Gln Gly Leu Glu Trp Ile
             35                  40                  45

Gly Tyr Ile Asn Pro Ser Arg Gly Tyr Thr Asn Tyr Ala Asp Ser Val
 50                  55                  60

Lys Gly Arg Phe Thr Ile Thr Thr Asp Lys Ser Thr Ser Thr Ala Tyr
 65                  70                  75                  80

Met Glu Leu Ser Ser Leu Arg Ser Glu Asp Thr Ala Thr Tyr Tyr Cys
                 85                  90                  95
```

```
Ala Arg Tyr Tyr Asp Asp His Tyr Cys Leu Asp Tyr Trp Gly Gln Gly
            100                 105                 110

Thr Thr Val Thr Val Ser Ser
        115

<210> SEQ ID NO 29
<211> LENGTH: 119
<212> TYPE: PRT
<213> ORGANISM: Artificial
<220> FEATURE:
<223> OTHER INFORMATION: Artificial sequence part of the fusion protein

<400> SEQUENCE: 29

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Cys Leu Glu Trp Met
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Ala Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Leu Val Thr Val Ser Ser
        115

<210> SEQ ID NO 30
<211> LENGTH: 118
<212> TYPE: PRT
<213> ORGANISM: Artificial
<220> FEATURE:
<223> OTHER INFORMATION: Artificial sequence part of the fusion protein

<400> SEQUENCE: 30

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Lys Phe Ser Gly Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Lys Tyr Tyr Val Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Met Gly Tyr Trp His Phe Asp Leu Trp Gly Arg Gly Thr
            100                 105                 110

Leu Val Thr Val Ser Ser
        115

<210> SEQ ID NO 31
<211> LENGTH: 114
<212> TYPE: PRT
<213> ORGANISM: Artificial
```

<220> FEATURE:
<223> OTHER INFORMATION: Artificial sequence part of the fusion protein

<400> SEQUENCE: 31

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Tyr Thr Lys Tyr Asn Gln Lys Phe
    50                  55                  60

Lys Asp Lys Ala Thr Leu Thr Ala Asp Lys Ser Ser Ser Thr Ala Tyr
65                  70                  75                  80

His Gln Leu Ser Ser Leu Thr Ser Glu Asp Ser Ala Val Tyr Tyr Cys
                85                  90                  95

Ala Arg Trp Gln Asp Tyr Asp Val Tyr Phe Asp Tyr Trp Gly Gln Gly
            100                 105                 110

Thr Thr
```

<210> SEQ ID NO 32
<211> LENGTH: 122
<212> TYPE: PRT
<213> ORGANISM: Artificial
<220> FEATURE:
<223> OTHER INFORMATION: Artificial sequence part of the fusion protein

<400> SEQUENCE: 32

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Thr Thr Tyr Ala Asp Ser Val
    50                  55                  60

Lys Gly Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser
        115                 120
```

<210> SEQ ID NO 33
<211> LENGTH: 120
<212> TYPE: PRT
<213> ORGANISM: Artificial
<220> FEATURE:
<223> OTHER INFORMATION: Artificial sequence part of the fusion protein

<400> SEQUENCE: 33

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Ile Ser Tyr
            20                  25                  30

Thr Met His Trp Val Lys Gln Arg Pro Gly Gln Gly Leu Glu Trp Ile
```

```
                35                  40                  45
Gly Tyr Ile Asn Pro Arg Ser Gly Tyr Thr His Tyr Asn Gln Lys Leu
        50                  55                  60

Lys Asp Lys Ala Thr Leu Thr Ala Asp Lys Ser Ser Ser Ala Tyr
65                  70                  75                  80

Met Gln Leu Ser Ser Leu Thr Ser Glu Asp Ser Ala Val Tyr Tyr Cys
                85                  90                  95

Ala Arg Ser Ala Tyr Tyr Asp Tyr Asp Gly Phe Ala Tyr Trp Gly Gln
            100                 105                 110

Gly Thr Leu Val Thr Val Ser Ala
        115                 120

<210> SEQ ID NO 34
<211> LENGTH: 106
<212> TYPE: PRT
<213> ORGANISM: Artificial
<220> FEATURE:
<223> OTHER INFORMATION: Artificial sequence part of the fusion protein

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr
            100                 105

<210> SEQ ID NO 35
<211> LENGTH: 106
<212> TYPE: PRT
<213> ORGANISM: Artificial
<220> FEATURE:
<223> OTHER INFORMATION: Artificial sequence part of the fusion protein

<400> SEQUENCE: 35

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn
            100                 105
```

```
<210> SEQ ID NO 36
<211> LENGTH: 106
<212> TYPE: PRT
<213> ORGANISM: Artificial
<220> FEATURE:
<223> OTHER INFORMATION: Artificial sequence parr of the fusion protein

<400> SEQUENCE: 36

Asp Ile Gln Met Thr Gln Ser Pro Ser Leu Ser Ala Ser Val Gly
1               5                   10                  15

Asp Arg Val Thr Ile Thr Cys Arg Ala Ser Gln Ser Val Ser Tyr Met
            20                  25                  30

Asn Trp Tyr Gln Gln Lys Pro Gly Lys Ala Pro Lys Arg Trp Ile Tyr
        35                  40                  45

Asp Thr Ser Lys Val Ala Ser Gly Val Pro Ala Arg Phe Ser Gly Ser
    50                  55                  60

Gly Ser Gly Thr Asp Tyr Ser Leu Thr Ile Asn Ser Leu Glu Ala Glu
65                  70                  75                  80

Asp Ala Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 37
<211> LENGTH: 108
<212> TYPE: PRT
<213> ORGANISM: Artificial
<220> FEATURE:
<223> OTHER INFORMATION: Artificial sequence part of the fusion protein

<400> SEQUENCE: 37

Asp Ile Gln Leu Thr Gln Ser Pro Ser Ile Leu Ser Ala Ser Val Gly
1               5                   10                  15

Asp Arg Val Thr Ile Thr Cys Arg Ala Ser Ser Ser Val Ser Tyr Met
            20                  25                  30

Asn Trp Tyr Gln Gln Lys Pro Gly Lys Ala Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Glu Tyr Thr Leu Thr Ile Ser Ser Met Gln Pro Glu
65                  70                  75                  80

Asp Phe Ala Thr Tyr Tyr Cys Gln Gln Trp Ser Ser Asn Pro Leu Thr
                85                  90                  95

Phe Gly Cys Gly Thr Lys Val Glu Ile Lys Arg Thr
            100                 105

<210> SEQ ID NO 38
<211> LENGTH: 108
<212> TYPE: PRT
<213> ORGANISM: Artificial
<220> FEATURE:
<223> OTHER INFORMATION: Artificial sequence part of the fusion protein

<400> SEQUENCE: 38

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
```

```
                35                  40                  45
Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Leu Thr Phe Gly Gly Gly Thr Lys Val Glu Ile Lys
            100                 105

<210> SEQ ID NO 39
<211> LENGTH: 104
<212> TYPE: PRT
<213> ORGANISM: Artificial
<220> FEATURE:
<223> OTHER INFORMATION: Artificial sequence part of the fusion protein

<400> SEQUENCE: 39

Gln Ile Val Leu Ser Gln Ser Pro Ala Leu Leu Ser Ala Ser Pro Gly
1               5                   10                  15

Glu Lys Val Thr Met Thr Cys Arg Ala Ser Ser Ser Tyr Met His Trp
                20                  25                  30

Tyr Gln Gln Lys Pro Gly Ser Ser Pro Lys Pro Trp Ile Tyr Ala Thr
            35                  40                  45

Ser Asn Leu Ala Ser Gly Val Pro Ala Arg Phe Ser Gly Ser Gly Ser
    50                  55                  60

Gly Thr Ser Tyr Ser Leu Thr Ile Ser Arg Val Glu Ala Glu Asp Ala
65                  70                  75                  80

Ala Thr Tyr Tyr Cys Gln Gln Trp Ser Ser Asn Pro Pro Thr Phe Gly
                85                  90                  95

Gly Gly Thr Lys Leu Glu Thr Lys
            100

<210> SEQ ID NO 40
<211> LENGTH: 107
<212> TYPE: PRT
<213> ORGANISM: Artificial
<220> FEATURE:
<223> OTHER INFORMATION: Artificial sequence part of the fusion protein

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys
            100                 105

<210> SEQ ID NO 41
<211> LENGTH: 106
```

```
<212> TYPE: PRT
<213> ORGANISM: Artificial
<220> FEATURE:
<223> OTHER INFORMATION: Artificial sequence part of the fusion protein

<400> SEQUENCE: 41

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Lys Gln Lys Ser Gly Thr Ser Pro Lys Arg Trp Thr Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Ser Gly Thr Lys Leu Glu Ile Lys
            100                 105

<210> SEQ ID NO 42
<211> LENGTH: 247
<212> TYPE: PRT
<213> ORGANISM: Artificial
<220> FEATURE:
<223> OTHER INFORMATION: Combined VH/VL

<400> SEQUENCE: 42

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser Pro Gly Lys Gly Leu Glu Trp Ile
            35                  40                  45

Gly Arg Ile Asn Pro Asn Asn Gly Val Thr Leu Tyr Asn Gln Lys Phe
        50                  55                  60

Lys Asp Lys Ala Thr Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Thr Met Ile Thr Asn Tyr Val Met Asp Tyr Trp Gly Gln
            100                 105                 110

Gly Thr Ser Val Thr Val Ser Ser Ala Ser Gly Gly Gly Gly Ser Gly
            115                 120                 125

Gly Gly Gly Ser Gly Gly Gly Ser Ala Gly Ala Ser Ile Val Met
        130                 135                 140

Thr Gln Thr Pro Thr Ser Leu Leu Val Ser Ala Gly Asp Arg Val Thr
145                 150                 155                 160

Ile Thr Cys Lys Ala Ser Gln Ser Val Ser Asn Asp Val Ala Trp Tyr
                165                 170                 175

Gln Gln Lys Pro Gly Ser Pro Lys Leu Leu Ile Ser Tyr Thr Ser
            180                 185                 190

Ser Arg Tyr Ala Gly Val Pro Asp Arg Phe Ser Gly Ser Gly Tyr Gly
        195                 200                 205

Thr Asp Phe Thr Leu Thr Ile Ser Ser Val Gln Ala Glu Asp Ala Ala
210                 215                 220
```

Val Tyr Phe Cys Gln Gln Asp Tyr Asn Ser Pro Pro Thr Phe Gly Gly
225                 230                 235                 240

Gly Thr Lys Leu Glu Ile Lys
            245

<210> SEQ ID NO 43
<211> LENGTH: 246
<212> TYPE: PRT
<213> ORGANISM: Artificial
<220> FEATURE:
<223> OTHER INFORMATION: Combined VH/VL

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Tyr Met His Trp Val Lys Gln Ser Pro Gly Gln Gly Leu Glu Trp Ile
            35                  40                  45

Gly Arg Ile Asn Pro Asn Asn Gly Val Thr Leu Tyr Asn Gln Lys Phe
    50                  55                  60

Lys Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Thr Met Ile Thr Asn Tyr Val Met Asp Tyr Trp Gly Gln
            100                 105                 110

Gly Thr Leu Val Thr Val Ser Ser Ala Ser Gly Gly Gly Gly Ser Gly
        115                 120                 125

Gly Gly Gly Ser Gly Gly Gly Ser Ala Gly Asp Ile Val Met Thr
        130                 135                 140

Gln Ser Pro Asp Ser Leu Ala Val Ser Leu Gly Glu Arg Ala Thr Ile
145                 150                 155                 160

Asn Cys Lys Ala Ser Gln Ser Val Ser Asn Asp Val Ala Trp Tyr Gln
                165                 170                 175

Gln Lys Pro Gly Gln Pro Pro Lys Leu Leu Ile Tyr Tyr Thr Ser Ser
            180                 185                 190

Arg Tyr Ala Gly Val Pro Asp Arg Phe Ser Gly Ser Gly Ser Gly Thr
    195                 200                 205

Asp Phe Thr Leu Thr Ile Ser Ser Leu Gln Ala Glu Asp Val Ala Val
210                 215                 220

Tyr Tyr Cys Gln Gln Asp Tyr Asn Ser Pro Pro Thr Phe Gly Gly Gly
225                 230                 235                 240

Thr Lys Leu Glu Ile Lys
            245

<210> SEQ ID NO 44
<211> LENGTH: 246
<212> TYPE: PRT
<213> ORGANISM: Artificial
<220> FEATURE:
<223> OTHER INFORMATION: Combined VH/VL

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr

```
                    20                  25                  30
Tyr Met His Trp Val Lys Gln Ser Pro Gly Gln Cys Leu Glu Trp Ile
        35                  40                  45
Gly Arg Ile Asn Pro Asn Asn Gly Val Thr Leu Tyr Asn Gln Lys Phe
    50                  55                  60
Lys Asp Arg Val Thr Met Thr Arg Asp Thr Ser Ile Ser Thr Ala Tyr
 65                  70                  75                  80
Met Glu Leu Ser Arg Leu Arg Ser Asp Asp Thr Ala Val Tyr Tyr Cys
                85                  90                  95
Ala Arg Ser Thr Met Ile Thr Asn Tyr Val Met Asp Tyr Trp Gly Gln
                100                 105                 110
Gly Thr Leu Val Thr Val Ser Ser Ala Ser Gly Gly Gly Gly Ser Gly
                115                 120                 125
Gly Gly Gly Ser Gly Gly Gly Ser Ala Gly Asp Ile Val Met Thr
                130                 135                 140
Gln Ser Pro Asp Ser Leu Ala Val Ser Leu Gly Glu Arg Ala Thr Ile
145                 150                 155                 160
Asn Cys Lys Ala Ser Gln Ser Val Ser Asn Asp Val Ala Trp Tyr Gln
                165                 170                 175
Gln Lys Pro Gly Gln Pro Pro Lys Leu Leu Ile Tyr Thr Ser Ser
                180                 185                 190
Arg Tyr Ala Gly Val Pro Asp Arg Phe Ser Gly Ser Gly Ser Gly Thr
                195                 200                 205
Asp Phe Thr Leu Thr Ile Ser Ser Leu Gln Ala Glu Asp Val Ala Val
                210                 215                 220
Tyr Tyr Cys Gln Gln Asp Tyr Asn Ser Pro Pro Thr Phe Gly Cys Gly
225                 230                 235                 240
Thr Lys Leu Glu Ile Lys
                245

<210> SEQ ID NO 45
<211> LENGTH: 244
<212> TYPE: PRT
<213> ORGANISM: Artificial
<220> FEATURE:
<223> OTHER INFORMATION: Combined VH/VL

<400> SEQUENCE: 45

Gln Val Gln Leu Gln Gln Ser Gly Ala Glu Leu Ala Arg Pro Gly Ala
 1               5                  10                  15
Ser Val Lys Met Ser Cys Lys Ala Ser Gly Tyr Thr Phe Thr Arg Tyr
                20                  25                  30
Thr Met His Trp Val Lys Gln Arg Pro Gly Gln Gly Leu Glu Trp Ile
        35                  40                  45
Gly Tyr Ile Asn Pro Ser Arg Gly Tyr Thr Asn Tyr Asn Gln Lys Phe
    50                  55                  60
Lys Asp Lys Ala Thr Leu Thr Thr Asp Lys Ser Ser Ser Thr Ala Tyr
 65                  70                  75                  80
Met Gln Leu Ser Ser Leu Thr Ser Glu Asp Ser Ala Val Tyr Tyr Cys
                85                  90                  95
Ala Arg Tyr Tyr Asp Asp His Tyr Cys Leu Asp Tyr Trp Gly Gln Gly
                100                 105                 110
Thr Thr Leu Thr Val Ser Ser Ala Ser Gly Gly Gly Gly Ser Gly Gly
                115                 120                 125
Gly Gly Ser Gly Gly Gly Gly Ser Ala Gly Gln Ile Val Leu Thr Gln
```

```
                130             135             140
Ser Pro Ala Ile Met Ser Ala Ser Pro Gly Glu Lys Val Thr Met Thr
145                 150                 155                 160

Cys Ser Ala Ser Ser Ser Val Ser Tyr Met Asn Trp Tyr Gln Gln Lys
                165                 170                 175

Ser Gly Thr Ser Pro Lys Arg Trp Ile Tyr Asp Thr Ser Lys Leu Ala
            180                 185                 190

Ser Gly Val Pro Ala His Phe Arg Gly Ser Gly Ser Gly Thr Ser Tyr
            195                 200                 205

Ser Leu Thr Ile Ser Gly Met Glu Ala Glu Asp Ala Ala Thr Tyr Tyr
            210                 215                 220

Cys Gln Gln Trp Ser Ser Asn Pro Phe Thr Phe Gly Ser Gly Thr Lys
225                 230                 235                 240

Leu Glu Ile Asn

<210> SEQ ID NO 46
<211> LENGTH: 244
<212> TYPE: PRT
<213> ORGANISM: Artificial
<220> FEATURE:
<223> OTHER INFORMATION: Combined VH/VL

<400> SEQUENCE: 46

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Phe Thr Arg Tyr
                20                  25                  30

Thr Met His Trp Val Arg Gln Ala Pro Gly Gln Gly Leu Glu Trp Met
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Ala Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Tyr Asp Asp His Tyr Ser Leu Asp Tyr Trp Gly Gln Gly
                100                 105                 110

Thr Leu Val Thr Val Ser Ser Ala Ser Gly Gly Gly Gly Ser Gly Gly
            115                 120                 125

Gly Gly Ser Gly Gly Gly Gly Ser Ala Gly Asp Ile Gln Leu Thr Gln
        130                 135                 140

Ser Pro Ser Ile Leu Ser Ala Ser Val Gly Asp Arg Val Thr Ile Thr
145                 150                 155                 160

Cys Arg Ala Ser Ser Ser Val Ser Tyr Met Asn Trp Tyr Gln Gln Lys
                165                 170                 175

Pro Gly Lys Ala Pro Lys Arg Trp Ile Tyr Asp Thr Ser Lys Val Ala
            180                 185                 190

Ser Gly Val Pro Tyr Arg Phe Ser Gly Ser Gly Ser Gly Thr Glu Tyr
            195                 200                 205

Thr Leu Thr Ile Ser Ser Met Gln Pro Glu Asp Phe Ala Thr Tyr Tyr
            210                 215                 220

Cys Gln Gln Trp Ser Ser Asn Pro Leu Thr Phe Gly Gly Gly Thr Lys
225                 230                 235                 240

Val Glu Ile Lys
```

```
<210> SEQ ID NO 47
<211> LENGTH: 244
<212> TYPE: PRT
<213> ORGANISM: Artificial
<220> FEATURE:
<223> OTHER INFORMATION: Combined VH/VL

<400> SEQUENCE: 47

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Cys Leu Glu Trp Met
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Ala Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Leu Val Thr Val Ser Ser Ala Ser Gly Gly Gly Ser Gly Gly
        115                 120                 125

Gly Gly Ser Gly Gly Gly Ser Ala Gly Asp Ile Gln Leu Thr Gln
    130                 135                 140

Ser Pro Ser Ile Leu Ser Ala Ser Val Gly Asp Arg Val Thr Ile Thr
145                 150                 155                 160

Cys Arg Ala Ser Ser Ser Val Ser Tyr Met Asn Trp Tyr Gln Gln Lys
                165                 170                 175

Pro Gly Lys Ala Pro Lys Arg Trp Ile Tyr Asp Thr Ser Lys Val Ala
            180                 185                 190

Ser Gly Val Pro Tyr Arg Phe Ser Gly Ser Gly Ser Gly Thr Glu Tyr
        195                 200                 205

Thr Leu Thr Ile Ser Ser Met Gln Pro Glu Asp Phe Ala Thr Tyr Tyr
    210                 215                 220

Cys Gln Gln Trp Ser Ser Asn Pro Leu Thr Phe Gly Cys Gly Thr Lys
225                 230                 235                 240

Val Glu Ile Lys

<210> SEQ ID NO 48
<211> LENGTH: 248
<212> TYPE: PRT
<213> ORGANISM: Artificial
<220> FEATURE:
<223> OTHER INFORMATION: Combined VH/VL

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Cys Leu Glu Trp Val
        35                  40                  45

Ala Leu Ile Asn Pro Tyr Lys Gly Val Thr Thr Tyr Ala Asp Ser Val
    50                  55                  60
```

```
Lys Gly Arg Phe Thr Ile Ser Val Asp Lys Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser Ala Ser Gly Gly Gly Gly
        115                 120                 125

Ser Gly Gly Gly Gly Ser Gly Gly Gly Ser Ala Gly Asp Ile Gln
130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Asp Ile Arg Asn Tyr Leu Asn Trp
                165                 170                 175

Tyr Gln Gln Lys Pro Gly Lys Ala Pro Lys Leu Leu Ile Tyr Tyr Thr
            180                 185                 190

Ser Arg Leu Glu Ser Gly Val Pro Ser Arg Phe Ser Gly Ser Gly Ser
        195                 200                 205

Gly Thr Asp Tyr Thr Leu Thr Ile Ser Ser Leu Gln Pro Glu Asp Phe
    210                 215                 220

Ala Thr Tyr Tyr Cys Gln Gln Gly Asn Thr Leu Pro Trp Thr Phe Gly
225                 230                 235                 240

Cys Gly Thr Lys Val Glu Ile Lys
                245

<210> SEQ ID NO 49
<211> LENGTH: 480
<212> TYPE: PRT
<213> ORGANISM: Artificial
<220> FEATURE:
<223> OTHER INFORMATION: CH1 containing chain of Tb535c

<400> SEQUENCE: 49

Glu Val Gln Leu Gln Gln Ser Gly Pro Asp Leu Val Lys Pro Gly Ala
  1               5                  10                  15

Ser Val Lys Ile Ser Cys Lys Ala Ser Gly Tyr Ser Phe Thr Gly Tyr
                 20                  25                  30

Tyr Met His Trp Val Lys Gln Ser Pro Gly Lys Gly Leu Glu Trp Ile
            35                  40                  45

Gly Arg Ile Asn Pro Asn Asn Gly Val Thr Leu Tyr Asn Gln Lys Phe
        50                  55                  60

Lys Asp Lys Ala Thr Leu Thr Val Asp Lys Ser Ser Thr Thr Ala Tyr
 65                  70                  75                  80

Met Glu Leu Arg Ser Leu Thr Ser Glu Asp Ser Ala Val Tyr Tyr Cys
                 85                  90                  95

Ala Arg Ser Thr Met Ile Thr Asn Tyr Val Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Val Glu Pro Lys Ser Cys Asp
            210                 215                 220

Lys Thr His Thr Gly Pro Gly Gly Ser Pro Gly Gln Val Gln Leu
225                 230                 235                 240

Val Gln Ser Gly Ala Glu Leu Lys Lys Pro Gly Ala Ser Val Lys Val
                245                 250                 255

Ser Cys Lys Ala Ser Gly Tyr Thr Phe Thr Arg Tyr Thr Met His Trp
            260                 265                 270

Val Arg Gln Ala Pro Gly Gln Cys Leu Glu Trp Met Gly Tyr Ile Asn
            275                 280                 285

Pro Ser Arg Gly Tyr Thr Asn Tyr Asn Gln Lys Phe Lys Asp Lys Ala
            290                 295                 300

Thr Leu Thr Ala Asp Lys Ser Ser Thr Ala Tyr Met Glu Leu Arg
305                 310                 315                 320

Ser Leu Arg Ser Asp Asp Thr Ala Val Tyr Tyr Cys Ala Arg Tyr Tyr
                325                 330                 335

Asp Asp His Tyr Ser Leu Asp Tyr Trp Gly Gln Gly Thr Leu Val Thr
            340                 345                 350

Val Ser Ala Ser Gly Gly Gly Gly Ser Gly Gly Gly Gly Ser Gly
            355                 360                 365

Gly Gly Gly Ser Ala Gly Asp Ile Gln Leu Thr Gln Ser Pro Ser Ile
370                 375                 380

Leu Ser Ala Ser Val Gly Asp Arg Val Thr Ile Thr Cys Arg Ala Ser
385                 390                 395                 400

Ser Ser Val Ser Tyr Met Asn Trp Tyr Gln Gln Lys Pro Gly Lys Ala
                405                 410                 415

Pro Lys Arg Trp Ile Tyr Asp Thr Ser Lys Val Ala Ser Gly Val Pro
            420                 425                 430

Tyr Arg Phe Ser Gly Ser Gly Ser Gly Thr Glu Tyr Thr Leu Thr Ile
            435                 440                 445

Ser Ser Met Gln Pro Glu Asp Phe Ala Thr Tyr Tyr Cys Gln Gln Trp
            450                 455                 460

Ser Ser Asn Pro Leu Thr Phe Gly Cys Gly Thr Lys Val Glu Ile Lys
465                 470                 475                 480

<210> SEQ ID NO 50
<211> LENGTH: 470
<212> TYPE: PRT
<213> ORGANISM: Artificial
<220> FEATURE:
<223> OTHER INFORMATION: CL containing chain of Tb535c

<400> SEQUENCE: 50

Ser Ile Val Met Thr Gln Thr Pro Thr Ser Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
            35                  40                  45

Ser Tyr Thr Ser Ser Arg Tyr Ala Gly Val Pro Asp Arg Phe Ser Gly
        50                  55                  60
```

-continued

```
Ser Gly Tyr Gly Thr Asp Phe Thr Leu Thr Ile Ser Ser Val Gln Ala
 65                  70                  75                  80

Glu Asp Ala Ala Val Tyr Phe Cys Gln Gln Asp Tyr Asn Ser Pro Pro
                 85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Pro Gly Gly Ser Pro Gly Glu Val
210                 215                 220

Gln Leu Val Gln Ser Gly Pro Asp Val Lys Pro Gly Gly Ser Val
225                 230                 235                 240

Lys Ile Ser Cys Lys Ala Ser Gly Tyr Ser Phe Thr Gly Tyr Tyr Met
                245                 250                 255

His Trp Val Lys Gln Ser Pro Gly Lys Cys Leu Glu Trp Ile Gly Arg
            260                 265                 270

Ile Asn Pro Asn Asn Gly Val Thr Leu Tyr Asn Gln Lys Phe Lys Asp
        275                 280                 285

Lys Ala Thr Leu Thr Val Asp Lys Ser Ser Thr Thr Ala Tyr Met Glu
290                 295                 300

Leu Arg Ser Leu Thr Ser Glu Asp Ser Ala Val Tyr Tyr Cys Ala Arg
305                 310                 315                 320

Ser Thr Met Ile Thr Asn Tyr Val Met Asp Tyr Trp Gly Gln Gly Thr
                325                 330                 335

Leu Val Thr Val Ser Ser Ala Ser Gly Gly Gly Gly Ser Gly Gly Gly
            340                 345                 350

Gly Ser Gly Gly Gly Ser Ala Gly Asp Ile Val Met Thr Gln Thr
        355                 360                 365

Pro Thr Ser Leu Leu Val Ser Ala Gly Asp Arg Val Thr Ile Thr Cys
    370                 375                 380

Lys Ala Ser Gln Ser Val Ser Asn Asp Val Ala Trp Tyr Gln Gln Lys
385                 390                 395                 400

Pro Gly Gln Ser Pro Lys Leu Leu Ile Ser Tyr Thr Ser Ser Arg Tyr
                405                 410                 415

Ala Gly Val Pro Asp Arg Phe Ser Gly Ser Gly Tyr Gly Thr Asp Phe
            420                 425                 430

Thr Leu Thr Ile Ser Ser Val Gln Ala Glu Asp Ala Ala Val Tyr Phe
        435                 440                 445

Cys Gln Gln Asp Tyr Asn Ser Pro Pro Thr Phe Gly Cys Gly Thr Lys
    450                 455                 460

Leu Glu Ile Lys Ser Gly
465                 470
```

-continued

```
<210> SEQ ID NO 51
<211> LENGTH: 482
<212> TYPE: PRT
<213> ORGANISM: Artificial
<220> FEATURE:
<223> OTHER INFORMATION: CH1 containing chain of Tb535h

<400> SEQUENCE: 51
```

| | | | | | | | | | | | | | | | |
|---|---|---|---|---|---|---|---|---|---|---|---|---|---|---|---|
| Gln | Val | Gln | Leu | Val | Gln | Ser | Gly | Ala | Glu | Val | Lys | Pro | Gly | Ala |
| 1 | | | | 5 | | | | | 10 | | | | | 15 |
| Ser | Val | Lys | Val | Ser | Cys | Lys | Ala | Ser | Gly | Tyr | Ser | Phe | Thr | Ser | Tyr |
| | | | 20 | | | | | 25 | | | | | 30 | | |
| Tyr | Met | His | Trp | Val | Lys | Gln | Ser | Pro | Gly | Gln | Gly | Leu | Glu | Trp | Ile |
| | | 35 | | | | | 40 | | | | | 45 | | | |
| Gly | Arg | Ile | Asn | Pro | Asn | Asn | Gly | Val | Thr | Leu | Tyr | Asn | Gln | Lys | Phe |
| 50 | | | | | 55 | | | | | 60 | | | | | |
| Lys | Asp | Arg | Val | Thr | Met | Thr | Arg | Asp | Thr | Ser | Ile | Ser | Thr | Ala | Tyr |
| 65 | | | | 70 | | | | | 75 | | | | | 80 | |
| Met | Glu | Leu | Ser | Arg | Leu | Arg | Ser | Asp | Asp | Thr | Ala | Val | Tyr | Tyr | Cys |
| | | | | 85 | | | | | 90 | | | | | 95 | |
| Ala | Arg | Ser | Thr | Met | Ile | Thr | Asn | Tyr | Val | Met | Asp | Tyr | Trp | Gly | Gln |
| | | | 100 | | | | | 105 | | | | | 110 | | |
| Gly | Thr | Leu | Val | Thr | Val | Ser | Ser | Ala | Ser | Thr | Lys | Gly | Pro | Ser | Val |
| | | 115 | | | | | 120 | | | | | 125 | | | |
| Phe | Pro | Leu | Ala | Pro | Ser | Ser | Lys | Ser | Thr | Ser | Gly | Gly | Thr | Ala | Ala |
| 130 | | | | | 135 | | | | | 140 | | | | | |
| Leu | Gly | Cys | Leu | Val | Lys | Asp | Tyr | Phe | Pro | Glu | Pro | Val | Thr | Val | Ser |
| 145 | | | | | 150 | | | | | 155 | | | | | 160 |
| Trp | Asn | Ser | Gly | Ala | Leu | Thr | Ser | Gly | Val | His | Thr | Phe | Pro | Ala | Val |
| | | | | 165 | | | | | 170 | | | | | 175 | |
| Leu | Gln | Ser | Ser | Gly | Leu | Tyr | Ser | Leu | Ser | Ser | Val | Val | Thr | Val | Pro |
| | | | 180 | | | | | 185 | | | | | 190 | | |
| Ser | Ser | Ser | Leu | Gly | Thr | Gln | Thr | Tyr | Ile | Cys | Asn | Val | Asn | His | Lys |
| | | 195 | | | | | 200 | | | | | 205 | | | |
| Pro | Ser | Asn | Thr | Lys | Val | Asp | Lys | Lys | Val | Glu | Pro | Lys | Ser | Cys | Asp |
| 210 | | | | | 215 | | | | | 220 | | | | | |
| Lys | Thr | His | Thr | Gly | Pro | Gly | Gly | Ser | Pro | Gly | Gln | Val | Gln | Leu |
| 225 | | | | | 230 | | | | | 235 | | | | | 240 |
| Val | Gln | Ser | Gly | Ala | Glu | Leu | Lys | Lys | Pro | Gly | Ala | Ser | Val | Lys | Val |
| | | | | 245 | | | | | 250 | | | | | 255 | |
| Ser | Cys | Lys | Ala | Ser | Gly | Tyr | Thr | Phe | Thr | Arg | Tyr | Thr | Met | His | Trp |
| | | | 260 | | | | | 265 | | | | | 270 | | |
| Val | Arg | Gln | Ala | Pro | Gly | Gln | Cys | Leu | Glu | Trp | Met | Gly | Tyr | Ile | Asn |
| | | 275 | | | | | 280 | | | | | 285 | | | |
| Pro | Ser | Arg | Gly | Tyr | Thr | Asn | Tyr | Asn | Gln | Lys | Phe | Lys | Asp | Lys | Ala |
| 290 | | | | | 295 | | | | | 300 | | | | | |
| Thr | Leu | Thr | Ala | Asp | Lys | Ser | Ser | Thr | Ala | Tyr | Met | Glu | Leu | Arg |
| 305 | | | | | 310 | | | | | 315 | | | | | 320 |
| Ser | Leu | Arg | Ser | Asp | Asp | Thr | Ala | Val | Tyr | Tyr | Cys | Ala | Arg | Tyr | Tyr |
| | | | | 325 | | | | | 330 | | | | | 335 | |
| Asp | Asp | His | Tyr | Ser | Leu | Asp | Tyr | Trp | Gly | Gln | Gly | Thr | Leu | Val | Thr |
| | | | 340 | | | | | 345 | | | | | 350 | | |
| Val | Ser | Ser | Ala | Ser | Gly | Gly | Gly | Gly | Ser | Gly | Gly | Gly | Ser | Gly |
| | | 355 | | | | | 360 | | | | | 365 | | | |
| Gly | Gly | Gly | Ser | Ala | Gly | Asp | Ile | Gln | Leu | Thr | Gln | Ser | Pro | Ser | Ile |

```
                    370                 375                 380
Leu Ser Ala Ser Val Gly Asp Arg Val Thr Ile Thr Cys Arg Ala Ser
385                 390                 395                 400

Ser Ser Val Ser Tyr Met Asn Trp Tyr Gln Gln Lys Pro Gly Lys Ala
                405                 410                 415

Pro Lys Arg Trp Ile Tyr Asp Thr Ser Lys Val Ala Ser Gly Val Pro
                420                 425                 430

Tyr Arg Phe Ser Gly Ser Gly Ser Gly Thr Glu Tyr Thr Leu Thr Ile
                435                 440                 445

Ser Ser Met Gln Pro Glu Asp Phe Ala Thr Tyr Tyr Cys Gln Gln Trp
                450                 455                 460

Ser Ser Asn Pro Leu Thr Phe Gly Cys Gly Thr Lys Val Glu Ile Lys
465                 470                 475                 480

Ser Gly

<210> SEQ ID NO 52
<211> LENGTH: 470
<212> TYPE: PRT
<213> ORGANISM: Artificial
<220> FEATURE:
<223> OTHER INFORMATION: CL containing chain of Tb535h

<400> SEQUENCE: 52

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asn Asp
                20                  25                  30

Val Ala Trp Tyr Gln Gln Lys Pro Gly Gln Pro Pro Lys Leu Leu Ile
            35                  40                  45

Tyr Tyr Thr Ser Ser Arg Tyr Ala Gly Val Pro Asp Arg Phe Ser Gly
        50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Asp Tyr Asn Ser Pro Pro
                85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Pro Gly Gly Ser Pro Gly Gln Val
    210                 215                 220

Gln Leu Val Gln Ser Gly Ala Glu Val Lys Lys Pro Gly Ala Ser Val
225                 230                 235                 240

Lys Val Ser Cys Lys Ala Ser Gly Tyr Ser Phe Thr Ser Tyr Tyr Met
                245                 250                 255
```

-continued

```
His Trp Val Lys Gln Ser Pro Gly Gln Cys Leu Glu Trp Ile Gly Arg
            260                 265                 270

Ile Asn Pro Asn Asn Gly Val Thr Leu Tyr Asn Gln Lys Phe Lys Asp
            275                 280                 285

Arg Val Thr Met Thr Arg Asp Thr Ser Ile Ser Thr Ala Tyr Met Glu
    290                 295                 300

Leu Ser Arg Leu Arg Ser Asp Asp Thr Ala Val Tyr Tyr Cys Ala Arg
305                 310                 315                 320

Ser Thr Met Ile Thr Asn Tyr Val Met Asp Tyr Trp Gly Gln Gly Thr
                325                 330                 335

Leu Val Thr Val Ser Ser Ala Ser Gly Gly Gly Gly Ser Gly Gly Gly
            340                 345                 350

Gly Ser Gly Gly Gly Gly Ser Ala Gly Asp Ile Val Met Thr Gln Ser
                355                 360                 365

Pro Asp Ser Leu Ala Val Ser Leu Gly Glu Arg Ala Thr Ile Asn Cys
            370                 375                 380

Lys Ala Ser Gln Ser Val Ser Asn Asp Val Ala Trp Tyr Gln Gln Lys
385                 390                 395                 400

Pro Gly Gln Pro Pro Lys Leu Leu Ile Tyr Tyr Thr Ser Ser Arg Tyr
                405                 410                 415

Ala Gly Val Pro Asp Arg Phe Ser Gly Ser Gly Ser Gly Thr Asp Phe
            420                 425                 430

Thr Leu Thr Ile Ser Ser Leu Gln Ala Glu Asp Val Ala Val Tyr Tyr
            435                 440                 445

Cys Gln Gln Asp Tyr Asn Ser Pro Pro Thr Phe Gly Cys Gly Thr Lys
    450                 455                 460

Leu Glu Ile Lys Ser Gly
465                 470

<210> SEQ ID NO 53
<211> LENGTH: 5
<212> TYPE: PRT
<213> ORGANISM: Artificial sequence
<220> FEATURE:
<223> OTHER INFORMATION: synthetic sequence

<400> SEQUENCE: 53

Ser Tyr Tyr Met His
1               5

<210> SEQ ID NO 54
<211> LENGTH: 17
<212> TYPE: PRT
<213> ORGANISM: Artificial sequence
<220> FEATURE:
<223> OTHER INFORMATION: synthetic sequence

<400> SEQUENCE: 54

Arg Ile Asn Pro Asn Asn Gly Val Thr Leu Tyr Asn Gln Lys Phe Lys
1               5                   10                  15

Asp

<210> SEQ ID NO 55
<211> LENGTH: 11
<212> TYPE: PRT
<213> ORGANISM: Artificial sequence
<220> FEATURE:
<223> OTHER INFORMATION: synthetic sequence
```

```
<400> SEQUENCE: 55

Ser Thr Met Ile Thr Asn Tyr Val Met Asp Tyr
1               5                   10

<210> SEQ ID NO 56
<211> LENGTH: 11
<212> TYPE: PRT
<213> ORGANISM: Artificial sequence
<220> FEATURE:
<223> OTHER INFORMATION: synthetic sequence

<400> SEQUENCE: 56

Ser Gly Tyr Thr Phe Thr Arg Tyr Thr Met His
1               5                   10

<210> SEQ ID NO 57
<211> LENGTH: 17
<212> TYPE: PRT
<213> ORGANISM: Artificial sequence
<220> FEATURE:
<223> OTHER INFORMATION: synthetic sequence

<400> SEQUENCE: 57

Tyr Ile Asn Pro Ser Arg Gly Tyr Thr Asn Tyr Asn Gln Lys Phe Lys
1               5                   10                  15

Asp

<210> SEQ ID NO 58
<211> LENGTH: 8
<212> TYPE: PRT
<213> ORGANISM: Artificial sequence
<220> FEATURE:
<223> OTHER INFORMATION: synthetic sequence

<400> SEQUENCE: 58

Tyr Tyr Asp Asp His Tyr Ser Leu
1               5

<210> SEQ ID NO 59
<211> LENGTH: 10
<212> TYPE: PRT
<213> ORGANISM: Artificial sequence
<220> FEATURE:
<223> OTHER INFORMATION: synthetic sequence

<400> SEQUENCE: 59

Arg Ala Ser Ser Ser Val Ser Tyr Met Asn
1               5                   10

<210> SEQ ID NO 60
<211> LENGTH: 7
<212> TYPE: PRT
<213> ORGANISM: Artificial sequence
<220> FEATURE:
<223> OTHER INFORMATION: synthetic sequence

<400> SEQUENCE: 60

Asp Thr Ser Lys Val Ala Ser
1               5

<210> SEQ ID NO 61
<211> LENGTH: 8
<212> TYPE: PRT
<213> ORGANISM: Artificial sequence
<220> FEATURE:
<223> OTHER INFORMATION: synthetic sequence
```

```
<400> SEQUENCE: 61

Gln Gln Trp Ser Ser Asn Pro Leu
1               5

<210> SEQ ID NO 62
<211> LENGTH: 11
<212> TYPE: PRT
<213> ORGANISM: Artificial sequence
<220> FEATURE:
<223> OTHER INFORMATION: synthetic sequence

<400> SEQUENCE: 62

Lys Ala Ser Gln Ser Val Ser Asn Asp Val Ala
1               5                   10

<210> SEQ ID NO 63
<211> LENGTH: 7
<212> TYPE: PRT
<213> ORGANISM: Artificial sequence
<220> FEATURE:
<223> OTHER INFORMATION: synthetic sequence

<400> SEQUENCE: 63

Tyr Thr Ser Ser Arg Tyr Ala
1               5

<210> SEQ ID NO 64
<211> LENGTH: 9
<212> TYPE: PRT
<213> ORGANISM: Artificial sequence
<220> FEATURE:
<223> OTHER INFORMATION: synthetic sequence

<400> SEQUENCE: 64

Gln Gln Asp Tyr Asn Ser Pro Pro Thr
1               5
```

FUSION PROTEIN COMPRISING THREE BINDING DOMAINS TO 5T4 AND CD3

CROSS REFERENCE TO RELATED APPLICATIONS

The present application is the 35 U.S.C. 371 National Stage of international Application. Number PCT/EP2015/080795, filed Dec. 21, 2015, which claims priority from European patent application 14199493.9, filed Dec. 19, 2014, the contents of which are incorporated herein by reference.

SEQUENCE LISTING SUBMISSION VIA EFS-WEB

A computer readable text file, entitled "031902-5027-US-Sequence-Listing.txt", created on or about Jun. 10, 2017, with a file size of about 76 KB contains the sequence listing for this application and is hereby incorporated by reference in its entirety.

The present invention relates to a bispecific binding molecule comprising three binding domains, wherein a first and/or a second binding domain are capable of binding to the extracellular 5T4 antigen and the remaining binding domain(s) is (are) capable of binding to the CD3 receptor complex on T cells.

STATE OF THE ART

The cell surface antigen defined by monoclonal antibody 5T4 is a 72-kD glycoprotein that is expressed by all types of trophoblasts as early as 9 weeks of development. In adult tissues, the 5T4 expression is limited to a few specialized epithelial cell types but not detected in adult liver, lung, bronchus, heart, testis, ovary, brain or muscle. The antigen is selectively expressed by diverse tumour cell lines, including those of developmental origin. The molecular characteristics, the relatively restricted normal tissue distribution and expression by certain tumour cell types make this antigen worthy for use as a diagnostic marker of malignancy (Hole & Stern, Br J Cancer. (1988) 57(3), 239-46). There is clear evidence for the involvement of 5T4 in cancer and cancer progression. High levels of 5T4 expression on the surface of cancer cells have been shown for ovarian cancer (Wrigley E, McGown A T, Rennison J, et al. 5T4 oncofetal antigen expression in ovarian carcinoma. Int J Gynecol Cancer. 1995; 5:269-274), colon cancer (Starzynska T, Marsh P J, Schofield P F, Roberts S A, Myers K A, Stern P L. Prognostic significance of 5T4 oncofetal antigen expression in colorectal carcinoma. Br J Cancer. 1994; 69:899-902), cancer of the cervix (Jones H, Roberts G, Hole N, McDicken I W, Stern P. Investigation of expression of 5T4 antigen in cervical cancer. Br J Cancer. 1990; 6:69-100), gastric cancer (Starzynska T, Rahi V, Stern P L. The expression of 5T4 antigen in colorectal and gastric carcinoma. Br J Cancer. 1992; 66:867-869 and above) and lung cancer (Forsberg G, Ohlsson L, Brodin T, et al. Therapy of human non-small-cell lung carcinoma using antibody targeting of modified superantigen. Br J Cancer. 2001; 85:129-136.). An association with disease progression, namely metastasis, was also demonstrated (Mulder W M, Stern P L, Stukart M J, et al. Low intercellular adhesion molecule 1 and high 5T4 expression on tumor cells correlate with reduced disease-free survival in colorectal carcinoma patients. Clin Cancer. 1997; 3:1923-1930 and Starzynska T, Wiechowska-Kozlowska A, Marlicz K, et al. 5T4 oncofetal antigen in gastric carcinoma and its clinical significance. Eur J Gastroenterol Hepatol. 1998; 10:479-484. and Naganuma H, Kono K, Mori Y, et al. Oncofetal antigen 5T4 expression as a prognostic factor in patients with gastric cancer. Anticancer Res. 2002; 22:1033-1038). Since expression of 5T4 on normal tissues in contrast to cancerous lesions is restricted (AN A, Langdon J, Stern P L, Partidge M. The pattern of expression of 5T4 oncofoetal antigen on normal, dysplastic and malignant oral mucosa. Oral Oncol. 2001; 37:57-64), 5T4 has been suggested as a suitable target antigen for targeted cancer therapy (Woods A M, Wang W W, Shaw D M, et al. Characterization of the murine 5T4 oncofoetal antigen: a target for immunotherapy in cancer. Biochem J. 2002; 366:353-365 and Hole N, Stern P L. Isolation and characterization of 5T4, A tumor-associated antigen. Int J Cancer. 1990; 45:179-184).

Antibody-based cancer therapies require a target antigen firmly bound to the surface of cancer cells in order to be active. By binding to the surface target, the antibody can directly or indirectly deliver a deadly signal to the cancer cell. As required for an ideal treatment scenario, the target antigen 5T4 is abundantly present and accessible on specific cancer cells and is absent, shielded or much less abundant on normal cells. Yet, while the 5T4 antigen was identified as an oncology target more than 20 years ago, no anti-5T4 immunotherapy has been approved for treating cancer. Accordingly, there is a clear need for an effective therapeutic targeting this antigen.

It is known in the field to provide for antibody-based therapy in the form of a bispecific molecule binding with one domain to cytotoxic cells, i.e. cytotoxic T cells, and with a second binding domain to 5T4 on the surface of tumor cells. More specific, in WO2013041687 a bispecific molecule is described comprising a first and a second binding domain, (a) wherein the first binding domain is capable of binding to the epitope cluster 4 of 5T4; and (b) wherein the second binding domain is capable of binding to the CD3 receptor complex on T cells.

Fusion proteins of two identical or different proteins or peptides to each of the chains of an antigen binding arm of an antibody, called Fab, or derivatives thereof, are known. In its most traditional meaning, a Fab is a heterodimer between an Fd chain comprising a VH and a CH1 antibody domain, and an L-chain comprising a VL and CL antibody domain. The variable domains VH and VL can be derived from different species or antibody subclasses. Also the constant domains CH1 and CL can be derived from different species and subclasses. The fusion protein takes advantage of the CH1:CL heterodimer interaction to heterodimerize the Fab-fusion protein. WO9937791 (multipurpose antibody derivatives) teaches the use of a Fab in a traditional conformation. The VH-CH1:VL-CL heterodimer is extended C-terminal and/or N-terminal with a second and third function, or even with a fourth and fifth function. The extended functions are encoded in peptide, protein or protein parts or derivatives. WO9937791 teaches the use of fusions with a VH heavy chain variable domain followed by a CH1 heavy chain constant domain-1 to form a heterodimer with fusions to the VL variable light antibody domain followed by a CL constant light antibody domain. The VH-CH1: VL-CL (or written as VHCH1:VLCL) heterodimer can be extended with up to four peptide or protein fusions.

SUMMARY OF THE INVENTION

The present invention relates to a bispecific binding molecule (further referred to as: 'fusion protein' or "Tribody fusion protein" or "Tb-5T4 fusion protein") comprising three binding domains, wherein a first and/or a second binding domain are capable of binding to the extracellular 5T4 antigen and the remaining binding domain(s) is (are) capable of binding to the CD3 receptor complex on T cells. Moreover, the invention relates to a nucleic acid sequence encoding fusion protein, a vector comprising said nucleic acid sequence and a host cell transformed or transfected with said vector. Furthermore, the invention relates to a process for the production of the fusion protein of the invention, a medical use of said fusion protein and a kit comprising said fusion protein.

DETAILED DESCRIPTION OF THE INVENTION

Throughout this disclosure, various publications, patents and published patent specifications are referenced by an identifying citation. The disclosures of these publications, patents and published patent specifications are hereby incorporated by reference into the present disclosure to describe more fully the state of the art to which this invention pertains.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

The term "binding domain" characterizes in connection with the present invention a domain of a polypeptide which specifically binds/interacts with a given target epitope (capable of binding to/interacting with a given target epitope). An "epitope" is antigenic and thus the term epitope is sometimes also referred to herein as "antigenic structure" or "antigenic determinant". Thus, the binding domain is an "antigen-interaction-site". The term "antigen-interaction-site" defines, in accordance with the present invention, a motif of a polypeptide, which is able to specifically interact with a specific antigen or a specific group of antigens, e.g. the identical antigen in different species. Said binding/interaction is also understood to define a "specific recognition". In one example, said polypeptide which specifically binds/interacts with a given target epitope is an antibody and said domain is a VH and/or VL region or domain of an antibody.

The term "epitope" refers to a site on an antigen to which a binding domain, such as an antibody or immunoglobulin or derivative of an antibody of immunoglobulin, specifically binds. Epitopes can be formed both from contiguous amino acids or non-contiguous amino acids juxtaposed by tertiary folding of a protein. A "linear epitope" is an epitope where an amino acid primary sequence comprises the epitope recognized. A linear epitope typically includes at least 3, and more usually, at least 5, for example, about 8 to about 10 amino acids in a unique sequence.

A "conformational epitope", in contrast to a linear epitope, is an epitope wherein the primary sequence of the amino acids comprising the epitope is not the sole defining component of the epitope recognized (e.g., an epitope wherein the primary sequence of amino acids is not necessarily recognized by the antibody defining the epitope). Typically a conformational epitope comprises an increased number of amino acids relative to a linear epitope. With regard to recognition of conformational epitopes, the binding domain recognizes a 3-dimensional structure of the antigen, preferably a peptide or protein or fragment thereof (in the context of the present invention, the antigen is for one of the binding domains the 5T4 protein). For example, when a protein molecule folds to form a three dimensional structure, certain amino acids and/or the polypeptide backbone forming the conformational epitope become juxtaposed enabling the antibody to recognize the epitope. Methods of determining conformation of epitopes include but are not limited to, for example, x-ray crystallography 2-dimensional nuclear magnetic resonance spectroscopy and site-directed spin labelling and electron paramagnetic resonance spectroscopy.

The terms "specifically binding/interacting", "specifically recognizing", "directed to" and "reacting with" mean in accordance with this invention that a binding domain is capable of specifically interacting with and/or binding to at least two, preferably at least three, more preferably at least four amino acids of an epitope. Such binding may be exemplified by the specificity of a "lock-and-key-principle". As used herein, the terms "specifically interacting", "specifically binding" or "specifically binds" mean that a binding domain exhibits appreciable affinity for a particular protein or antigen and, generally, does not exhibit significant cross-reactivity with other proteins or antigens. "Appreciable" or preferred binding includes binding with an affinity of $10^{-6}$ M (KD) or higher. Preferably, binding is considered specific when binding affinity is about $10^{-11}$ to $10^{-8}$ M, preferably of about $10^{-11}$ to $10^{-9}$ M. If necessary, nonspecific binding can be reduced without substantially affecting specific binding by varying the binding conditions. Whether binding domains specifically react or bind with a target can be tested readily by, inter alia, comparing the reaction of one of said binding domains with a target protein or antigen with the reaction of said binding domains with other proteins or antigens.

Specific binding is believed to be effected by specific motifs in the amino acid sequence of the binding domain and the antigen. Thus, binding is achieved as a result of their primary, secondary or tertiary structure as well as the result of secondary modifications of said structures. The specific interaction of the antigen-interaction-site with its specific antigen may result as well in a simple binding of said site to the antigen. Moreover, the specific interaction of the antigen-interaction-site with its specific antigen may alternatively result in the initiation of a signal, e.g. due to the induction of a change of the conformation of the antigen, an oligomerization of the antigen, etc. In one example, a binding domain is an antibody.

The term "does not essentially bind" means that a binding domain of the fusion protein of the present invention does not bind another protein, i.e., shows a cross-reactivity of less than 30%, preferably 20%, more preferably 10%, particularly preferably less than 9, 8, 7, 6 or 5% with another protein.

The terms "cross-species specificity", "cross-species recognition" and "interspecies specificity" as used herein denote a binding domain's ability to bind to the same target molecule in humans and non-human species, preferably in primate species. Thus, "cross-species specificity" or "interspecies specificity" describes interspecies reactivity to the same molecule X (e.g., 5T4 or CD3s) expressed in different species, but not to a molecule other than X (e.g., 5T4 or CD3s).

Proteins (including fragments thereof, preferably biologically active fragments, and peptides, usually having less than 30 amino acids) comprise one or more amino acids coupled to each other via a covalent peptide bond (resulting in a chain of amino acids). The term "polypeptide" as used herein describes a group of molecules, which consist of or comprise more than 30 amino acids. Polypeptides may further form multimers such as dimers, trimers and higher oligomers, i.e. consisting of or comprising more than one polypeptide molecule. Polypeptide molecules forming such dimers, trimers etc. may be identical or non-identical. The corresponding higher order structures of such multimers are, consequently, termed homo- or heterodimers, homo- or heterotrimers etc. An example for a hereteromultimer is an antibody molecule, which, in its naturally occurring form, consists of two or comprise identical light polypeptide chains and two identical heavy polypeptide chains. The terms "polypeptide" and "protein" also refer to naturally modified polypeptides/proteins wherein the modification is effected e.g. by post-translational modifications like glycosylation, acetylation, phosphorylation and the like. Such modifications are well known in the art.

As noted herein above, in one aspect, the first and/or second binding domain of the fusion protein is capable of binding to human and Callithrix jacchus, Saguinus oedipus or Saimiri sciureus 5T4 and/or the remaining binding domain(s) is (are) capable of binding to human and Callithrix jacchus, Saguinus Oedipus or Saimiri sciureus CD3 epsilon. According to this embodiment, all three binding domains of the fusion protein of the invention are cross-species specific for members of the mammalian order of primates.

In one embodiment, the first or the second or the third binding domain is derived from an antibody. In another embodiment, all binding domains are derived from an antibody. The definition of the term "antibody" includes embodiments such as monoclonal, chimeric, single chain, humanized and human antibodies, as well as antibody fragments, like, inter alia, Fab fragments. Antibody fragments or derivatives further comprise F(ab')2, Fv, scFv fragments or single domain antibodies such as domain antibodies or nanobodies, single variable domain antibodies or immunoglobulin single variable domain comprising merely one variable domain, which might be VHH, VH or VL, that specifically bind an antigen or epitope independently of other V regions or domains; see, for example, Harlow and Lane (1988) and (1999), loc. cit; Kontermann and Dubel, Antibody Engineering, Springer, 2nd ed. 2010 and Little, Recombinant Antibodies for Immunotherapy, Cambridge University Press 2009. Such immunoglobulin single variable domain encompasses not only an isolated antibody single variable domain polypeptide, but also larger polypeptides that comprise one or more monomers of an antibody single variable domain polypeptide sequence.

Various procedures are known in the art and may be used for the production of such antibodies and/or fragments. Thus, (antibody) derivatives can be produced by peptidomimetics. Further, techniques described for the production of single chain antibodies (see, inter alia, U.S. Pat. No. 4,946,778, Kontermann and Dubel (2010), loc. cit. and Little (2009), loc. cit.) can be adapted to produce single chain antibodies specific for elected polypeptide(s). Also, transgenic animals may be used to express humanized antibodies specific for polypeptides and fusion proteins of this invention. For the preparation of monoclonal antibodies, any technique, providing antibodies produced by continuous cell line cultures can be used. Examples for such techniques include the hybridoma technique (Kohler and Milstein Nature 256 (1975), 495-497), the trioma technique, the human B-cell hybridoma technique (Kozbor, Immunology Today 4 (1983), 72) and the EBV-hybridoma technique to produce human monoclonal antibodies (Cole et al., Monoclonal Antibodies and Cancer Therapy, Alan R. Liss, Inc. (1985), 77-96). Surface plasmon resonance as employed in the BIAcore system can be used to increase the efficiency of phage antibodies which bind to an epitope of a target polypeptide, such as CD3 epsilon (Schier, Human Antibodies Hybridomas 7 (1996), 97-105; Malmborg, J. Immunol. Methods 183 (1995), 7-13). It is also envisaged in the context of this invention that the term "antibody" comprises antibody constructs, which may be expressed in a host as described herein below, e.g. antibody constructs which may be transfected and/or transduced via, inter alia, viruses or plasmid vectors.

Furthermore, the term "antibody" as employed in the invention also relates to derivatives or variants of the antibodies described herein which display the same or similar specificity as the described antibodies. A similar specific is a specificity which at least 30%, at least 40% at least 50% at least 60% at least 70% at least 80% at least 90% at least 95%, at least 105% at least 110% at least 120% at least 130% at least 140% at least 150% at least 160% of the specificity of the initial/control antibody the variants or derivatives derive from. Examples of "antibody variants" include humanized variants of non-human antibodies, "affinity matured" antibodies (see, e.g. Hawkins et al. J. Mol. Biol. 254, 889-896 (1992) and Lowman et al., Biochemistry 30, 10832-10837 (1991)) and antibody mutants with altered effector function (s) (see, e.g., U.S. Pat. No. 5,648,260, Kontermann and Dubel (2010), loc. cit. and Little (2009), loc. cit).

The terms "antigen-binding domain", "antigen-binding fragment", "antibody binding domain" and "antibody binding region" when used herein refer to a part of an antibody molecule that comprises amino acids responsible for the specific binding between antibody and antigen. The part of the antigen that is specifically recognized and bound by the antibody is referred to as the "epitope" as described herein above. As mentioned above, an antigen-binding domain may typically comprise an antibody light chain variable region (VL) and an antibody heavy chain variable region (VH); however, it does not have to comprise both. Fd fragments, for example, have two VH regions and often retain some antigen-binding function of the intact antigen-binding domain. Examples of antigen-binding fragments of an antibody include (1) a Fab fragment, a monovalent fragment having the VL, VH, CL and CH1 domains; (2) a F(ab')2 fragment, a bivalent fragment having two Fab fragments linked by a disulfide bridge at the hinge region; (3) a Fd fragment having the two VH and CH 1 domains; (4) a Fv fragment having the VL and VH domains of a single arm of an antibody, (5) a dAb fragment (Ward et al., (1989) Nature 341:544-546), which has a VH domain; (6) an isolated complementarity determining region (CDR), and (7) a single chain Fv (scFv). Although the two domains of the Fv fragment, VL and VH are coded for by separate genes, they can be joined, using recombinant methods, by a synthetic linker that enables them to be made as a single protein chain in which the VL and VH regions pair to form monovalent molecules (known as single chain Fv (scFv); see e.g., Huston et al. (1988) Proc. Natl. Acad. Sci USA 85:5879-5883). These antibody fragments are obtained using conventional techniques known to those with skill in the art, and the fragments are evaluated for function in the same manner as are intact antibodies. The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352: 624-628 (1991) and Marks et al., J. Mol. Biol., 222: 581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain (s) is (are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81: 6851-6855 (1984)). Chimeric antibodies of interest herein include "primitized" antibodies comprising variable domain antigen-binding sequences derived from a non-human primate (e.g., Old World Monkey, Ape etc.) and human constant region sequences. "Humanized" forms of non-human (e.g., murine) antibodies are chimeric immunoglobulins, immunoglobulin chains or fragments thereof (such as Fv, Fab, Fab', F (ab') 2 or other antigen-binding subsequences of antibodies) of mostly human sequences, which contain minimal sequence derived from non-human immunoglobulin. For the most part, humanized antibodies are human immunoglobulins (recipient antibody) in which residues from a hypervariable region (also CDR) of the recipient are replaced by residues from a hypervariable region of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, "humanized antibodies" as used herein may also comprise residues which are found neither in the recipient antibody nor the donor antibody. These modifications are made to further refine and optimize antibody performance. The humanized antibody optimally also will comprise at least a portion of an immunoglobulin constant region (Fc), typically that of a human immunoglobulin. For further details, see Jones et al., Nature, 321: 522-525 (1986); Reichmann et al., Nature, 332: 323-329 (1988); and Presta, Curr. Op. Struct. Biol., 2: 593-596 (1992).

The term "human antibody" includes antibodies having variable and constant regions corresponding substantially to human germline immunoglobulin sequences known in the art, including, for example, those described by Kabat et al. (See Kabat, et al. (1991) loc. cit). The human antibodies of the invention may include amino acid residues not encoded by human germline immunoglobulin sequences (e.g., mutations introduced by random or site-specific mutagenesis in vitro or by somatic mutation in vivo), for example in the CDRs, and in particular, CDR3. The human antibody can have at least one, two, three, four, five, or more positions replaced with an amino acid residue that is not encoded by the human germline immunoglobulin sequence.

As used herein, "in vitro generated antibody" refers to an antibody where all or part of the variable region (e.g., at least one CDR) is generated in a non-immune cell selection (e.g., an in vitro phage display, protein chip or any other method in which candidate sequences can be tested for their ability to bind to an antigen). This term thus preferably excludes sequences generated by genomic rearrangement in an immune cell. A "bispecific" or A "functional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, Clin. Exp. Immunol. 79:315-321 (1990). Numerous methods known to those skilled in the art are available for obtaining antibodies or antigen-binding fragments thereof. For example, antibodies can be produced using recombinant DNA methods (U.S. Pat. No. 4,816,567). Monoclonal antibodies may also be produced by generation of hybridomas (see e.g., Kohler and Milstein (1975) Nature, 256: 495-499) in accordance with known methods. Hybridomas formed in this manner are then screened using standard methods, such as enzyme-linked immunosorbent assay (ELISA) and surface plasmon resonance (BIACORE™) analysis, to identify one or more hybridomas that produce an antibody that specifically binds with a specified antigen. Any form of the specified antigen may be used as the immunogen, e.g., recombinant antigen, naturally occurring forms, any variants or fragments thereof, as well as antigenic peptide thereof.

One exemplary method of making antibodies includes screening protein expression libraries, e.g., phage or ribosome display libraries. Phage display is described, for example, in Ladner et al., U.S. Pat. No. 5,223,409; Smith (1985) Science 228:1315-1317; Clackson et al. (1991) Nature, 352: 624-628.

Humanized antibodies or fragments thereof can be generated by replacing sequences of the Fv variable domain that are not directly involved in antigen binding with equivalent sequences from human Fv variable domains. Exemplary methods for generating humanized antibodies or fragments thereof are provided by Morrison (1985) Science 229:1202-1207; by Oi et al. (1986) BioTechniques 4:214; and by U.S. Pat. Nos. 5,585,089; 5,693,761; 5,693,762; 5,859,205; and 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

A humanized antibody can be optimized by the introduction of conservative substitutions, consensus sequence substitutions, germline substitutions and/or back mutations. Such altered immunoglobulin molecules can be made by any of several techniques known in the art, (e.g., Teng et al., Proc. Natl. Acad. Sci. U.S.A., 80: 7308-7312, 1983; Kozbor et al, Immunology Today, 4: 7279, 1983; Olsson et al., Meth. Enzymol., 92: 3-16, 1982, and may be made according to the teachings of EP 239 400). An antibody or fragment thereof may also be modified by specific deletion of human T cell epitopes or "deimmunization" by the methods disclosed in WO 98/52976 and WO 00/34317. Briefly, the heavy and light chain variable domains of an antibody can be analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the VH and VL sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable domains, or preferably, by single amino acid substitutions. In this context, small means one, two, three, four, five or six amino acid residues. Typically, conservative substitutions are made. Often, but not exclusively, an amino acid common to a position in human germline antibody sequences may be used. Human germline sequences, e.g., are disclosed in Tomlinson, et al. (1992) J. Mol. Biol. 227:776-798; J. Mol. Biol. 227:776-798; Cook, G. P. et al. (1995) Immunol. Today Vol. 16 (5): 237-242; and Tomlinson et al. (1995) EMBO J. 14: 14:4628-4638. The V BASE directory provides a comprehensive directory of human immunoglobulin variable region sequences (compiled by Tomlinson, L A. et al. MRC Centre for Protein Engineering, Cambridge, UK). These sequences can be used as a source of human sequence, e.g., for framework regions and CDRs. Consensus human framework regions can also be used, e.g., as described in U.S. Pat. No. 6,300,064. The pairing of a VH and VL together forms a single antigen-binding site, referred hereinafter to as "combined VH/VL binding domains". The CH domain most proximal to VH is designated as CH1. Each L chain is linked to an H chain by one covalent disulfide bond, while the two H chains are linked to each other by one or more disulfide bonds depending on the H chain isotype. The VH and VL domains consist of four regions of relatively conserved sequences called framework regions (FR1, FR2, FR3, and FR4), which form a scaffold for three regions of hypervariable sequences (complementarity determining regions, CDRs). The CDRs contain most of the residues responsible for specific interactions of the antibody with the antigen. CDRs are referred to as CDR 1, CDR2, and CDR3. Accordingly, CDR constituents on the heavy chain are referred to as H1, H2, and H3, while CDR constituents on the light chain are referred to as L1, L2, and L3.

The term "variable" refers to the portions of the immunoglobulin domains that exhibit variability in their sequence and that are involved in determining the specificity and binding affinity of a particular antibody (i.e., the "variable domain(s)"). Variability is not evenly distributed throughout the variable domains of antibodies; it is concentrated in sub-domains of each of the heavy and light chain variable regions. These sub-domains are called "hypervariable" regions or "complementarity determining regions" (CDRs). The more conserved (i.e., non-hypervariable) portions of the variable domains are called the "framework" regions (FRM). The variable domains of naturally occurring heavy and light chains each comprise four FRM regions, largely adopting a β-sheet configuration, connected by three hypervariable regions, which form loops connecting, and in some cases forming part of, the β-sheet structure. The hypervariable regions in each chain are held together in close proximity by the FRM and, with the hypervariable regions from the other chain, contribute to the formation of the antigen-binding site (see Kabat et al., loc. cit). The constant domains are not directly involved in antigen binding, but exhibit various effector functions, such as, for example, antibody-dependent, cell-mediated cytotoxicity and complement activation.

The term "amino acid" or "amino acid residue" typically refers to an amino acid having its art recognized definition such as an amino acid selected from the group consisting of: alanine (Ala or A); arginine (Arg or R); asparagine (Asn or N); aspartic acid (Asp or D); cysteine (Cys or C); glutamine (Gin or Q); glutamic acid (Glu or E); glycine (Gly or G); histidine (His or H); isoleucine (He or I): leucine (Leu or L); lysine (Lys or K); methionine (Met or M); phenylalanine (Phe or F); pro line (Pro or P); serine (Ser or S); threonine (Thr or T); tryptophan (Trp or W); tyrosine (Tyr or Y); and valine (Val or V), although modified, synthetic, or rare amino acids may be used as desired. Generally, amino acids can be grouped as having a nonpolar side chain (e.g., Ala, Cys, He, Leu, Met, Phe, Pro, Val); a negatively charged side chain (e.g., Asp, Glu); a positively charged sidechain (e.g., Arg, His, Lys); or an uncharged polar side chain (e.g., Asn, Cys, Gin, Gly, His, Met, Phe, Ser, Thr, Trp, and Tyr).

The term "hypervariable region" (also known as "complementarity determining regions" or CDRs) when used herein refers to the amino acid residues of an antibody which are (usually three or four short regions of extreme sequence variability) within the V-region domain of an immunoglobulin which form the antigen-binding site and are the main determinants of antigen specificity. There are at least two methods for identifying the CDR residues: (1) An approach based on cross-species sequence variability (i. e., Kabat et al., loc. cit); and (2) An approach based on crystallographic studies of antigen-antibody complexes (Chothia, C. et al., J. Mol. Biol. 196: 901-917 (1987)). However, to the extent that two residue identification techniques define regions of overlapping, but not identical regions, they can be combined to define a hybrid CDR. However, in general, the CDR residues are preferably identified in accordance with the so-called Kabat (numbering) system.

The current invention comprises the use of Fab (VHCH1: VLCL) or crossover-Fab (VHCL:VLCH1) or domain-Fab (V1CH1:V2CL). We will refer to Fab-derived heterodimer to comprise VHCH1:VLCL; VHCL:VLCH1 and V1CH1: V2CL based structures. In the current invention only two extensions are made to the Fab-derived and CH1:CL driven heterodimer. In a preferred configuration, each CH1 and CL comprising chain has a peptide-bond based extension. In a most preferred configuration these extensions are at the C-terminus of the CH1-comprising and the CL-comprising chains. In this position they will not influence the binding capacity of the Fab molecule and thus create a fully functional trifunctional, trivalent, bivalent bispecific, or trispecific molecule. Surprisingly, the C-terminal fusions of the current invention also increase the stability and overall melting temperature of the final fusion protein as demonstrated in FIG. 6A, 6B.

Fusion proteins of the current invention are further extended with binding or effector molecules to comprise a dual binding function towards a tumor antigen and a single immune activating function.

Fusion proteins of the current invention combine a bivalent binding towards the tumor associated antigen (TAA) 5T4, with a T-cell activating function. In the example of the Tb-5T4 Tribody family, a bivalent binding to 5T4 will be combined with a monovalent binding to CD3. The bivalent 5T4 binding increases the specificity for tumor cells overexpressing the 5T4 antigen. A bivalent binding also decreases the off-rate of the targeting complex thus stabilizing the binding in time. The monovalent binding to the T-cell CD3 avoids activation of T-cells by a bivalent CD3 binding molecule as seen with OKT3 and OKT3-derived (Fab')2 (bivalent binding Fab fragments to CD3). These molecules were known for T-cell activation followed by activation induced cell death or render the T-cells anergic, and found useful in avoiding rejection of transplanted organs. A fusion protein of current invention thus is composed of two fusion chains which form a CH1:CL driven heterodimer. In a further embodiment, a fusion protein comprising two different chains, wherein (i) one chain comprises two VH antibody binding domains, one VL antibody binding domain and one CH1 or CL antibody domain, and (ii) the other chain comprises two VL antibody binding domains, one VH antibody binding domain and one CL or CH1 antibody domain, provided that the fusion protein contains one heterodimer interaction between the CH1 antibody domain of one chain and the CL antibody domain of the other chain, characterized in that (a) one or two combined VH/VL binding domains formed within a chain are capable of binding to the extracellular 5T4 antigen; and (b) the remaining one or two combined VH/VL binding domains formed within a chain are capable of binding to the CD3 receptor complex on T cells.

A fusion protein of the current invention can be of the form or could also be defined as follows
VH(5T4)-CH1-L1-VH(CD3)-L2-VL(CD3) or
VH(5T4)-CH1-L1-VL(CD3)-L2-VH(CD3)
Combined with
VL(5T4)CL-L1-VH(5T4)-L2-VL(5T4) or
VL(5T4)CL-L1-VL(5T4)-L2-VH(5T4).
Or of the form:
VH(5T4)-CH1-L1-VH(5T4)-L2-VL(5T4) or
VH(5T4)-CH1-L1-VL(5T4)-L2-VH(5T4)
Combined with
VL(5T4)CL-L1-VH(CD3)-L2-VL(CD3) or
VL(5T4)CL-L1-VL(CD3)-L2-VH(CD3).
Or of the form:
VH(CD3)-CH1-L1-VH(5T4)-L2-VL(5T4) or
VH(CD3)-CH1-L1-VL(5T4)-L2-VH(5T4)
Combined with
VL(CD3)CL-L1-VH(5T4)-L2-VL(5T4) or
VL(CD3)CL-L1-VL(5T4)-L2-VH(5T4).
Or of the form:
VL(CD3)-CH1-L1-VH(5T4)-L2-VL(5T4) or
VL(CD3)-CH1-L1-VL(5T4)-L2-VH(5T4)
combined with
VH(CD3)CL-L1-VH(5T4)-L2-VL(5T4) or
VH(CD3)CL-L1-VL(5T4)-L2-VH(5T4)
Or based on a crossover-Fab (VHCL:VLCH1) of the form:
VL(5T4)-CH1-L1-VH(CD3)-L2-VL(CD3) or
VL(5T4)-CH1-L1-VL(CD3)-L2-VH(CD3)
Combined with
VH(5T4)CL-L1-VH(5T4)-L2-VL(5T4) or
VH(5T4)CL-L1-VL(5T4)-L2-VH(5T4).
Or:
VL(5T4)-CH1-L1-VH(5T4)-L2-VL(5T4) or
VL(5T4)-CH1-L1-VL(5T4)-L2-VH(5T4)
Combined with
VH(5T4)CL-L1-VH(CD3)-L2-VL(CD3) or
VH(5T4)CL-L1-VL(CD3)-L2-VH(CD3).
All these fusion proteins have been illustrated in FIGS. 1B and 1C.

Other encompassed Tb-5T4 fusion proteins are those where structures are based on single domain binder fusions to CH1 and CL heterodimers (dFab) (see also FIG. 1D):
V1 (5T4)CL-L1-VH(5T4)-L2-VL(5T4) or
V1 (5T4)CL-L1-VL(5T4)-L2-VH(5T4)
Where V1 is a single domain binder with specificity to 5T4
combined with
V2-CH1-L1-VH(CD3)-L2-VL(CD3) or
V2-CH1-L1-VL(CD3)-L2-VH(CD3)
where V2 is a single domain binder with a different specificity than for 5T4 or CD3 as illustrated for 2 possible combinations in (xiii) and (xvi) of FIG. 1D,
Or different form organizations of
V2-CH1-L1-VH(5T4)-L2-VL(5T4) or
V2-CH1-L1-VL(5T4)-L2-VH(5T4)
combined with
V1 (5T4)CL-L1-VH(CD3)-L2-VL(CD3) or
V1 (5T4)CL-L1-VL(CD3)-L2-VH(CD3)
where V2 is a single domain binder with a different specificity than for 5T4 or CD3 as illustrated for 2 possible combinations in (xiv) and (xvii) of FIG. 1D,
Or different form-organizations of
V1 (CD3)-CH1-L1-VH(5T4)-L2-VL(5T4) or
V1 (CD3)-CH1-L1-VL(5T4)-L2-VH(5T4)
combined with
V2-CL-L1-VH(5T4)-L2-VL(5T4) or
V2-CL-L1-VL(5T4)-L2-VH(5T4)
where V2 is a single domain binder with a different specificity than for 5T4 or CD3 as illustrated for 2 possible combinations in model (xv) and (xviii) of FIG. 1D.

In all the combinations depicted in FIG. 1D, the scFv can also be a disulfide stabilized single chain variable fragment (dsFv)

Accordingly in a preferred embodiment, a fusion protein is encompassed by the invention which is preferably as defined above. This fusion protein comprises two different chains:
a) First chain: VH(5T4)-CH1-L1-VH(CD3)-L2-VL(CD3) or
   VH(5T4)-CH1-L1-VL(CD3)-L2-VH(CD3) combined with
   Second chain: VL(5T4)CL-L1-VH(5T4)-L2-VL(5T4) or
   VL(5T4)CL-L1-VL(5T4)-L2-VH(5T4),
b) First chain: VH(5T4)-CH1-L1-VH(5T4)-L2-VL(5T4) or
   VH(5T4)-CH1-L1-VL(5T4)-L2-VH(5T4) combined with
   Second chain: VL(5T4)CL-L1-VH(CD3)-L2-VL(CD3) or
   VL(5T4)CL-L1-VL(CD3)-L2-VH(CD3),
c) First chain: VH(CD3)-CH1-L1-VH(5T4)-L2-VL(5T4) or
   VH(CD3)-CH1-L1-VL(5T4)-L2-VH(5T4) combined with
   Second chain: VL(CD3)CL-L1-VH(5T4)-L2-VL(5T4) or
   VL(CD3)CL-L1-VL(5T4)-L2-VH(5T4),
d) First chain: VL(CD3)-CH1-L1-VH(5T4)-L2-VL(5T4) or
   VL(CD3)-CH1-L1-VL(5T4)-L2-VH(5T4) combined with
   Second chain: VH(CD3)CL-L1-VH(5T4)-L2-VL(5T4) or
   VH(CD3)CL-L1-VL(5T4)-L2-VH(5T4),
e) First chain: VL(5T4)-CH1-L1-VH(CD3)-L2-VL(CD3) or
   VL(5T4)-CH1-L1-VL(CD3)-L2-VH(CD3) combined with
   Second chain: VH(5T4)CL-L1-VH(5T4)-L2-VL(5T4) or
   VH(5T4)CL-L1-VL(5T4)-L2-VH(5T4),
f) First chain: VL(5T4)-CH1-L1-VH(5T4)-L2-VL(5T4) or
   VL(5T4)-CH1-L1-VL(5T4)-L2-VH(5T4) combined with
   Second chain: VH(5T4)CL-L1-VH(CD3)-L2-VL(CD3) or
   VH(5T4)CL-L1-VL(CD3)-L2-VH(CD3).
g) First chain V1(5T4)CL-L1-VH(5T4)-L2-VL(5T4) or
   V1 (5T4)CL-L1-VL(5T4)-L2-VH(5T4) combined with
   Second chain: V2-CH1-L1-VH(CD3)-L2-VL(CD3) or
   V2-CH1-L1-VL(CD3)-L2-VH(CD3)
h) First chain: V2-CH1-L1-VH(5T4)-L2-VL(5T4) or
   V2-CH1-L1-VL(5T4)-L2-VH(5T4) combined with
   Second chain: V1(5T4)CL-L1-VH(CD3)-L2-VL(CD3) or
   V1 (5T4)CL-L1-VL(CD3)-L2-VH(CD3)
i) First chain: V1(CD3)-CH1-L1-VH(5T4)-L2-VL(5T4) or
   V1 (CD3)-CH1-L1-VL(5T4)-L2-VH(5T4) combined with
   Second chain: V2-CL-L1-VH(5T4)-L2-VL(5T4) or
   V2-CL-L1-VL(5T4)-L2-VH(5T4)
wherein VH, VL are antibody binding domains, CH1 and CL are antibody domains, and wherein the fusion protein is such that (a) one or two combined VH/VL binding domains formed within a chain are capable of binding to the extracellular 5T4 antigen; and (b) the remaining one or two combined VH/VL binding domains formed within a chain are capable of binding to the CD3 receptor complex on T cells.

In an embodiment, a Tb-5T4 fusion protein also called a fusion protein comprises fusion proteins where the CH1:CL comprising portion is binding the 5T4 antigen and each CH1-comprising and CL-comprising chain is C-terminally extended with another binding molecule. In the case where the CH1:CL comprising portion provides one 5T4 binding function, the additional fused binders will comprise at least one other 5T4 binding molecule and one other CD3-binding molecule.

The fusion protein of the current invention can be derived from a combination of V-domains as seen in normal antibodies. They can be formatted as single chain variable fragments (scFv). scFv can be in the format VH-linker-VL or in the format VL-linker-VH. Both formats can have differences in binding properties and stability. Both formats can be compared without undue burden by a person skilled in the art. The use of scFv is thought by WO8801649 (single polypeptide binding molecules) and U.S. Pat. No. 5,455,030 (Immunotherapy using single chain polypeptide binding molecules).

The scFv molecules comprise a linker molecule which have been described in the art. The art contains examples where linker sequences can be optimized for certain pairs of VH and VL. A preferred linker spans the distance between the C-terminus of the first V-domain and the N-terminus of the second V-domain. A preferred linker is also flexible enough not to disturb the folding of the variable regions. A preferred linker does not contain any antigenic antibody-epitopes and immunogenic T-cell epitopes. An example of a preferred linker connecting the two V-domains in a scFv is a 15 to 18 amino acid long peptide containing many glycines (a flexible, non-immunogenic amino acid) and serines (a flexible, low-immunogenic amino acid with higher solubility). An example of a most preferred linker known in the art is GGGGSGGGGSGGGGS or written as (GGGGS)3.

The variable domains generally do not have a stable interaction, and VH:VL dissociation constants can be as high as 10 mM. Consequently, the V-domain dimers often dissociate. A linker fusing both domains increases the chance of re-association.

One other technology is known in the art: WO9429350 (Methods of making recombinant disulphide-stabilized polypeptide fragments having binding specificity) teaches the engineering at specific sites between the VH and VL to engineer an artificial disulphide bridge. In this way a covalently stable dimer can be obtained. In the present invention, variable binding fragments will be preferred as single chain polypeptide. Since two are needed for a fusion protein such as a Tb-5T4 Tribody the single chain format avoids mispairing of V-domains and thus the variation in product and production of non-functional derivatives. However, the frequent dissociation and re-association of the VH-VL pairs may in particular cases lead to dimer formation with another fusion protein such as Tb-5T4. These products would have a possible bivalent anti-CD3 binding and thus a potential activation of T-cells even when not accumulated at the tumor target cell.

As many bispecific T-cell engagers based on scFv molecules induce off-target toxicity in the form of inflammatory cytokine production. Typical cytokines induced are IL-2, IFN-gamma and TNF-alpha. When the stimulation is high and/or the cytokine storm is not clinically controlled, it can lead to organ failure and become life threatening.

The current invention may use or uses a combination of the single chain variable domain technologies as taught in WO8801649 and the disulphide stabilization of the V-fragment as taught in WO9429350 to create a disulphide stabilized single chain variable domain (dsFv).

In order to assemble the fusion protein of the invention, variable domains forming a functional binding molecule must be selected. A suitable antibody binding to the 5T4 TAA with no described cross-reactivity in normal tissue is known as the mouse monoclonal 5T4.H8. The variable domains of 5T4.H8 are given in or are comprised in or consist of SEQ ID 01 and SEQ ID 16. A structurally more stable derivative of these sequences is given in or are comprised in or consist of SEQ ID 02 and SEQ ID 17. The murine variable domain framework region can be humanized using various methods known in the art. Examples of humanized variable domains are given in or are comprised in or consist of SEQ ID 3 through 15 (SEQ ID 3; 4; 5; 6; 7; 8; 9; 10; 11; 12; 13; 14; 15) for the VH domain and SEQ ID 18 through 25 (SEQ ID 18; 19; 20; 21; 22; 23; 24; 25) for the VL domain. Humanized framework residues are preferred for it is generally believed they are less antigenic and/or immunogenic. Therefore a preferred fusion protein such as Tb-5T4 of the invention would have a combination of a VH sequence of SEQ ID 3-15 with a VL sequence of SEQ-ID 18-25. An embodiment, therefore relates to a fusion protein such as Tb-5T4 of the invention with a combination of a VH sequence comprising one of or consisting one of a sequence having at least 60%, 70%, 80%, 90%, 95%, 97%, 98%, 99% identity with one of SEQ ID 3-15 with a VL sequence comprising one of or consisting one of a sequence having at least 60%, 70%, 80%, 90%, 95%, 97%, 98%, 99% identity with one of SEQ-ID 18-25. A functional combination can then be formatted into a disulphide stabilized single chain variable domain (dsFv) of the VH-linker-VL or the VL-linker-VH format, or grafted onto the CH1 and CL domains to create a VHCH1:VLCL Fab or a VHCL:VLCH1 crossover-Fab.

A suitable binder to the CD3 complex can be assembled in a similar way. A number of T-cell activating CD-epsilon binders are known in the art. OKT3 is a mouse monoclonal used to prevent transplantation rejection. The use of OKT3 sequences (SEQ ID 26 and SEQ ID 34 or sequences comprising these sequences or having at least 60%, 70%, 80%, 90%, 95%, 97%, 98%, 99% identity with these sequences) is taught by U.S. Pat. No. 6,750,325 (CD3 specific recombinant antibody) and WO2008079713 (Methods for the treatment of LADA and other adult-onset autoimmune diabetes using immunosuppressive monoclonal antibodies with reduced toxicity). Humanized forms of the OKT3 variable sequences are disclosed in U.S. Pat. No. 7,635,475 (Novel diabody-type bispecific antibody) and WO2005040220 (Multispecific deimmunized CD3-binders). Humanized OKT3 derived VH domain sequences are given in SEQ ID NOs 27; 28; 29 (or sequences comprising these sequences or having at least 60%, 70%, 80%, 90%, 95%, 97%, 98%, 99% identity with these sequences). Humanized OKT3 derived VL domain sequences are given in SEQ ID NOs 35; 36; 37 (or sequences comprising these sequences or having at least 60%, 70%, 80%, 90%, 95%, 97%, 98%, 99% identity with these sequences). A CD3 binding moiety based on the OKT3 variable domains to create a scFv, dsFv Fab or crossover-Fab combination can be made of SEQ ID NOs 27-29 (or sequences comprising these sequences or having at least 60%, 70%, 80%, 90%, 95%, 97%, 98%, 99% identity with one of these sequences) with SEQ ID NOs 35-37 (or sequences comprising these sequences or having at least 60%, 70%, 80%, 90%, 95%, 97%, 98%, 99% identity with one of these sequences).

Other binders to CD3 are known in the art by U.S. Pat. No. 7,728,114 (Anti-CD3 antibodies and methods of use thereof) (SEQ ID NOs 30 and 38 or sequences comprising these sequences or having at least 60%, 70%, 80%, 90%, 95%, 97%, 98%, 99% identity with these sequences); WO9404679 (Humanized antibodies and methods for making them) (SEQ ID NOs 32 and 40 or sequences comprising these sequences or having at least 60%, 70%, 80%, 90%, 95%, 97%, 98%, 99% identity with these sequences), U.S. Pat. No. 7,381,803 (Humanized antibodies against CD3) (SEQ ID NOs 33 and 40 or sequences comprising these sequences or having at least 60%, 70%, 80%, 90%, 95%, 97%, 98%, 99% identity with these sequences), or as described by Li et al (2005). "Construction and characterization of a humanized anti-human CD3 monoclonal antibody 12F6 with effective immunoregulation functions." Immunology 116(4): 487-498. (SEQ ID NOs 31 and 39 or sequences comprising these sequences or having at least 60%, 70%, 80%, 90%, 95%, 97%, 98%, 99% identity with these sequences). Other examples of suitable anti-CD3 binders which also bind to other species CD3 molecules are described in WO2008119567 (Cross-species-specific binding domain) as well as their use in creating bispecific T-cell engagers as taught by WO2010037835.

In an embodiment of the invention, the chosen combination of VH and VL can then be formatted into a single chain variable fragment. This can be in the orientation VH-L2-VL or VL-L2-VH, where L2 is a linker sequence connecting the C-terminal amino acid of the first variable domain with the N-terminus of the second variable domain. A preferred linker is 15-30 amino acids long, has a high flexibility combined with minimal hydrophobicity and immunogenicity or antigenicity. An example of a preferred linker is the (GGGGS)3 linker, possibly extended with a few more (2-4) small amino acids. An example of such an extended (GGGS)3 linker is the sequence ASGGGGSGGGGSGGGGSAG. Alternative linkers are known in the art and have been optimized to minimize structural hindrance to the antibody fragment, to increaser stability or solubility. Linkers known in the art can be evaluated for obtaining more optimal scFv molecules. Further optimization of the L2 linker can be obtained through randomization coupled with a selection system. An example of such an optimization is given by Tang et al. 1996 "Selection of Linkers for a Catalytic Single-chain Antibody Using Phage Display Technology", The Journal of Biological Chemistry, 271, 15682-15686.

The scFv of the invention can be further stabilized by introducing a disulphide stabilized form of the scFv. WO9429350 explains which positions are eligible for engineering a non-natural disulphide bond between the C-terminal halves of the VH and the VL domains. Other examples are illustrated by Schiedl et al, 2000 "Expression of a bispecific dsFv-dsFv' antibody fragment in *Escherichia coli*" Protein Eng. (2000) 13 (10): 725-734. Unlike the teaching of these publications, surprisingly, the preferred molecules of the invention use a single peptide molecule, being a single chain variable fragment further stabilized with the engineered disulphide bond between the proper VH and VL. This prevented formation of highly activating complexes due to multimerization of the CD3 binders. Surprisingly no mismatched pairs were formed even if engineering an interdomain disulphide bond in two different scFvs present in the fusion protein. Equally surprising was the total absence of disulphide mispairing in the fusion protein of the invention, taken into account that the fusion protein already contains 8 intradomain and 1 interchain disulphide bonds, and now two more interdomain disulphide bonds are introduced. Also surprising was that the fusion protein of the invention has a higher stability of the overall molecule. An example is the surprising increase in T-cell activating potency when ds-stabilizing a novel humanized form of the CD3-binding scFv(OKT3) (dshuOKT3-31). Sequences for combined VH/VL binding domains (i.e. also called combined VH/VL) are given in SEQ ID NO 42 (scFv5T4); SEQ ID NO 43 (scFvhu5T4); SEQ ID NO 44 (dsFvhu5T4) for 5T4 binders. Sequences for combined VH/VL binding domains to CD3 wherein binding is based on OKT3 are SEQ ID NO 45 (scFvOKT3); SEQ ID NO 46 (scFvhuOKT3v32) and SEQ ID NO 47 (dsFvhuOKT3v32). In another embodiment of the invention the fusion protein contains a humanized, disulphide stabilized CD3 binder based on UCHT1 in SEQ ID NO 48 (dsFvhuUCHT1-24). Obviously, a person skilled in the art can make other functional combinations based on the listing of sequences in SEQ ID 1-41 (i.e. also called artificial sequences part of the fusion protein). Sequences comprising these sequences (i.e. SEQ ID NO:42, 43, 44, 45, 46, 47, 48) or having at least 60%, 70%, 80%, 90%, 95%, 97%, 98%, 99% identity with these sequences are also encompassed by the invention. It is also known in the art to graft the regions responsible for antigen binding onto a different framework. The antigen binding site is composed of 6 distinct complementary determining regions (CDR), supported by a structural hydrophobic core in the "Vernier" zone. Grafting of the CDR and essential supporting sequences is in the teaching of U.S. Pat. No. 8,399,625, and frequently used to combine antigen binding sites from different species with human framework residues as disclosed in e.g. WO9109967; U.S. Pat. Nos. 5,225,539; 5,693, 761 or 5,821,337. Depending on the antibody not all the sequences in the CDR loops are necessary and the essential positions can be determined by alanine scanning mutagenesis. Here each amino acid in the CDR loops is changed to an Ala and evaluated for binding. A more recent and preferred variant of a technique determining the minimal residues to conserve the antigen binding site is described in WO2012038609 "Super-humanized antibodies", and Pelat et al (2011) "Engineering the variable region of therapeutic IgG antibodies" MAbs 3(3): 243-252. A person skilled in the art could easily change the antigen binding sites contained in the fusion protein of the invention to different frameworks as listed in SEQ ID 1-41.

Once the desired V-domains are identified, a matching pair needs to be selected to graft onto the Fab constant domains CH1 and CL. This technique yields "chimeric" Fab molecules contain a non-native combination of V-domains (VH and VL) and C-domains (CH1 and CL). The substitution can be guided by homology to the native Fab sequence in order not to disrupt the Fab folding which can influence binding and stability. Fab chimerization is well described in the art (see e.g. US20030095964 Process for producing humanized chimera antibody". Even the creation of crossover-Fab chains in the VHCL:VLCH1 configuration is well described and allows successful grafting of the V-domains (see e.g. Fenn et al. (2013). "Crystal structure of an anti-Ang2 CrossFab demonstrates complete structural and functional integrity of the variable domain." PLoS One 8(4): e61953).

In an embodiment of the invention, the C-terminal amino acids of the Fab-derived chains (the CH1-containing chain on the one hand and the CL containing chain on the other hand) will be connected to the selected scFv or dsFv or single domain binder or effector molecule (antibody derived or non-antibody derived) with a chosen linker sequence L1. L1 can be as short as a single amino acid and as long as functionally required. Preferably L1 should introduce some space between the two scFv-derived building blocks and the Fab-derived moiety. Also preferably L1 should have some linker flexibility. The length of L1 can be optimized to fit the optimal distance between the position of the epitope and the CD3. Such examples can be found in Hombach et al. (2007). "T cell activation by antibody-like immunoreceptors: the position of the binding epitope within the target molecule determines the efficiency of activation of redirected T cells." J Immunol 178(7): 4650-4657; and Guest et al. (2005). "The role of extracellular spacer regions in the optimal design of chimeric immune receptors: evaluation of four different scFvs and antigens." J Immunother 28(3): 203-211. The composition of the linker sequence can be optimized for rigidity, protease resistance or contain additional functions.

In a preferred embodiment, the fusion protein of the invention comprises sequences SEQ ID NO 49 (CH1-containing chain) and SEQ ID NO 50 (CL-containing chain) for a fusion protein based on murine 5T4 binders (Tb535C) and SEQ ID NO 51 (CH1-containing chain) and SEQ ID NO 52 (CL-containing chain) for a fusion protein of the invention based on humanized 5T4 binders (Tb535H).

In a preferred embodiment, the fusion protein of the invention comprises sequences having at least 90%, 95%, 96%, 97%, 98%, 99% or 100% identity with SEQ ID NO 49 (CH1-containing chain) and having at least 90%, 95%, 96%, 97%, 98%, 99% or 100% identity with SEQ ID NO 50 (CL-containing chain) for a fusion protein based on murine 5T4 binders (Tb535C). In another preferred embodiment, the fusion protein of the invention comprises sequences having at least 90%, 95%, 96%, 97%, 98%, 99% or 100% identity with SEQ ID NO 51 (CH1-containing chain) and having at least 90%, 95%, 96%, 97%, 98%, 99% or 100% identity with SEQ ID NO 52 (CL-containing chain) for a fusion protein of the invention based on humanized 5T4 binders (Tb535H).

In a preferred embodiment, the fusion protein of the invention comprises or consists sequences SEQ ID NO 49 (CH1-containing chain) and SEQ ID NO 50 (CL-containing chain) for a fusion protein based on murine 5T4 binders (Tb535C). In another preferred embodiment, the fusion protein of the invention comprises or consists of sequences SEQ ID NO 51 (CH1-containing chain) and SEQ ID NO 52 (CL-containing chain) for a fusion protein of the invention based on humanized 5T4 binders (Tb535H).

Best results were obtained with Tb535H: surprisingly it has a compact configuration (FIG. 5A). It could therefore be assumed that it is quite stable (FIG. 6AD) and that it is easier to produce (optimal yield were obtained in FIG. 7D). In addition, surprisingly it has been found that such a fusion protein has a large volume of distribution and slow clearing (FIG. 10). Finally, the activity of this fusion protein is optimal on different tumor types (FIGS. 9, 11A 11B).

In one embodiment the fusion protein of the current invention comprises one or two VH binding domains consist (s) of or comprise(s) or has at least 90% identity with any one of the SEQ ID NOs: 1 to 15. A preferred VH is represented by a sequence consisting of or comprising or having at least 90% identity with SEQ ID NO:6. In another embodiment, the fusion protein of the current invention comprises one or two VL binding domains consisting of or comprising or having at least 90% identity with any one of the SEQ ID NOs: 16 to 25 A preferred VL is represented by a sequence consisting of or comprising or having at least 90% identity with SEQ ID NO:19. Preferably, the fusion protein of the invention comprises a combination of any one of the SEQ ID NOs: 1 to 15 with any of the SEQ ID NOs: 16 to 25. A more preferred fusion protein of the invention comprises a combination of a VH being represented by a sequence consisting of, comprising or having at least 90% identity with SEQ ID NO:6 and a VL being represented by a sequence consisting of, comprising or having at least 90% identity with SEQ ID NO:19.

In another embodiment of the current invention, the fusion protein i) comprises one or two VH binding domains consisting of or comprising or having at least 90% identity with any one of the SEQ ID NOs: 26 to 33 or ii) comprises one or two VL binding domains consist(s) of or comprise(s) or has at least 90% identity with any one of the SEQ ID NOs: 34 to 41. In a preferred embodiment, the fusion protein of the invention comprises a combination of any one of the SEQ ID NOs: 26 to 33 with any of the SEQ ID NOs: 34 to 41. More preferably, the fusion protein i) comprises one or two VH binding domains consisting of or comprising or having at least 90% identity with SEQ ID NO: 29 or ii) comprises one or two VL binding domains consist(s) of or comprise(s) or has at least 90% identity with SEQ ID NO: 37.

In a preferred embodiment, the fusion protein of the invention comprises one or two combined VH/VL binding domains consisting of or comprising or having at least 90% identity with any one of the SEQ ID NOs: 42 to 44 or any one of the SEQ ID NOs: 45 to 48, more in particular, wherein one or two combined VH/VL binding domains consist(s) of or comprise(s) or has at least 90% identity with any one of the SEQ ID NOs: 42 to 44, and the remaining one or two combined VH/VL binding domains consist(s) of or comprise(s) or has at least 90% identity anyone of the SEQ ID NOs: 45 to 48. In a more preferred embodiment, one chain of the fusion protein of the invention comprises SEQ ID NO: 49 whereas the other chain comprises SEQ ID NO: 50, or wherein one chain comprises SEQ ID NO: 51 and the other chain comprises SEQ ID NO: 52. In some embodiments, one chain comprises the following CDR sequences: SYYMH (SEQ ID NO: 53), RINPNNGVTLYNQKFKD (SEQ ID NO: 54), STMITNYVMDY (SEQ ID NO: 55), SGYTFTRYTMH (SEQ ID NO: 56), YINPSR-GYTNYNQKFKD (SEQ ID NO: 57), YYDDHYSL (SEQ ID NO: 58), RASSSVSYMN (SEQ ID NO: 59), DTSKVAS (SEQ ID NO: 60), and QQWSSNPL (SEQ ID NO: 61) and the other chain comprises the following CDR sequences: KASQSVSNDVA (SEQ ID NO: 62), YTSSRYA (SEQ ID NO: 63), QQDYNSPPT (SEQ ID NO: 64), SYYMH (SEQ ID NO: 53), RINPNNGVTLYNQKFKD (SEQ ID NO: 54), and STMITNYVMDY (SEQ ID NO: 55).

The current invention also comprises a nucleic acid sequence encoding the fusion protein of the invention as described herein, as well as a vector, which comprises such nucleic acid sequences, or a host cell transformed or transfected with such nucleic acid sequence or such vector.

The invention also consists of or comprises a process for the production of the fusion protein of the invention, wherein said process comprising culturing a host cell, as defined above, under conditions allowing the expression of the fusion protein of the invention and recovering the produced fusion protein from the culture.

In a preferred embodiment, the invention is a pharmaceutical composition comprising a fusion protein of the invention, or produced according to the process described above, for use as a medicament, more specifically, for use in the prevention, treatment or amelioration of a disease selected from a proliferative disease, a tumorous disease, or an immunological disorder. The invention also provides for a kit comprising a fusion protein of the invention, a nucleic acid molecule as described above, a vector as described above, or a host cell as described above.

The fusion protein of the present invention is preferably an "isolated" fusion protein. "Isolated" when used to describe the fusion protein disclosed herein, means a fusion protein that has been identified, separated and/or recovered from a component of its production environment. Preferably, the isolated fusion protein is free of association with all other components from its production environment. Contaminant components of its production environment, such as that resulting from recombinant transfected cells, are materials that would typically interfere with diagnostic or therapeutic uses for the polypeptide, and may include enzymes, hormones, and other proteinaceous or non-proteinaceous solutes. In preferred embodiments, the fusion protein will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Ordinarily, however, an isolated antibody will be prepared by at least one purification step. The skilled person will understand that the fusion protein of the invention does not occur as such in nature. It has been produced by recombinant molecular biological techniques.

In the context of the invention, a protein is represented by an amino acid sequence. In the context of this invention a preferred protein is a fusion protein as identified herein or a chain thereof.

In the context of the invention, a nucleic acid molecule as a nucleic acid molecule encoding such a protein or fusion protein or a chain thereof is represented by a nucleic acid or nucleotide sequence. A nucleic acid molecule may comprise a regulatory region.

It is to be understood that each protein identified herein by a given Sequence Identity Number (SEQ ID NO) is not limited to this specific sequence as disclosed but also encompass proteins variant or derivative thereof exhibiting a similar activity as earlier defined herein. The same holds for each nucleic acid molecule identified by a given SEQ ID NO: X (for example) and encoding such a protein: the invention also encompasses nucleic acid molecules variant or derivative thereof encoding a protein having a similar activity as the one of the protein initially encoded by SEQ ID NO:X. In this context, an activity may be the binding of the fusion protein to 5T4 and/or the induced killing of 5T4 expressing cells, preferably tumor cells. More preferably, the assessment of the binding and/or the killing is as carried out in the experiments depicted in FIG. 8.

Throughout this application, each time one refers to a specific nucleotide sequence SEQ ID NO (take SEQ ID NO: X as example) encoding a given protein or fusion protein or a chain thereof, one may replace it by:
  i. a nucleotide sequence comprising a nucleotide sequence that has at least 60% sequence identity or similarity with SEQ ID NO: X;
  ii. a nucleotide sequences the complementary strand of which hybridizes to a nucleic acid molecule of sequence of (i);
  iii. a nucleotide sequence the sequence of which differs from the sequence of a nucleic acid molecule of (i) or (ii) due to the degeneracy of the genetic code; or, iv. a nucleotide sequence that encodes an amino acid sequence that has at least 60% amino acid identity or similarity with an amino acid sequence encoded by a nucleotide sequence SEQ ID NO: X.

Throughout this application, each time one refers to a specific amino acid sequence SEQ ID NO (take SEQ ID NO: Y as example), one may replace it by: a protein or fusion protein or a chain thereof comprising an amino acid sequence that has at least 60% sequence identity or similarity with amino acid sequence SEQ ID NO: Y.

Each nucleotide sequence or amino acid sequence described herein by virtue of its identity or similarity percentage (at least 60%) with a given nucleotide sequence or amino acid sequence respectively has in a further preferred embodiment an identity or a similarity of at least 65%, 70%, 75%, 80%, 85%, 90%, 95%, 97%, 98%, 99% or more identity or similarity with the given nucleotide or amino acid sequence respectively. In a preferred embodiment, sequence identity or similarity is determined by comparing the whole length of the sequences as identified herein. Unless otherwise indicated herein, identity or similarity with a given SEQ ID NO means identity or similarity based on the full length of said sequence (i.e. over its whole length or as a whole).

"Sequence identity" is herein defined as a relationship between two or more amino acid (polypeptide or protein) sequences or two or more nucleic acid (polynucleotide) sequences, as determined by comparing the sequences. In a preferred embodiment, sequence identity is calculated based on the full length of two given SEQ ID NO or on part thereof. Part thereof preferably means at least 10%, 20%, 30%, 40%, 50%, 60%, 70%, 80%, 90%, or 100% of both SEQ ID NO. In the art, "identity" also means the degree of sequence relatedness between amino acid or nucleic acid sequences, as the case may be, as determined by the match between strings of such sequences.

"Similarity" between two amino acid sequences is determined by comparing the amino acid sequence and its conserved amino acid substitutes of one polypeptide to the sequence of a second polypeptide. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gln; Ile to Leu or Val; Leu to Ile or Val; Lys to Arg; Gln or Glu; Met to Leu or Ile; Phe to Met, Leu or Tyr; Ser to Thr; Thr to Ser; Trp to Tyr; Tyr to Trp or Phe; and, Val to Ile or Leu.

Several types of fusion proteins variants encompassed are described below. Amino acid sequence modifications of the fusion proteins described herein are contemplated. For example, it may be desirable to improve the binding affinity and/or other biological properties of the antibody. Amino acid sequence variants of the fusion proteins are prepared by introducing appropriate nucleotide changes into the fusion proteins nucleic acid, or by peptide synthesis.

Such modifications include, for example, deletions from, and/or insertions into, and/or substitutions of, residues within the amino acid sequences of the fusion proteins. Any combination of deletion, insertion, and substitution is made to arrive at the final construct, provided that the final construct possesses the desired characteristics. The amino acid changes also may alter post-translational processes of the fusion proteins, such as changing the number or position of glycosylation sites. Preferably, 1, 2, 3, 4, 5, 6, 7, 8, 9, or 10 amino acids may be substituted in a CDR, while 1, 2, 3, 4, 5, 6, 7, 8, 9, 10, 11, 12, 13, 14, 15, 16, 17, 18, 19, 20, or 25 amino acids may be substituted in the FRs. The substitutions are preferably conservative substitutions as described herein. Additionally or alternatively, 1, 2, 3, 4, 5, or 6 amino acids may be inserted or deleted in each of the CDRs (of course, dependent on their length), while 1, 2, 3, 4, 5, 6, 7, 8, 9, 10, 11, 12, 13, 14, 15, 16, 17, 18, 19, 20, or 25 amino acids may be inserted or deleted in each of the FRs.

A useful method for identification of certain residues or regions of the fusion proteins that are preferred locations for mutagenesis is called "alanine scanning mutagenesis" as described by Cunningham and Wells in Science, 244: 1081-1085 (1989). Here, a residue or group of target residues within the fusion protein is/are identified (e.g. charged residues such as arg, asp, his, lys, and glu) and replaced by a neutral or negatively charged amino acid (most preferably alanine or polyalanine) to affect the interaction of the amino acids with epitope.

Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at a target codon or region and the expressed fusion protein variants are screened for the desired activity.

Preferably, amino acid sequence insertions include amino- and/or carboxyl-terminal fusions ranging in length from one, two, three, four, five, six, seven, eight, nine or ten residues to polypeptides containing a hundred or more residues, as well as intrasequence insertions of single or multiple amino acid residues. An insertional variant of the fusion protein include the fusion to the N- or C-terminus of the antibody to an enzyme or a fusion to a polypeptide which increases the serum half-life of the antibody.

Another type of variant is an amino acid substitution variant. These variants have preferably at least one, two, three, four, five, six, seven, eight, nine or ten amino acid residues in the fusion protein replaced by a different residue. The sites of greatest interest for substitutional mutagenesis include the CDRs of the heavy and/or light chain, in particular the hypervariable regions, but FR alterations in the heavy and/or light chain are also contemplated.

For example, if a CDR sequence encompasses 6 amino acids, it is envisaged that one, two or three of these amino acids are substituted. Similarly, if a CDR sequence encompasses 15 amino acids it is envisaged that one, two, three, four, five or six of these amino acids are substituted.

Generally, if amino acids are substituted in one or more or all of the CDRs of the heavy and/or light chain, it is preferred that the then-obtained "substituted" sequence is at least 60%, more preferably 65%, even more preferably 70%, particularly preferable 75%, more particularly preferable 80% identical to the "original" CDR sequence as earlier defined herein. This means that it is dependent of the length of the CDR to which degree it is identical to the "substituted" sequence. For example, a CDR having 5 amino acids is preferably 80% identical to its substituted sequence in order to have at least one amino acid substituted. Accordingly, the CDRs of the fusion protein may have different degrees of identity to their substituted sequences, e.g., CDRL1 may have 80%, while CDRL3 may have 90%. Preferred substitutions (or replacements) are conservative substitutions. However, any substitution (including non-conservative substitution) is envisaged as long as the fusion protein retains its capability to bind to 5T4 via the first binding domain and to CD3s via the second binding domain and/or its CDRs have an identity to the then substituted sequence (at least 60%, more preferably 65%, even more preferably 70%, particularly preferable 75%, more particularly preferable 80% identical to the "original" CDR sequence).

Other modifications of the fusion protein are contemplated herein. For example, the fusion protein may be linked to one of a variety of nonproteinaceous polymers, e.g., polyethylene glycol, polypropylene glycol, polyoxyalkylenes, or copolymers of polyethylene glycol and polypropylene glycol. The fusion protein also may be entrapped in microcapsules prepared, for example, by coacervation techniques or by interfacial polymerization (for example, hydroxymethylcellulose or gelatin-microcapsules and poly (methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980). The fusion proteins disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. J. Biol. Chem. 257: 286-288 (1982) via a disulfide interchange reaction. A chemotherapeutic agent is optionally contained within the liposome. See Gabizon et al. J. National Cancer Inst. 81 (19) 1484 (1989).

When using recombinant techniques, the fusion protein can be produced intracellular^, in the periplasmic space, or directly secreted into the medium. If the fusion protein is produced intracellularly, as a first step, the particulate debris, either host cells or lysed fragments, are removed, for example, by centrifugation or ultrafiltration. Carter et al., Bio/Technology 10: 163-167 (1992) describe a procedure for isolating antibodies which are secreted to the periplasmic space of *E coli.*

The fusion protein composition prepared from the cells can be purified using, for example, hydroxylapatite chromatography, gel electrophoresis, dialysis, and affinity chromatography, with affinity chromatography being the preferred purification technique.

In a further aspect, the present invention relates to a nucleic acid sequence encoding a fusion protein of the invention. Said nucleic acid molecule is preferably comprised in a vector which is preferably comprised in a host cell. Said host cell is, e.g. after transformation or transfection with the nucleic acid sequence of the invention, capable of expressing the fusion protein. For that purpose the nucleic acid molecule is operatively linked with control sequences.

As used herein, the term "host cell" is intended to refer to a cell into which a nucleic acid encoding the fusion protein of the invention is introduced by way of transformation, transfection and the like. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, the term "expression" includes any step involved in the production of a fusion protein of the invention including, but not limited to, transcription, post-transcriptional modification, translation, post-translational modification, and secretion. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. Suitable host cells include prokaryotes and eukaryotic host cells including yeasts, fungi, insect cells and mammalian cells. The fusion protein of the invention can be produced in bacteria.

After expression, the fusion protein of the invention, preferably the fusion protein is isolated from the *E. coli* cell paste in a soluble fraction and can be purified through, e.g., affinity chromatography and/or size exclusion. Final purification can be carried out similar to the process for purifying antibody expressed e. g, in CHO cells. In addition to prokaryotes, eukaryotic microbes such as filamentous fungi or yeast are suitable cloning or expression hosts for the fusion protein of the invention. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e. g., *K. lactis*, *K. fragilis* (ATCC 12424), *K. bulgaricus* (ATCC 16045), *K. wickeramii* (ATCC 24178), *K. waltii* (ATCC 56500), *K. drosophilarum* (ATCC 36906), *K. thermotolerans*, and *K. marxianus*; *yarrowia* (EP 402 226); *Pichia pastoris* (EP 183 070); *Candida*; *Trichoderma reesia* (EP 244 234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*. Suitable host cells for the expression of glycosylated fusion protein of the invention, preferably antibody derived fusion proteins are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruit fly), and *Bombyx mori* have been identified. A variety of viral strains for transfection are publicly available, e. g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, *petunia*, tomato, *Arabidopsis* and tobacco can also be utilized as hosts. Cloning and expression vectors useful in the production of proteins in plant cell culture are known to those of skill in the art. See e.g. Hiatt et al., Nature (1989) 342: 76-78, Owen et al. (1992) Bio/Technology 10: 790-794, Artsaenko et al. (1995) The Plant J 8: 745-750, and Fecker et al. (1996) Plant Mol Biol 32: 979-986.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36: 59 (1977)); baby hamster kidney cells (BHK, ATCC CCL 10); Chinese hamster ovary cells/-DHFR (CHO, Urlaub et al., Proc. Natl. Acad. Sci. USA 77: 4216 (1980)); mouse Sertoli cells (TM4, Mather, Biol. Reprod. 23: 243-251 (1980)); monkey kidney cells (CVI ATCC CCL 70); African green monkey kidney cells (VERO-76, ATCC CRL 1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2,1413 8065); mouse mammary tumor (MMT 060562, ATCC CCL 5 1); TRI cells (Mather et al., Annals N. Y Acad. Sci. 383: 44-68 (1982)); MRC 5 cells; FS4 cells; and a human hepatoma line (Hep G2). When using recombinant techniques, the fusion protein of the invention can be produced intracellularly, in the periplasmic space, or directly secreted into the medium. If the fusion protein is produced intracellularly, as a first step, the particulate debris, either host cells or lysed fragments, are removed, for example, by centrifugation or ultrafiltration. Carter et al., Bio/Technology 10: 163-167 (1992) describe a procedure for isolating antibodies which are secreted to the periplasmic space of *E coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The fusion protein of the invention prepared from the host cells can be purified using, for example, hydroxylapatite chromatography, gel electrophoresis, dialysis, and affinity chromatography, with affinity chromatography being the preferred purification technique. The matrix to which the affinity ligand is attached is most often agarose, but other matrices are available. Mechanically stable matrices such as controlled pore glass or poly (styrenedivinyl) benzene allow for faster flow rates and shorter processing times than can be achieved with agarose. Where the fusion protein of the invention comprises a CH3 domain, the Bakerbond ABXM-resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromato-focusing, SDS-PAGE, and ammonium sulfate precipitation are also available depending on the antibody to be recovered. In another aspect, processes are provided for producing fusion proteins of the invention, said processes comprising culturing a host cell defined herein under conditions allowing the expression of the fusion protein and recovering the produced fusion protein from the culture. In an alternative embodiment, compositions are provided comprising a fusion protein of the invention, or produced according to the process of the invention. Preferably, said composition is a pharmaceutical composition.

As used herein, the term "pharmaceutical composition" relates to a composition for administration to a patient, preferably a human patient. The particular preferred pharmaceutical composition of this invention comprises the fusion protein of the invention. Preferably, the pharmaceutical composition comprises suitable formulations of carriers, stabilizers and/or excipients. In a preferred embodiment, the pharmaceutical composition comprises a composition for parenteral, transdermal, intraluminal, intraarterial, intrathecal and/or intranasal administration or by direct injection into tissue. It is in particular envisaged that said composition is administered to a patient via infusion or injection. Administration of the suitable compositions may be effected by different ways, e.g., by intravenous, intraperitoneal, subcutaneous, intramuscular, topical or intradermal administration. In particular, the present invention provides for an uninterrupted administration of the suitable composition. As a non-limiting example, uninterrupted, i.e. continuous administration may be realized by a small pump system worn by the patient for metering the influx of therapeutic agent into the body of the patient. The pharmaceutical composition comprising the fusion protein of the invention can be administered by using said pump systems. Such pump systems are generally known in the art, and commonly rely on periodic exchange of cartridges containing the therapeutic agent to be infused. When exchanging the cartridge in such a pump system, a temporary interruption of the otherwise uninterrupted flow of therapeutic agent into the body of the patient may ensue. In such a case, the phase of administration prior to cartridge replacement and the phase of administration following cartridge replacement would still be considered within the meaning of the pharmaceutical means and methods of the invention together make up one "uninterrupted administration" of such therapeutic agent.

The continuous or uninterrupted administration of these fusion proteins of the invention may be intravenuous or subcutaneous by way of a fluid delivery device or small pump system including a fluid driving mechanism for driving fluid out of a reservoir and an actuating mechanism for actuating the driving mechanism. Pump systems for subcutaneous administration may include a needle or a cannula for penetrating the skin of a patient and delivering the suitable composition into the patient's body. Said pump systems may be directly fixed or attached to the skin of the patient independently of a vein, artery or blood vessel, thereby allowing a direct contact between the pump system and the skin of the patient. The pump system can be attached to the skin of the patient for 24 hours up to several days. The pump system may be of small size with a reservoir for small volumes. As a non-limiting example, the volume of the reservoir for the suitable pharmaceutical composition to be administered can be between 0.1 and 50 ml.

The continuous administration may be transdermal by way of a patch worn on the skin and replaced at intervals. One of skill in the art is aware of patch systems for drug delivery suitable for this purpose. It is of note that transdermal administration is especially amenable to uninterrupted administration, as exchange of a first exhausted patch can advantageously be accomplished simultaneously with the placement of a new, second patch, for example on the surface of the skin immediately adjacent to the first exhausted patch and immediately prior to removal of the first exhausted patch. Issues of flow interruption or power cell failure do not arise.

The inventive compositions may further comprise a pharmaceutically acceptable carrier. Examples of suitable pharmaceutical carriers are well known in the art and include solutions, e.g. phosphate buffered saline solutions, water, emulsions, such as oil/water emulsions, various types of wetting agents, sterile solutions, liposomes, etc. Compositions comprising such carriers can be formulated by well-known conventional methods. Formulations can comprise carbohydrates, buffer solutions, amino acids and/or surfactants. Carbohydrates may be non-reducing sugars, preferably trehalose, sucrose, octasulfate, sorbitol or xylitol. In general, as used herein, "pharmaceutically acceptable carrier" means any and all solvents, dispersion media, coatings, antibacterial and antifungal agents, isotonic and absorption delaying agents, compatible with pharmaceutical administration. The use of such media and agents for pharmaceutically active substances is well known in the art. Acceptable carriers, excipients, or stabilizers are nontoxic to recipients at the dosages and concentrations employed and include: additional buffering agents; preservatives; co-solvents; antioxidants, including ascorbic acid and methionine; chelating agents such as EDTA; metal complexes (e.g., Zn-protein complexes); biodegradable polymers, such as polyesters; salt-forming counterions, such as sodium, polyhydric sugar alcohols; amino acids, such as alanine, glycine, asparagine, 2-phenylalanine, and threonine; sugars or sugar alcohols, such as trehalose, sucrose, octasulfate, sorbitol or xylitol stachyose, mannose, sorbose, xylose, ribose, myoinisitose, galactose, lactitol, ribitol, myoinisitol, galactitol, glycerol, cyclitols (e.g., inositol), polyethylene glycol; sulfur containing reducing agents, such as glutathione, thioctic acid, sodium thioglycolate, thioglycerol, [alpha]-monothioglycerol, and sodium thio sulfate; low molecular weight proteins, such as human serum albumin, bovine serum albumin, gelatin, or other immunoglobulins; and hydrophilic polymers, such as polyvinylpyrrolidone. Such formulations may be used for continuous administrations which may be intravenuous or subcutaneous with and/or without pump systems. Amino acids may be charged amino acids, preferably lysine, lysine acetate, arginine, glutamate and/or histidine. Surfactants may be detergents, preferably with a molecular weight of >1.2 KD and/or a polyether, preferably with a molecular weight of >3 KD. Non-limiting examples for preferred detergents are Tween 20, Tween 40, Tween 60, Tween 80 or Tween 85. Non-limiting examples for preferred polyethers are PEG 3000, PEG 3350, PEG 4000 or PEG 5000. Buffer systems used in the present invention can have a preferred pH of 5-9 and may comprise citrate, succinate, phosphate, histidine and acetate. The compositions of the present invention can be administered to the subject at a suitable dose which can be determined e.g. by dose escalating studies by administration of increasing doses of the polypeptide of the invention exhibiting cross-species specificity described herein to non-chimpanzee primates, for instance macaques. As set forth above, the polypeptide of the invention exhibiting cross-species specificity described herein can be advantageously used in identical form in preclinical testing in non-chimpanzee primates and as drug in humans. These compositions can also be administered in combination with other proteinaceous and non-proteinaceous drugs. These drugs may be administered simultaneously with the composition comprising the polypeptide of the invention as defined herein or separately before or after administration of said polypeptide in timely defined intervals and doses. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyloleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, inert gases and the like. In addition, the composition of the present invention might comprise proteinaceous carriers, like, e.g., serum albumin or immunoglobulin, preferably of human origin. It is envisaged that the composition of the invention might comprise, in addition to the polypeptide of the invention defined herein, further biologically active agents, depending on the intended use of the composition. Such agents might be drugs acting on the gastrointestinal system, drugs acting as cytostatica, drugs preventing hyperurikemia, drugs inhibiting immunoreactions (e.g. corticosteroids), drugs modulating the inflammatory response, drugs acting on the circulatory system and/or agents such as cytokines known in the art. It is also envisaged that the fusion protein of the present invention is applied in a co-therapy, i.e., in combination with another anti-cancer medicament.

The biological activity of the pharmaceutical composition defined herein can be determined for instance by cytotoxicity assays, as described in the following examples, in WO 99/54440 or by Schlereth et al. (Cancer Immunol. Immunother. 20 (2005), 1-12). "Efficacy" or "in vivo efficacy" as used herein refers to the response to therapy by the pharmaceutical composition of the invention, using e.g. standardized NCI response criteria. The success or in vivo efficacy of the therapy using a pharmaceutical composition of the invention refers to the effectiveness of the composition for its intended purpose, i.e. the ability of the composition to cause its desired effect, i.e. depletion of pathologic cells, e.g. tumor cells. The in vivo efficacy may be monitored by established standard methods for the respective disease entities including, but not limited to white blood cell counts, differentials, Fluorescence Activated Cell Sorting, bone marrow aspiration. In addition, various disease specific clinical chemistry parameters and other established standard methods may be used. Furthermore, computer-aided tomography, X-ray, nuclear magnetic resonance tomography (e.g. for National Cancer Institute-criteria based response assessment [Cheson B D, Horning S J, Coiffier B, Shipp M A, Fisher R1, Connors J M, Lister T A, Vose J, Grillo-Lopez A, Hagenbeek A, Cabanillas F, Klippensten D, Hiddemann W, Castellino R, Harris N L, Armitage J O, Carter W, Hoppe R, Canellos G P. Report of an international workshop to standardize response criteria for non-Hodgkin's lymphomas. NCI Sponsored International Working Group. J Clin Oncol. 1999 April; 17(4): 1244]), positron-emission tomography scanning, white blood cell counts, differentials, Fluorescence Activated Cell Sorting, bone marrow aspiration, lymph node biopsies/histologies, and various lymphoma specific clinical chemistry parameters (e.g. lactate dehydrogenase) and other established standard methods may be used.

Another major challenge in the development of drugs such as the pharmaceutical composition of the invention is the predictable modulation of pharmacokinetic properties. To this end, a pharmacokinetic profile of the drug candidate, i.e. a profile of the pharmacokinetic parameters that affect the ability of a particular drug to treat a given condition, can be established. Pharmacokinetic parameters of the drug influencing the ability of a drug for treating a certain disease entity include, but are not limited to: half-life, volume of distribution, hepatic first-pass metabolism and the degree of blood serum binding. The efficacy of a given drug agent can be influenced by each of the parameters mentioned above.

"Tmax" is the time after which maximal blood concentration of the drug is reached, and "Cmax" is the blood concentration maximally obtained with a given drug. The time to reach a blood or tissue concentration of the drug which is required for its biological effect is influenced by all parameters. Pharmacokinetic parameters of bispecific single chain antibodies exhibiting cross-species specificity, which may be determined in preclinical animal testing in non-chimpanzee primates as outlined above, are also set forth e.g. in the publication by Schlereth et al. (Cancer Immunol. Immunother. 20 (2005), 1-12). The term "toxicity" as used herein refers to the toxic effects of a drug manifested in adverse events or severe adverse events. These side events might refer to a lack of tolerability of the drug in general and/or a lack of local tolerance after administration. Toxicity could also include teratogenic or carcinogenic effects caused by the drug. The term "safety", "in vivo safety" or "tolerability" as used herein defines the administration of a drug without inducing severe adverse events directly after administration (local tolerance) and during a longer period of application of the drug. "Safety", "in vivo safety" or "tolerability" can be evaluated e.g. at regular intervals during the treatment and follow-up period. Measurements include clinical evaluation, e.g. organ manifestations, and screening of laboratory abnormalities. Clinical evaluation may be carried out and deviations to normal findings recorded/coded according to NCI-CTC and/or MedDRA standards. Organ manifestations may include criteria such as allergy/immunology, blood/bone marrow, cardiac arrhythmia, coagulation and the like, as set forth e.g. in the Common Terminology Criteria for adverse events v3.0 (CTCAE). Laboratory parameters which may be tested include for instance haematology, clinical chemistry, coagulation profile and urine analysis and examination of other body fluids such as serum, plasma, lymphoid or spinal fluid, liquor and the like. Safety can thus be assessed e.g. by physical examination, imaging techniques (i.e. ultrasound, x-ray, CT scans, Magnetic Resonance Imaging (MRI), other measures with technical devices (i.e. electrocardiogram), vital signs, by measuring laboratory parameters and recording adverse events. For example, adverse events in non-chimpanzee primates in the uses and methods according to the invention may be examined by histopathological and/or histochemical methods.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity ofthe infection and the general state ofthe subject's own immune system. The term "patient" includes human and other mammalian subjects that receive either prophylactic or therapeutic treatment.

The term "effective and non-toxic dose" as used herein refers to a tolerable dose of an inventive fusion protein which is high enough to cause depletion of pathologic cells, tumor elimination, tumor shrinkage or stabilization of disease without or essentially without major toxic effects. Such effective and non-toxic doses may be determined e.g. by dose escalation studies described in the art and should be below the dose inducing severe adverse side events (dose limiting toxicity, DLT).

The above terms are also referred to e.g. in the Preclinical safety evaluation of biotechnology-derived pharmaceuticals S6; ICH Harmonised Tripartite Guideline; ICH Steering Committee meeting on Jul. 16, 1997.

The appropriate dosage, or therapeutically effective amount, of the fusion protein of the invention will depend on the condition to be treated, the severity of the condition, prior therapy, and the patient's clinical history and response to the therapeutic agent. The proper dose can be adjusted according to the judgment of the attending physician such that it can be administered to the patient one time or over a series of administrations. The pharmaceutical composition can be administered as a sole therapeutic or in combination with additional therapies such as anti-cancer therapies as needed.

The pharmaceutical compositions of this invention are particularly useful for parenteral administration, i.e., subcutaneously, intramuscularly, intravenously, intra-articular and/or intra-synovial. Parenteral administration can be by bolus injection or continuous infusion. If the pharmaceutical composition has been lyophilized, the lyophilized material is first reconstituted in an appropriate liquid prior to administration. The lyophilized material may be reconstituted in, e.g., bacteriostatic water for injection (BWFI), physiological saline, phosphate buffered saline (PBS), or the same formulation the protein had been in prior to lyophilization.

Preferably, the fusion protein of the invention or produced by a process of the invention is used in the prevention, treatment or amelioration of a disease selected from a proliferative disease, a tumorous disease, or an immunological disorder. An alternative embodiment of the invention provides a method for the treatment or amelioration of a disease selected from a proliferative disease, a tumorous disease, or an immunological disorder comprising the step of administering to a patient in the need thereof the fusion protein of the invention or produced by a process of the invention. A tumorous disease could be replaced by a cancer. A preferred cancer is a cancer wherein the extra-cellular antigen 5T4 is expressed in tumor cells. The expression of 5T4 could be assessed using FACS analysis. A more preferred cancer is mesothelioma, breast cancer, ovarian cancer, colorectal carcinoma, cancer of the cervix, gastric cancer, lung cancer or colon cancer. A preferred breast cancer is a so-called triple negative breast cancer. A preferred colon cancer is a KRAS-mutated colon cancer.

The formulations described herein are useful as pharmaceutical compositions in the treatment and/or prevention of the pathological medical condition as described herein in a patient in need thereof. The term "treatment" refers to both therapeutic treatment and prophylactic or preventative measures. Treatment includes the application or administration of the formulation to the body, an isolated tissue, or cell from a patient who has a disease/disorder, a symptom of a disease/disorder, or a predisposition toward a disease/disorder, with the purpose to cure, heal, alleviate, relieve, alter, remedy, ameliorate, improve, or affect the disease, the symptom of the disease, or the predisposition toward the disease.

Those "in need of treatment" include those already with the disorder, as well as those in which the disorder is to be prevented. The term "disease" is any condition that would benefit from treatment with the protein formulation described herein. This includes chronic and acute disorders or diseases including those pathological conditions that predispose the mammal to the disease in question. Non-limiting examples of diseases/disorders to be treated herein include proliferative disease, a tumorous disease, or an immunological disorder. In another aspect, kits are provided comprising a fusion protein of the invention, a nucleic acid molecule of the invention, a vector of the invention, or a host cell of the invention. The kit may comprise one or more vials containing the fusion protein and instructions for use. The kit may also contain means for administering the fusion protein of the present invention such as a syringe, pump, infusor or the like. In still another aspect, the present invention relates to the use of It should be understood that the inventions herein are not limited to particular methodology, protocols, or reagents, as such can vary. The discussion and examples provided herein are presented for the purpose of describing particular embodiments only and are not intended to limit the scope of the present invention, which is defined solely by the claims. All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

A: minimal binding regions for a 5T4 and an T-cell activating CD3 epitope are isolated, e.g. derived from the V-domain of an antibody, or from other binding molecules. These minimal binding domains are formatted to function both as an N-terminal extensions on CH1:CL heterodimerizing domains, and/or formatted as a single chain variable domain and extended to the N-terminus of the fusion protein of the invention.

B: schematic drawing of gene structures of the Fab L (comprising VL and CL domains) and Fab Fd (comprising VH and CH1 chains), which when co-expressed in the same cell form a Fab heterodimer.

C: schematic drawing of gene structures of a form of a fusion protein of the invention where extra binding domains in the form of single chain variable domains (scFv) are fused to the C-terminus of the CL and CH1 domains by genetic fusion of the coding genes at the mRNA level. In the example the gene structure is based on an intron-less continuous coding sequence.

D: Molecular model of a fusion protein of the invention in ribbon and space-fill representation.

E: Molecular model of a fusion protein of the invention containing a 10-amino acid linkers sequence between both the CH1 and its extended C-terminal binder and the CL and its extended C-terminal binder. The molecular simulation uses maximal flexibility based on a SGGGSGGGSS linker sequence. Representation is in space-fill, darker domains are the fusion protein and silver domains are the antigen bound (same antigen in the model for all 3 binding moieties).

FIG. 1B Illustrates some of the different variations in organization of the binding structures in the fusion protein where structures are based on Fab-chain heterodimers (VH-CH1:VLCL):
    VH(5T4)-CH1-L1-VH(CD3)-L2-VL(CD3) or
    VH(5T4)-CH1-L1-VL(CD3)-L2-VH(CD3)
    are combined with
    VL(5T4)CL-L1-VH(5T4)-L2-VL(5T4) or
    VL(5T4)CL-L1-VL(5T4)-L2-VH(5T4),
    as illustrated for 2 possible combinations in model (i) and (iv).
    Or different form-organizations of
    VH(5T4)-CH1-L1-VH(5T4)-L2-VL(5T4) or
    VH(5T4)-CH1-L1-VL(5T4)-L2-VH(5T4)
    combined with
    VL(5T4)CL-L1-VH(CD3)-L2-VL(CD3) or
    VL(5T4)CL-L1-VL(CD3)-L2-VH(CD3)
    as illustrated for 2 possible combinations in model (ii) and (v).
    Or different form-organizations of
    VH(CD3)-CH1-L1-VH(5T4)-L2-VL(5T4) or
    VH(CD3)-CH1-L1-VL(5T4)-L2-VH(5T4)
    Combined with
    VL(CD3)CL-L1-VH(5T4)-L2-VL(5T4) or
    VL(CD3)CL-L1-VL(5T4)-L2-VH(5T4)
    as illustrated for 2 possible combinations in model (iii) and (vi).

In all combinations the scFv can also be a disulphide stabilized single chain variable fragment (dsFv).

Figure 1C:
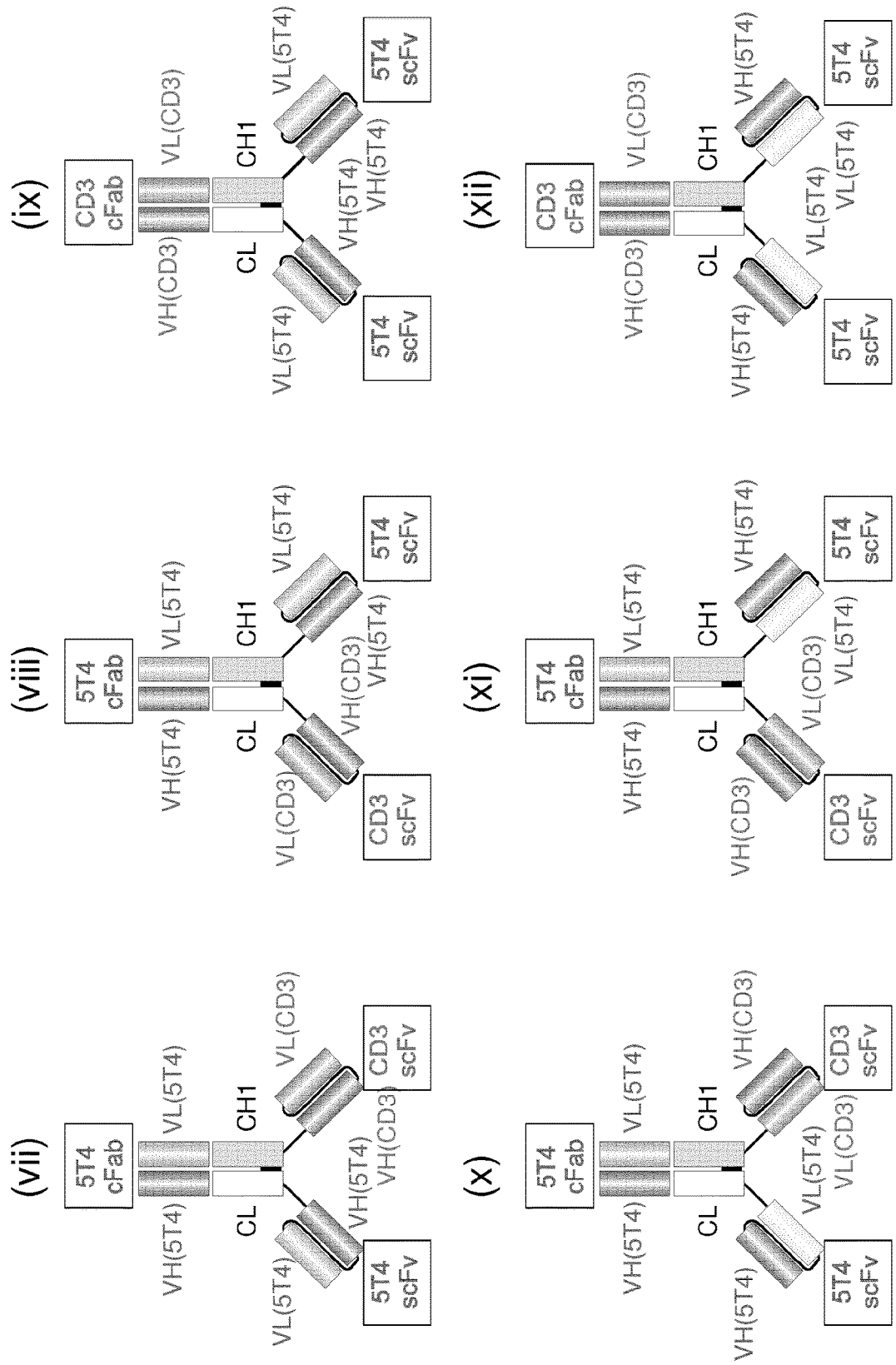
FIG. 1A Represents the preferred principle of making the fusion protein of the invention (also called "Tribody fusion protein").

FIG. 1C Illustrates some of the different variations in organization of the binding structures in the Tb-5T4 fusion protein where structures are based on crossover-Fab-chain (cFab) heterodimers (VHCL:VLCH1):
    VL(5T4)-CH1-L1-VH(CD3)-L2-VL(CD3) or
    VL(5T4)-CH1-L1-VL(CD3)-L2-VH(CD3)
    combined with
    VH(5T4)CL-L1-VH(5T4)-L2-VL(5T4) or
    VH(5T4)CL-L1-VL(5T4)-L2-VH(5T4)
    as illustrated for 2 possible combinations in (vii) and (x).
    Or different form-organizations of
    VL(5T4)-CH1-L1-VH(5T4)-L2-VL(5T4) or
    VL(5T4)-CH1-L1-VL(5T4)-L2-VH(5T4)
    combined with
    VH(5T4)CL-L1-VH(CD3)-L2-VL(CD3) or
    VH(5T4)CL-L1-VL(CD3)-L2-VH(CD3)
    as illustrated for 2 possible combinations in (viii) and (xi).
    Or different form-organizations of
    VL(CD3)-CH1-L1-VH(5T4)-L2-VL(5T4) or
    VL(CD3)-CH1-L1-VL(5T4)-L2-VH(5T4)
    combined with
    VH(CD3)CL-L1-VH(5T4)-L2-VL(5T4) or
    VH(CD3)CL-L1-VL(5T4)-L2-VH(5T4)
    as illustrated for 2 possible combinations in model (ix) and (xii).

In all combinations the scFv can also be a disulphide stabilized single chain variable fragment (dsFv).

Figure 1D:
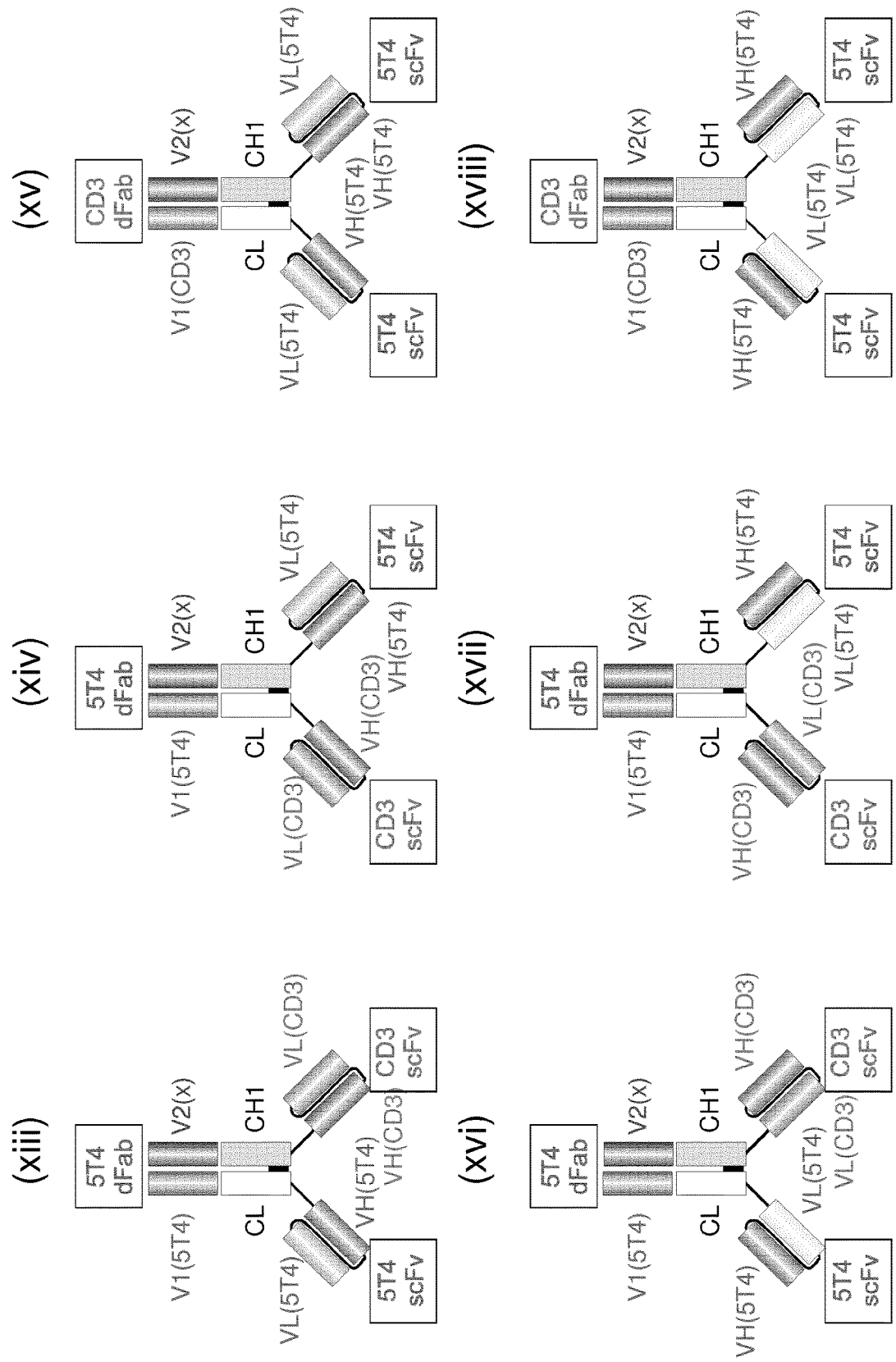

FIG. 1D Illustrates some of the different variations in organization of the binding structures in the Tb-5T4 fusion protein where structures are based on single domain binder fusions to CH1 and CL heterodimers (dFab):
    V1(5T4)CL-L1-VH(5T4)-L2-VL(5T4) or
    V1 (5T4)CL-L1-VL(5T4)-L2-VH(5T4)
    Where V1 is a single domain binder with specificity to 5T4
    combined with
    V2-CH1-L1-VH(CD3)-L2-VL(CD3) or
    V2-CH1-L1-VL(CD3)-L2-VH(CD3)
    where V2 is a single domain binder with a different specificity than for 5T4 or CD3 as illustrated for 2 possible combinations in (xiii) and (xvi)
    Or different form-organizations of
    V2-CH1-L1-VH(5T4)-L2-VL(5T4) or
    V2-CH1-L1-VL(5T4)-L2-VH(5T4)
    combined with
    V1 (5T4)CL-L1-VH(CD3)-L2-VL(CD3) or
    V1 (5T4)CL-L1-VL(CD3)-L2-VH(CD3)
    where V2 is a single domain binder with a different specificity than for 5T4 or CD3 as illustrated for 2 possible combinations in (xiv) and (xvii)
    Or different form-organizations of
    V1 (CD3)-CH1-L1-VH(5T4)-L2-VL(5T4) or
    V1 (CD3)-CH1-L1-VL(5T4)-L2-VH(5T4)
    combined with
    V2-CL-L1-VH(5T4)-L2-VL(5T4) or
    V2-CL-L1-VL(5T4)-L2-VH(5T4)
    where V2 is a single domain binder with a different specificity than for 5T4 or CD3 as illustrated for 2 possible combinations in model (xv) and (xviii).

In all combinations the scFv can also be a disulfide stabilized single chain variable fragment (dsFv)

FIG. 2

A: comparison of the murine 5T4.H8 VH and VL sequences as published by Forsberg 1997 (J. Biol. Chem 272:12430-12436) (SEQ ID 2 and 16) and a humanized sequence (SEQ ID 6 and 19) showing differences in framework and predicted CDR regions (boxed).

B: schematic representation of Tb535C comprising the murine V(5T4) sequences in SEQ ID 2 and 16 and Tb535H-1120 comprising the humanized V(5T4) as in SEQ ID 6 and 19.

C: shows a significant increase in humanness score as expressed in deviation of the mean (z-score) for both the murine and humanized VH and VL D: production yields after IMAC (immobilized metal affinity chromatography) or SEC (size exclusion chomatography) of two tribody fusions comprising different humanized forms of the VH(5T4) and VL(5T4) and extended with a HIS-tag at the C-terminus of the CH1-containing chain (HHHHHH).

FIG. 3

A: schematic representation of the humanized fusion protein Tb535H (SEQ ID 51 and 52).

B: Comparison of KD equilibrium dissociation constants of Tb535H and Tb535C (SEQ ID 49 and 50) as compared to the humanized VH(5T4) SEQ ID 6 and VL(5T4) SEQ ID 19 in either dsFv format, Fab-format, IgG format or BiTE format (scFv(5T4)-scFv(CD3) fusion).

C: Graphical representation of ELISA binding curves on recombinant extracellular domain of 5T4 of Tb535H compared to its parts Fab(5T4) and dsFv(5T4).

D: FACS decoration under saturating conditions of Tb535H and its parts Fab(5T4) and dsFv(5T4) on the MSTO-211H 5T4-positive mesothelioma cell line.

E: Titration of binding of Tb535H on the MSTO-211H 5T4-positive mesothelioma cell line and comparison of 50% binding concentration (KD) with ELISA method.

F: Titration of binding of Tb535H on peripheral blood monocytes of 3 different donors. KD values are reproducible around 25 nM.

FIG. 4A

A: schematic representation of Tb535H with an indication of all disulphide bonds present in the protein.

B: listing of all natural and engineered disulphide bonds in Tb535H.

C: indication of all disulphide bonds on the sequence of Tb535H.

D: comparison of the formation of the engineered disulphide bonds, which is surprisingly better in the Tb535H than in Tb535C (non-reducing BOLT SDS-PAGE). The reducing gel shows chains of expected molecular weight. In between a molecular weight calibration curve is shown.

FIG. 4B

A: activity titration curves comparing the influence of humanization and stabilization of the CD3 binder VH(CD3) SEQ ID 29 and VL(CD3) SEQ ID 37 incorporated in a Tb-5T4.

B: influence of induced stress on non-disulphide stabilized Tb-5T4 on formation of multimers. The figure shows overlaying profiles of an analytical gel filtration elution after incubation for 3 days at 20° C. or 37° C. Monomers (1) and multimers (2-4) are indicated.

C: influence of induced stress on disulphide stabilized Tb-5T4 on formation of multimers after 3 days at 37° C. There was no change in multimer formation as compared with the start situation.

Figure 5:
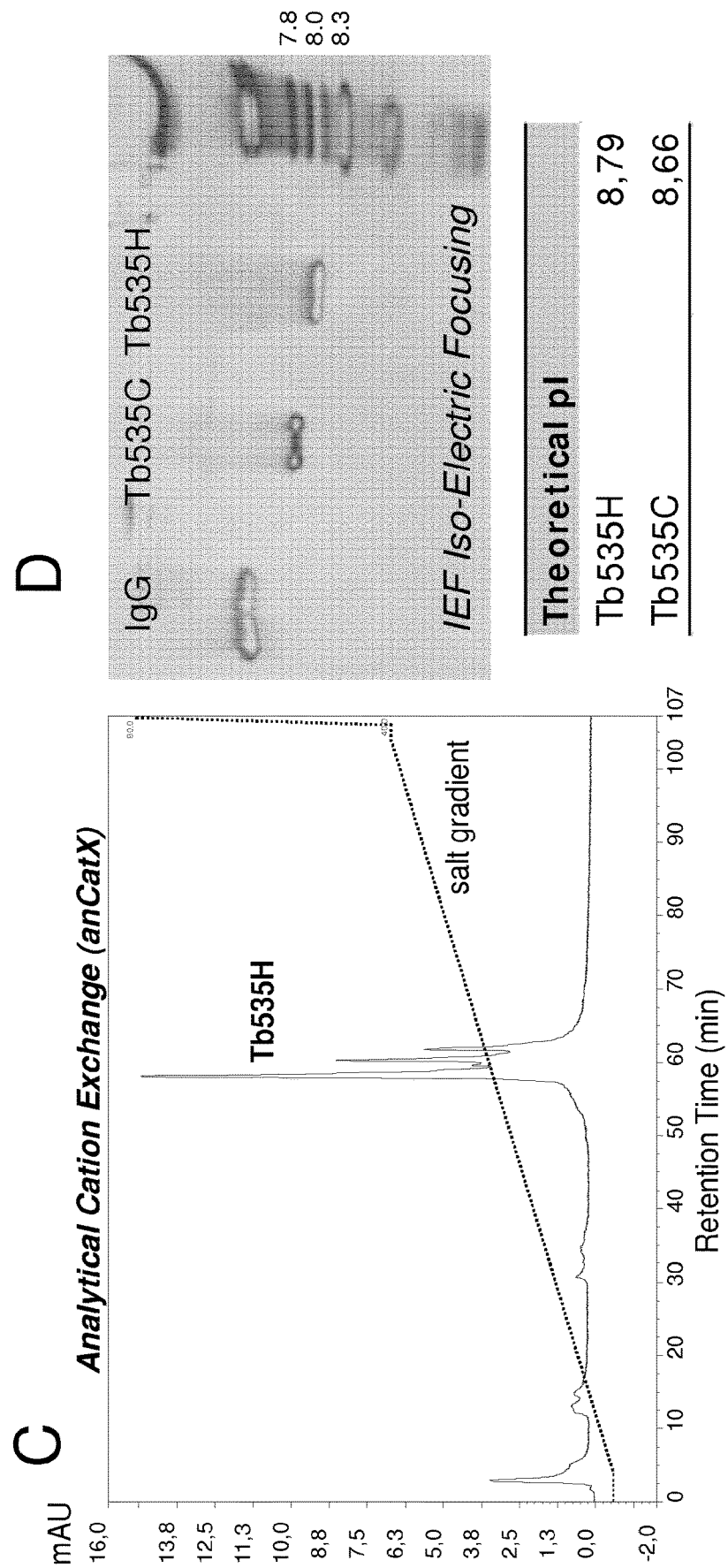

FIG. 5 Analysis of Tb535 fusion protein

A: elution profile of an analytical gel filtration comparing Tb535C and Tb535H. The calibration using 150 kDa, 100 kDa, 50 kDa and 25 kDa IgG-derived molecules is shown. The table shows the predicted size of Tb535H and Tb535C as derived from the calibration line. Surprisingly, Tb535H shows a more compact configuration.

B: mass spectrometry analysis of Tb535H shows correct molecular weight and identifies MW isoforms.

C: analytical cation exchange analysis of Tb535H identifies limited number of charge isomers.

D: iso-electro focusing compares Tb535C, Tb535H with the IgG form.

FIG. 6A Stability of Tb535 based on melting curves of the protein

A: Schematic representation of Tb535H.

B: Comparison of stability by melting temperature by Thermofluor assay between Tb535C and Tb535H.

C: Comparison of melting curves by Thermofluor assay of Tb535H with its individual components (Fab(5T4); dsFv (5T4), dsFv(CD3)). The theoretical sum of the components is also shown. Surprisingly the Tb535H is not the sum of the components and the fusion protein is more stable.

D: Comparison of melting curves by Thermofluor assay of Tb535H with BiTE (dsFv(5T4)-dsFv(CD3) fusion) and IgG1(5T4) formats based on the same V-domain sequences. Surprisingly the Tb535H is more stable than both IgG and the scFv-fusion (BiTE).

FIG. 6B Stability of Tb535 after 72 h incubation at 37° C.

A: Tb535H and Tb535C forms were incubated for 72 h at 37° C. in PBS and before and thereafter analyzed by analytical size exclusion chromatography. No multimer formation is seen after incubation.

B: Tb535H and Tb535C forms were incubated for 72 h at 37° C. in human serum and thereafter analyzed by activity titration in a cell killing assay (MSTO-211H 5T4-positive mesothelioma cell line with human PBMC E:T 5:1, 48 h assay). No difference in activity was noticed after incubation.

Figure 7:
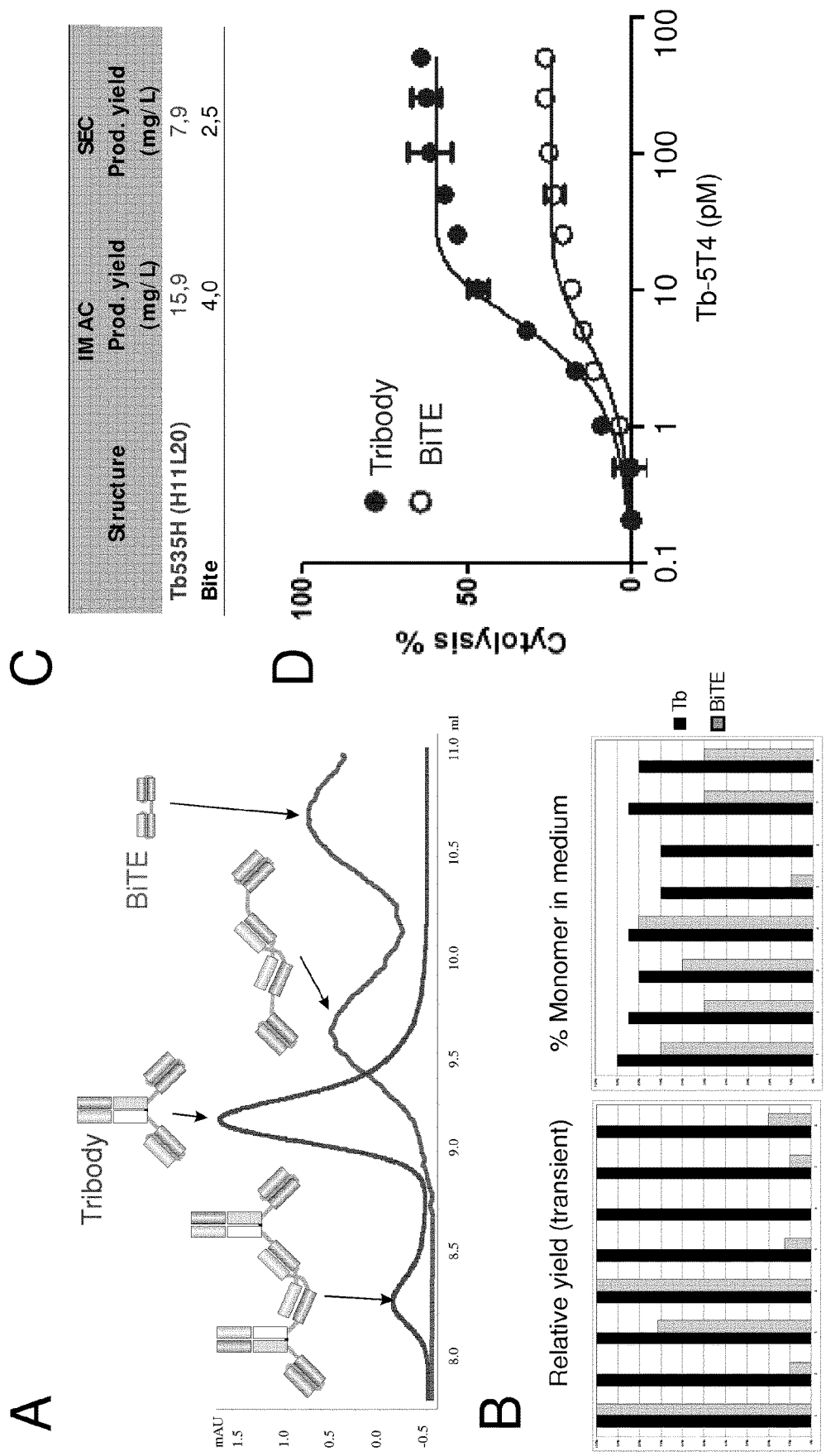

FIG. 7 Comparison of fusion protein of the invention (Fab-(scFv)2) and BiTE (scFv-scFv) formats.

A: Typical formation of monomer and dimer using both fusion protein formats. BiTE formats tend to have a higher proportion of dimers formed.

B: Relative yield in molar comparison where the fusion protein of the invention format is set as 100% and compared to the BiTE format with the same sequence. The formats of the fusion protein of the invention typically have higher production yields.

C: Comparison of production yields after purification of a fusion protein (Tb535H-1120) with a BiTE format based on the same sequences.

D: Comparison of activity titration (induced killing of 5T4-positive tumor cells by human PBMC in mixed culture) of a fusion protein format with a BiTE format shows EC50 values in the same range but a higher percentage of tumor cells is killed using the fusion protein format of the invention form T-cell engager.

Figure 8:
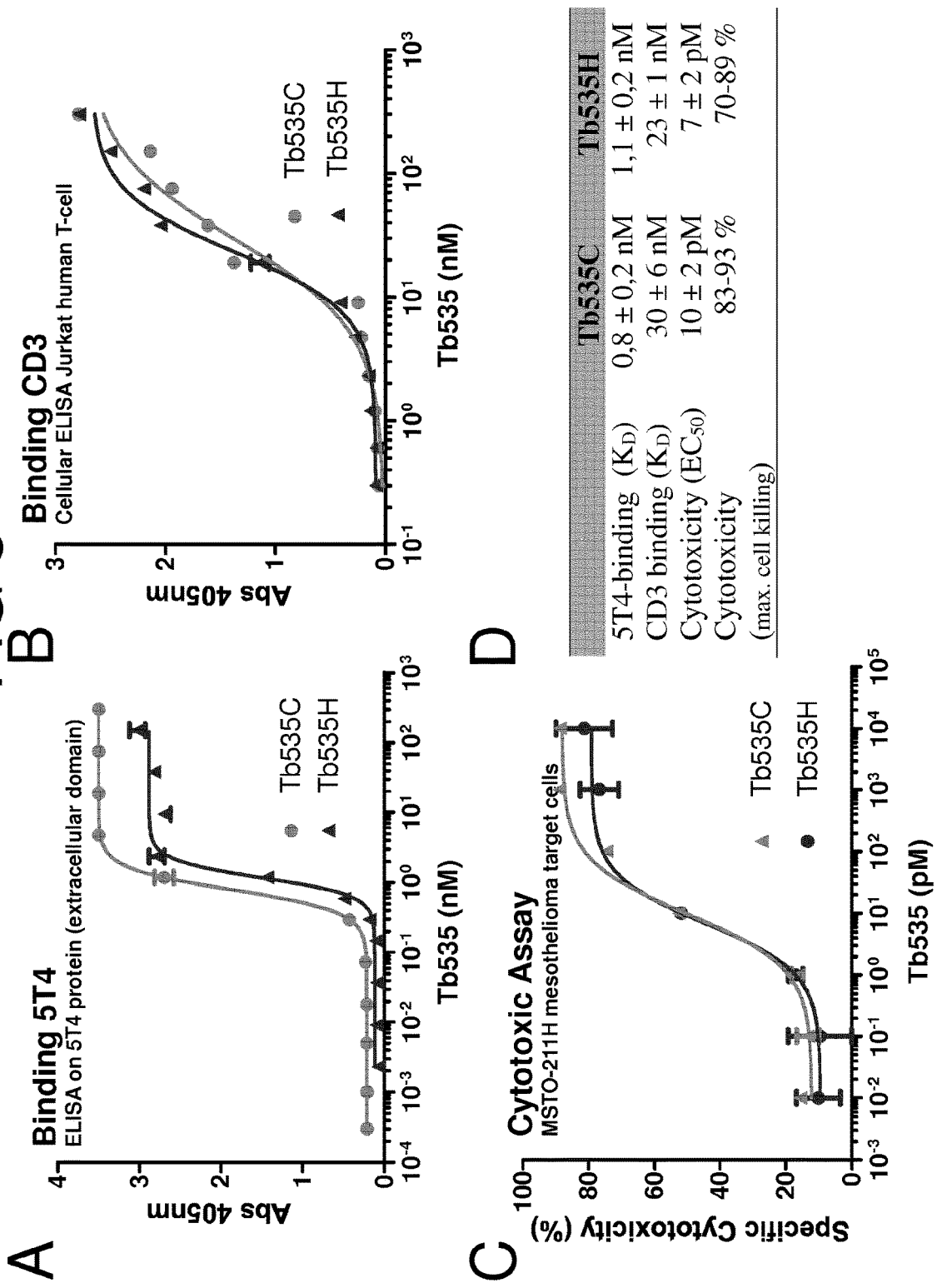

FIG. 8 Comparison of binding and activity of Tb535C and Tb535H

A: ELISA binding on recombinant extracellular domain of the 5T4 antigen.

B: ELISA binding on a human T-cell line (Jurkat).

C: Cytotoxicity titration in a mixed culture of MSTO-211H 5T4-positive mesothelioma tumor cells.

D: Table comparing binding and activity of Tb535C and Tb535H.

Figure 9:
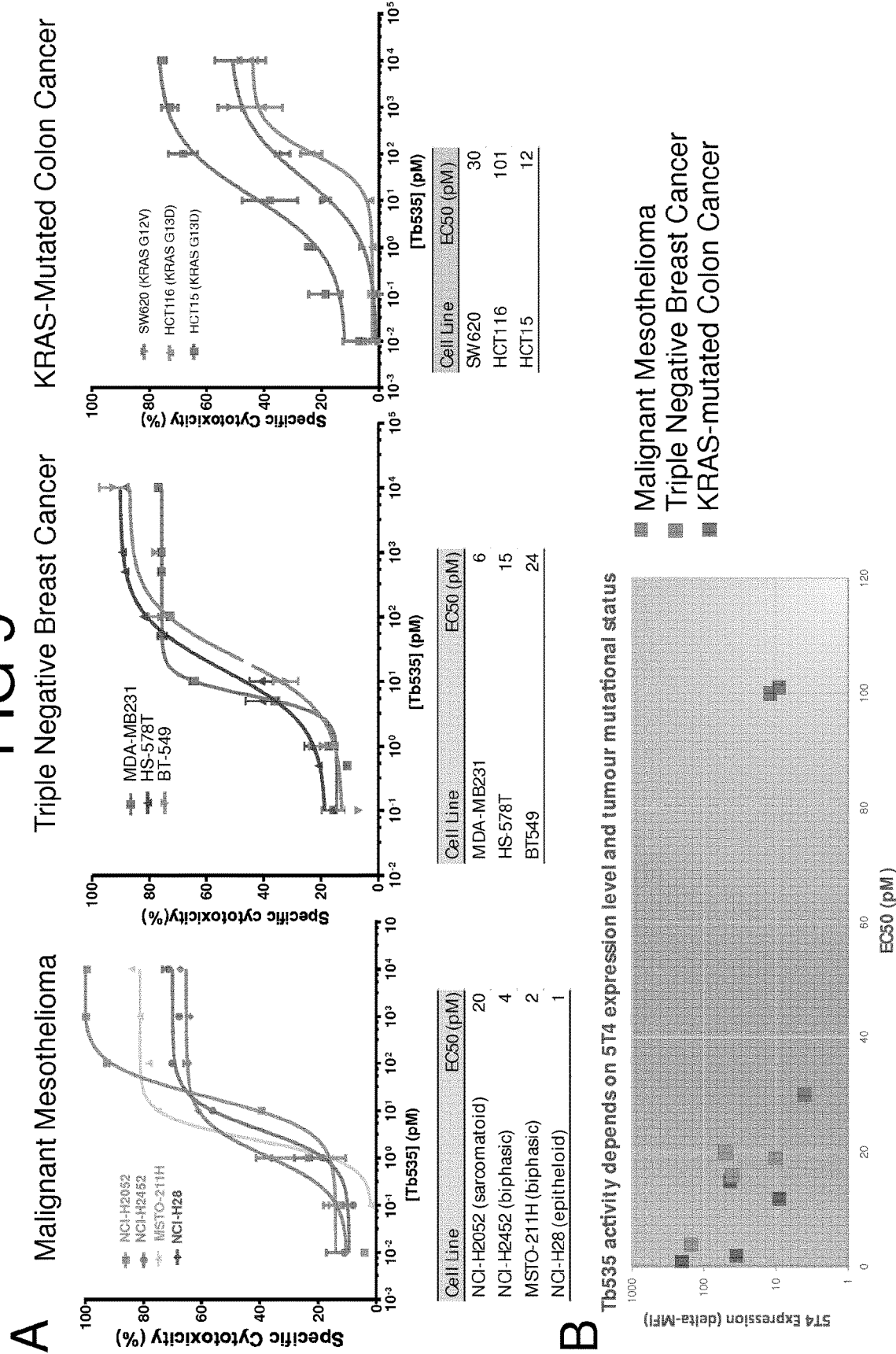

FIG. 9 Tb535H is active in a range of different tumor types

A: activity titration (induced killing of 5T4-positive tumor cells by human PBMC in mixed culture) of a Tb535 using cell lines representative of different forms of mesothelioma, triple negative breast cancer and KRAS-mutated colon cancer. EC50 values in picomolar concentrations are given.

B: comparison of 5T4 membrane expression level as determined by FACS-decoration with the EC50 values obtained in a cell killing assay.

FIG. 10

A: half life estimation of equilibration and elimination phases after injection in mouse C57BL/6. Blood was recuperated from sacrificed animals and the concentration of functional Tb535 measured using a cytotoxicity inducing activity assay. Estimates suggest a large volume of distribution and a slow clearing.

Figure 11A:
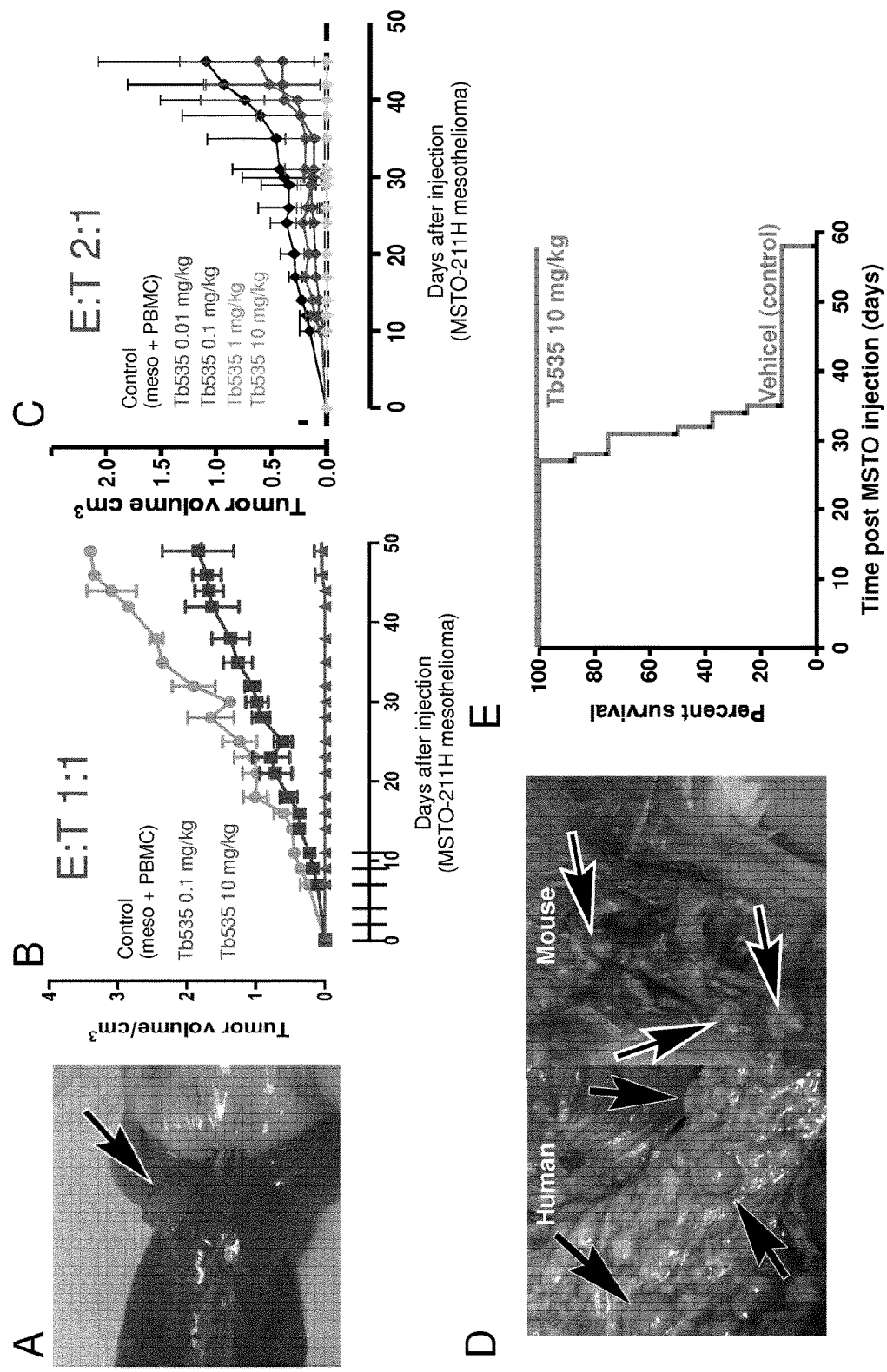

B: degradation of Tb535 could not be seen by probing whole blood protein with anti-FLAG tag Western blot analysis FIG. 11A Effectivity of Tb535 in a mesothelioma xenografted NOD/SCID mice reconstituted with human PBMC A: picture of mesothelioma tumour growing subcutaneously.

B: subcutaneous model and evolution of tumor growth at effector:target ratios of 1:1 various concentrations of Tb535H.

C: subcutaneous model and evolution of tumor growth at effector:target ratios of 2:1 at various concentrations of Tb535H.

D: picture of mesothelioma tumour growing orthotopic in mesothelium lining.

E: orthotopic induced mesothelioma in NOD/SCID mice mice reconstituted with human PBMC and treatment with Tb535H completely prevents formation of tumor and death (humane end point sacrifice).

FIG. 11B Treatment of established subcutaneous tumours after IP injection of 10E7 human PBMC and Tb535 on days indicated. Tumour volume was measured using a caliper.

Figure 12A:
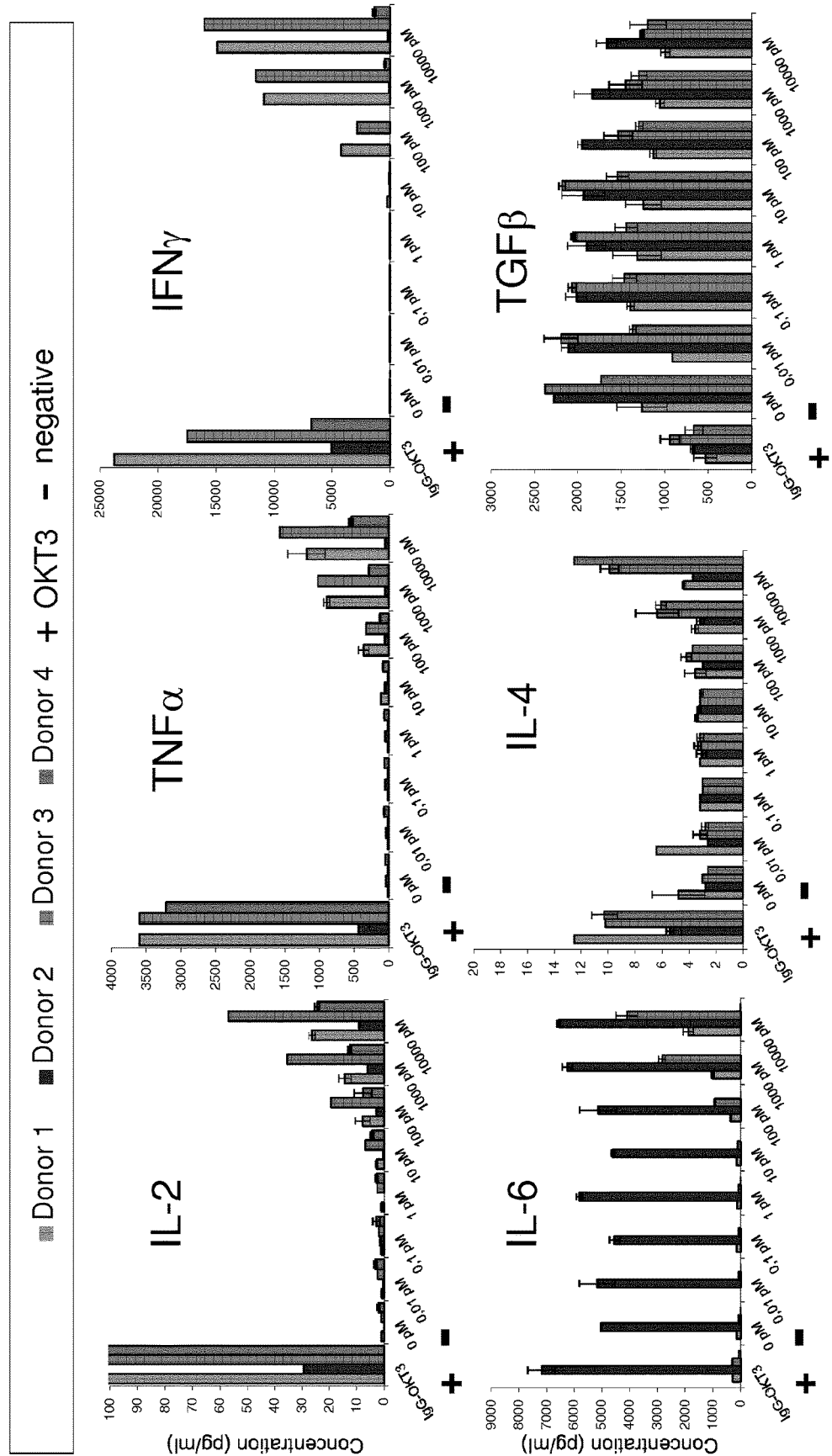

FIG. 12A Induction of TH1 cytokines by Tb535H in mixed cultures of tumor cells with PBMC. Especially IL-2, interferon-gamma and TNF-alpha are upregulated.

Positive controls are OKT3-IgG (muromomab-CD3) (+) and no additions (−).

Figure 12B:
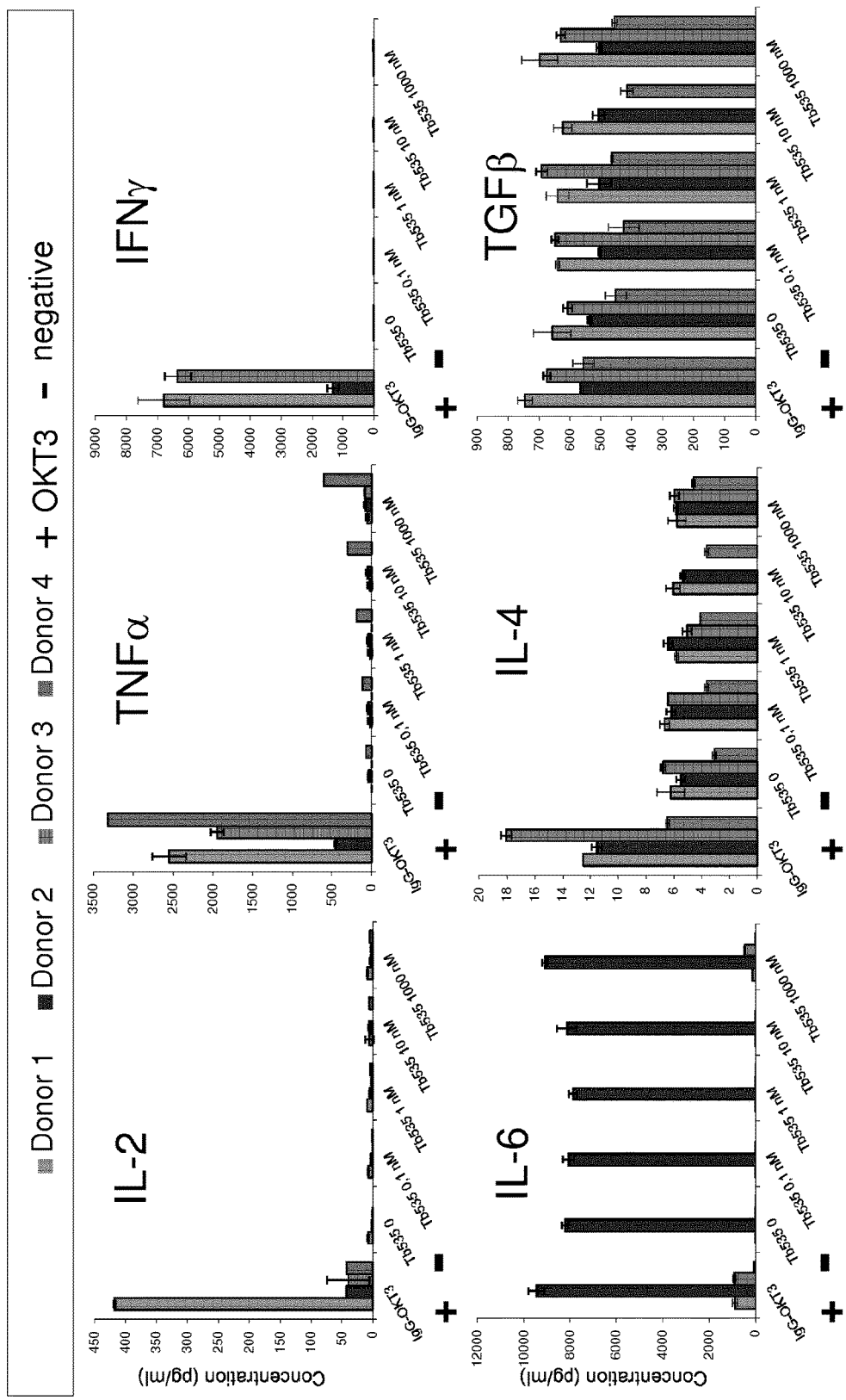

FIG. 12B Absence of cytokine induction of Tb535H incubation with PBMC from 3 human donors, up to Tb535H concentrations of 1 mM (milimolar).

Positive controls are OKT3-IgG (muromomab-CD3) (+) and no additions (−).

Figure 12C:
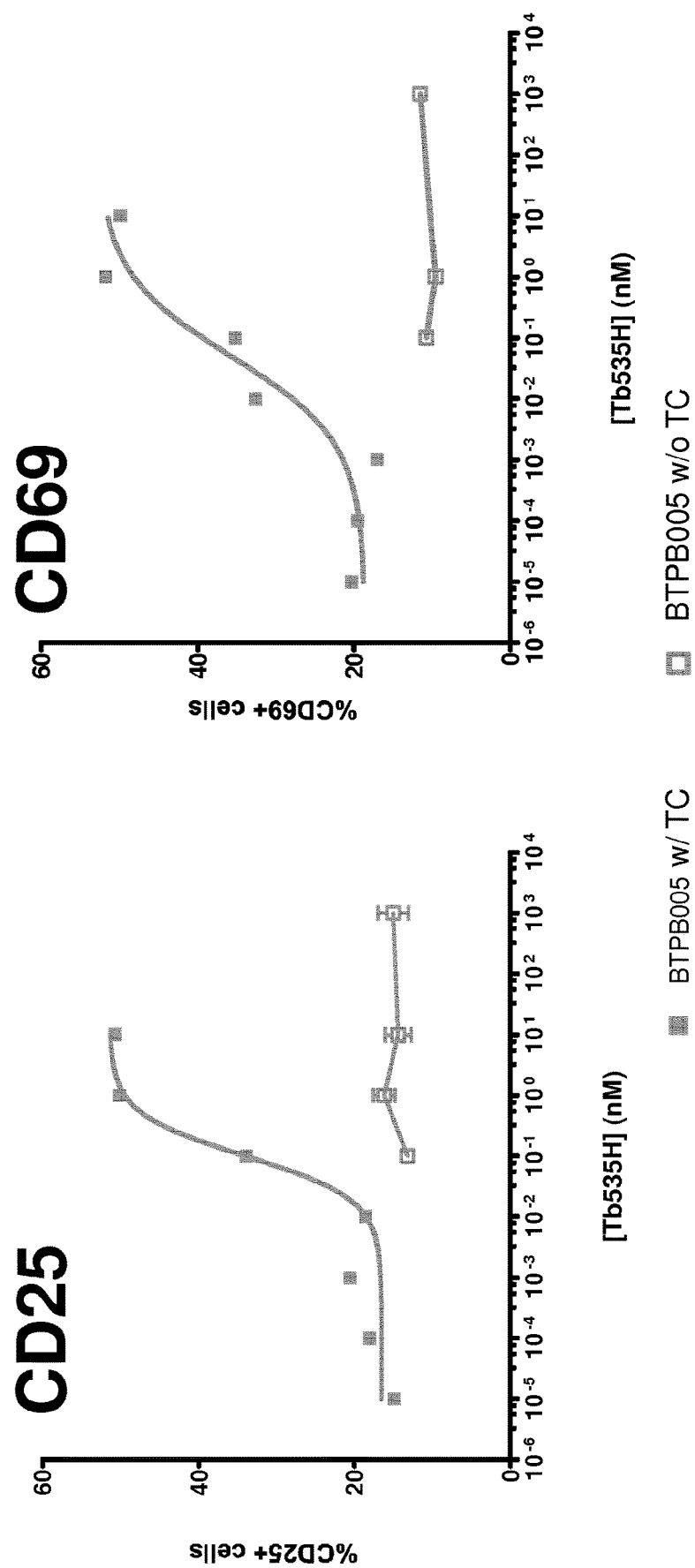

FIG. 12C Absence of T-cell activation marker induction (CD69 and CD25) on PBMC in the absence of 5T4-positive tumor cells up to 1 mM (milimolar) concentrations (open symbols). Closed symbols are controls in a mixed tumor cell/PBMC co-culture where the activation markers are induced starting at 10 000 fold lower concentrations.

FIG. 13 Analysis of main effector cells in human PBMC. Complete PBMC was compared with purified CD4-positive T-cell fraction, a CD8-positive T-cell fraction, a combination of both and a CD56positive NK cell fraction.

Figure 14A:
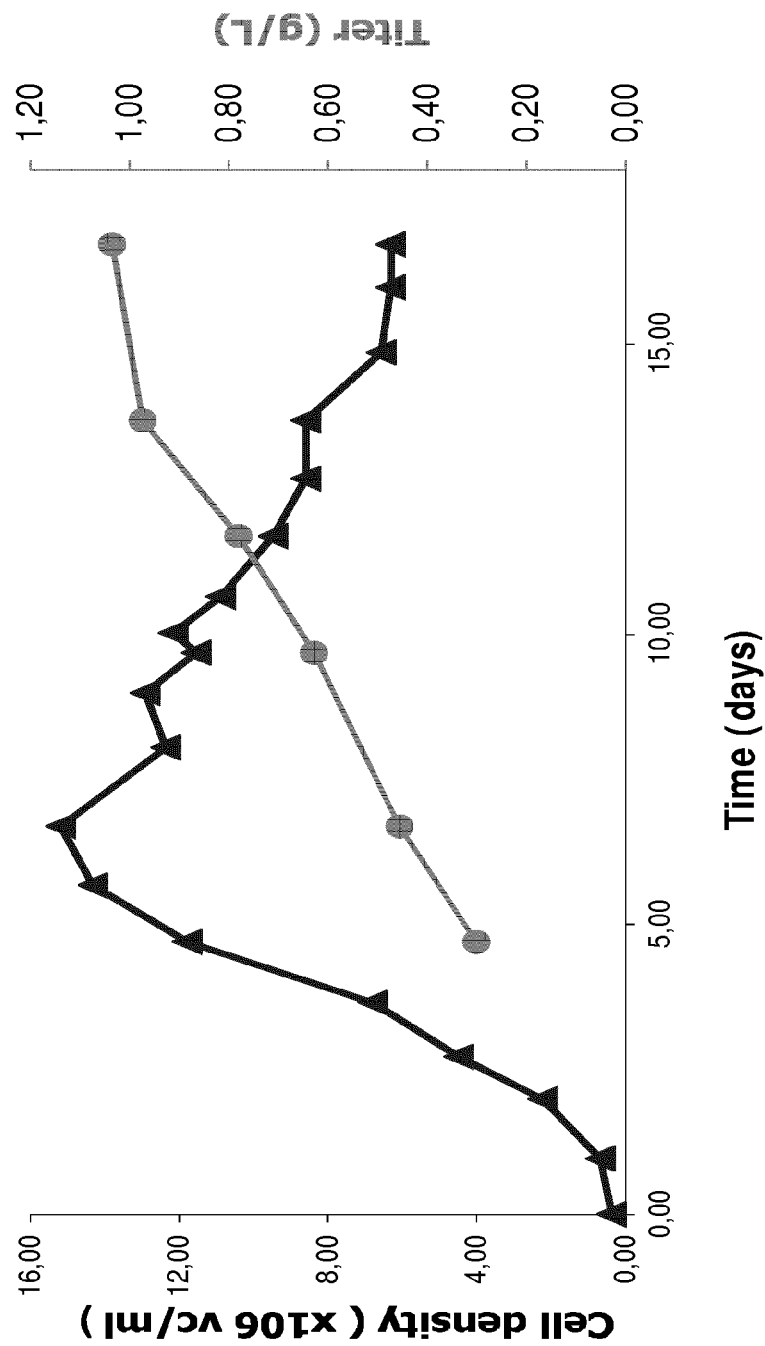

FIG. 14A TB535 is produced from stable CHO clones at up to 1 g/L in a fed batch bioreactor process using chemically defined medium and feeds.

Figure 14B:
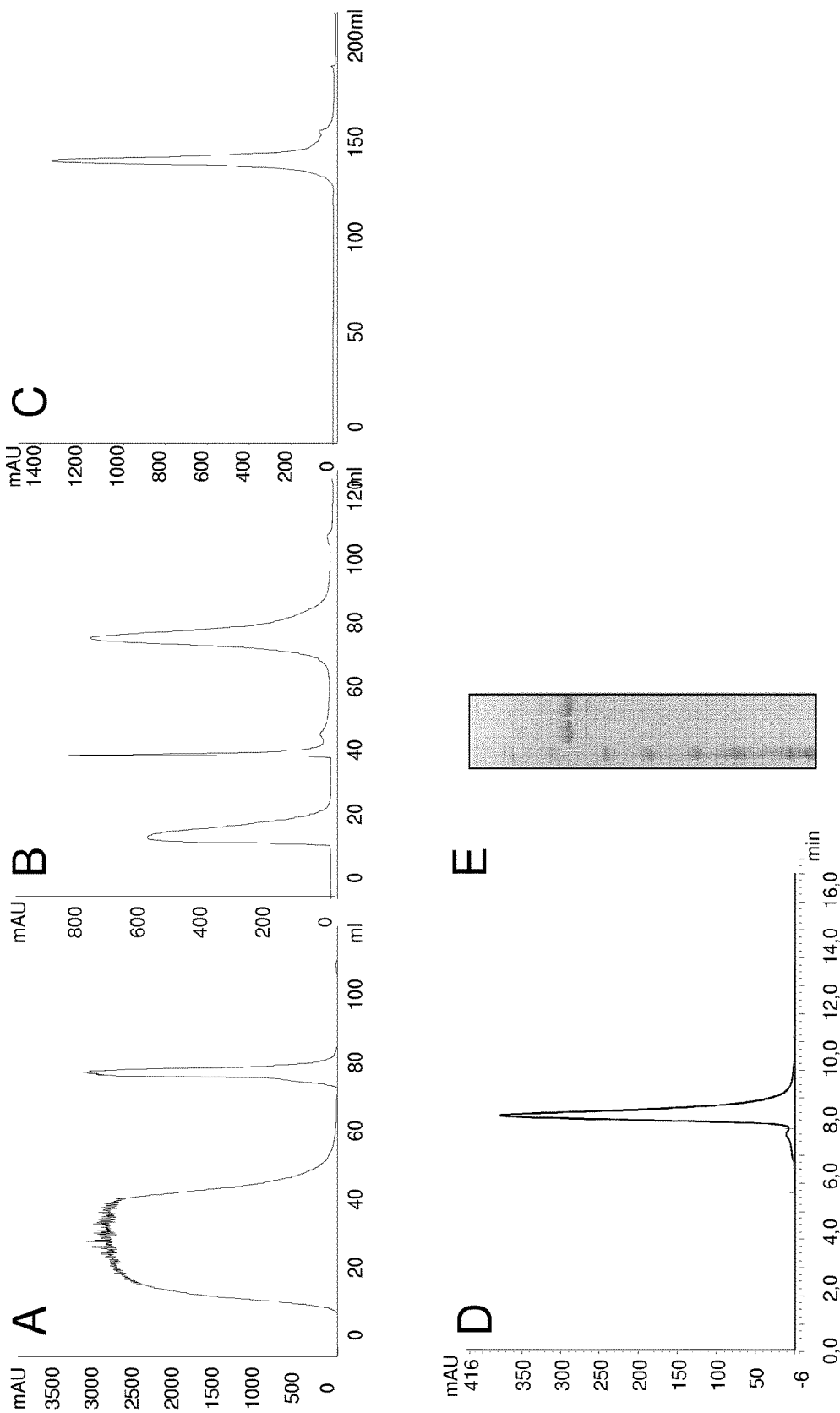

FIG. 14B Isolation of Tb535 from spent medium using a capture (A), purification (B) and polishing (C) step. Gel filtration analysis (D) and SDS-PAGE stained with Coomassie Brilliant Blue.

The following examples have been included to illustrate modes of the invention. Certain aspects of the following examples are described in terms of techniques and procedures found or contemplated by the present co-inventors to work well in the practice of the invention. These examples illustrate standard laboratory practices of the co-inventors. In light of the present disclosure and the general level of skill in the art, those of skill will appreciate that the following examples are intended to be exemplary only.

EXAMPLE 1 EXPRESSION

Transient Expression in HEK 293 Cells

Clones of the expression plasmids with sequence-verified nucleotide sequences were used for transfection and protein expression in the FreeStyle-293 Expression System (Invitrogen GmbH, Karlsruhe, Germany) according to the manufacturer's protocol. Supernatants containing the expressed proteins were obtained, cells were removed by centrifugation and the supernatants were stored at −20 C. Different permutations of 5T4 and CD3 binders according to position (e.g. FIG. 1B: i-iii)) and/or the use of a VH-VL or VL-VH combination for the scFv molecules (e.g. FIG. 1B iv-vi), or with crossed V-domains in the Fab (e.g. FIG. 1C vii-xii), or combined with domain binders (e.g. FIG. 1D xiii-xviii) were constructed at gene level and cloned in pES33 vector combining CMV promoter and a Kozak translation initiation site amongst other features. All constructs were fused C-terminally with a HIS-tag (HHHHHH) and N-terminally with a FLAG-tag (DYKDDDDK). Spent medium was analysed either after TCA precipitation of IMAC capture, followed by SDS-PAGE and Western Blot analysis probed with either anti-HIS antibody, anti-FLAG antibody, anti-human Fab or anti-human kappa serum. Proteins were purified using a combination of IMAC capture, ion exchange purification and a polishing step on gel filtration to assure isolation of a strict monomeric fraction. Various forms of 5T4×CD3 bispecific antibodies were compared in both Tribody (i.e. Fab-(scFv)2) or BiTE (i.e. scFv-scFv) format and scored for relative yield and relative fraction of monomeric protein produced. Tribody forms were found to generally yield more bispecific protein and a higher fraction of monomeric protein (see FIGS. 7A, 7B and 7C).

Stable Expression in CHO Cells

Clones of the expression plasmids with sequence-verified nucleotide sequences were transfected into DHFR deficient CHO cells for eukaryotic expression of the constructs. Eukaryotic protein expression in DHFR deficient CHO cells was performed as described by Kaufman R. J. (1990) Methods Enzymol. 185, 537-566. Gene amplification of the constructs was induced by increasing concentrations of methotrexate (MTX) to a final concentration of 20 nM MTX. After two passages of stationary culture the cells were grown in roller bottles with nucleoside-free HyQ PF CHO liquid soy medium (with 4.0 mM L-Glutamine with 0.1% Pluronic F-68; HyClone) for 7 days before harvest. The cells were removed by centrifugation and the supernatant containing the expressed protein was stored at −20 C.

A stable TB535 expressing cell line is created using serum/animal component free suspension adapted CHO cells. The Fd and L genes of the Tribody are cloned into vectors and co-transfected into the CHO cells. The plasmids contain selectable markers with elements to generate high levels of expression. From expressing pools a limiting dilution cloning is carried out to select for highest yielding most stable clones. TB535 is produced from stable clones at up to 1 g/L in a fed batch bioreactor process using chemically defined medium and feeds. FIG. 14A illustrates cell growth and TB535 titre for a typical TB535 bioreactor process.

The bioreactor is harvested with cell removal by depth filtration. TB535 is recovered and purified from the clarified spent medium phase using a combination of chromatography steps e.g. affinity, ion exchange and size exclusion, FIG. 14B, followed by a final concentration/diafiltration into formulation buffer for storage. This purification process yields circa 400 mg/l of purified stably formulated TB535 Tribody. As determined by a number of analytical methods including, as illustrated in FIG. 14B-D/E, analytical Size Exclusion and non-reducing SDS PAGE, TB535 produced by this process is >98% pure.

Expression of Recombinant Form of Soluble Human 5T4

The coding sequence of human 5T4 (GenBank, accession number NM 006670) was used for the construction of artificial cDNA sequence encoding soluble protein of human 5T4 comprising only the extracellular domains of 5T4.

For the fusions with human albumin, the modified cDNA fragments were designed as to contain first a Kozak site for eukaryotic expression of the constructs followed by the coding sequence of the human 5T4 protein comprising the amino acids 1 to 355 corresponding to the signal peptide and extracellular domain, preceded in frame by the coding sequence of a Flag tag, followed in frame by the coding sequence of a modified histidine tag (SGHHHHHH) and a stop codon.

The aforementioned procedures were all carried out according to standard protocols (Sambrook, Molecular Cloning; A Laboratory Manual, 3rd edition, Cold Spring Harbour Laboratory Press, Cold Spring Harbour, N.Y. (2001)).

EXAMPLE 2 HUMANIZATION

Figure 2:
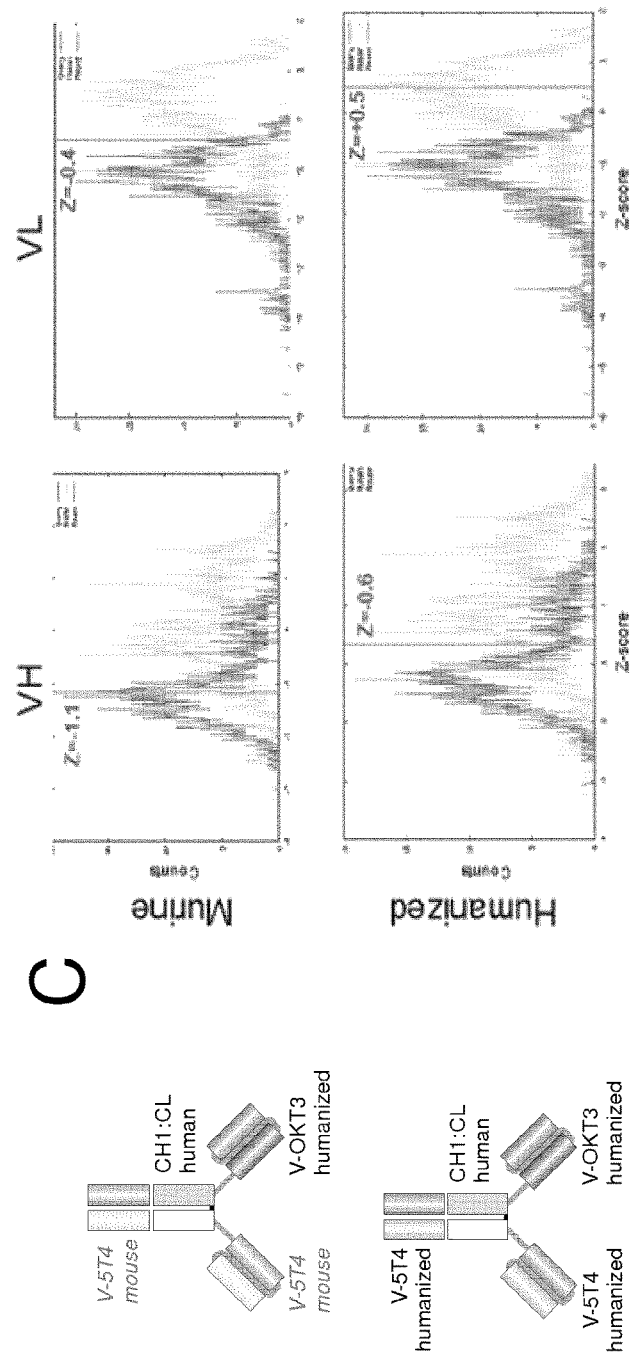

Chimeric and humanized anti-5T4 antibodies were prepared using sequences derived from the murine H8 antibody and human antibody sequences. Some sequences of representative antibodies of the invention are shown in FIG. 2.

Chimeric H8 antibodies were constructed having murine H8 heavy chain and light chain variable regions sequences (e.g. SED ID 01 or SEQ ID 02 combined with either SEQ ID 16 or SEQ ID 17 and human constant regions sequences CH1 and CL-kappa. Representative human constant regions that were used to prepare chimeric and humanized H8 antibodies include those of human IgG1, human kappa, and human IgG4. For cloning of sequences encoding IgG constant regions, intronic sequences may optionally be deleted. Antibodies were also prepared wherein one antibody chain comprises the murine H8 variable region (as in a chimeric antibody) and the other antibody chain comprises a humanized H8 variable region, i.e., a semi-humanized antibody.

Humanized H8 variable regions were constructed to include the CDRs of murine H8 grafted onto human or substantially human framework regions. The CDRs of the murine H8 antibody were identified using the AbM definition, which is based on sequence variability as well as the location of the structural loop regions. Human acceptor frameworks were selected on the basis that they were substantially similar to the framework regions of the murine H8 antibody, or which were most similar to the consensus sequence of the variable region subfamily. See FIG. 2. Consideration was also given to representation of the framework loci in humans, such that widely represented sequences were preferred over less populous sequences. Additional mutations of the human framework acceptor sequences were made, for example to restore murine residues believed to be involved in antigen contacts and/or residues involved in the structural integrity of the antigen-binding site. The amino acid sequence was also optimized for codon preference of CHO cells and to remove restriction enzyme sites. A peptide structure prediction program was used to analyse the humanized variable heavy and light region sequences to identify and avoid post-translational protein modification sites introduced by the humanization design. Using this strategy, three versions of humanized H8 variable regions were constructed. Version 1 retains murine H8 residues at positions within the framework sequence believed to be critical for antibody integrity and antigen binding. Version 2 retains murine residues only in the CDRs. Version 3 is similar to version 2, with the exception that a consensus variable region sequence was used as the heavy chain acceptor framework. The light chain variable region of the version 3 antibody is the same as that of the Version 2 antibody.

For construction of humanized H8 light chain variable regions, the DPK24 germ line sequence VL-IV/locus B3 was used as the acceptor framework. The DPK24 sequence is 68% identical to the murine H8 light chain variable region and contains 18 amino acid substitutions when compared to the murine H8 light chain framework sequences. Humanized antibodies were also constructed using framework regions of the light chain variable region of germline clone subgroups VκIII and VκI. In particular, antibodies that include light chain VκIII subgroups framework regions and the disclosed humanized H8 antibody version 1 are both highly expressed and stable.

For construction of humanized H8 heavy chain variable regions, the DP75 germ line sequence VH-I/locus 1-02 was used as the acceptor sequence. The DP75 sequence is 65% identical to the murine H8 heavy chain variable region and contains 28 amino acid substitutions when compared to the murine H8 heavy chain framework sequence. Humanized H8 heavy chain variable region version 1 maintained murine H8 residues K38 and S40, which are important for antigen contact with the heavy chain and light chain variable regions, as well as I48, which is important for antigen contact with the variable regions and with CDR2. Alternatively, humanized H8 heavy chain was prepared using a heavy chain variable region subgroup consensus sequence. The consensus sequence contains 25 amino acid substitutions when compared to the murine H8 heavy chain framework sequence.

The humanized H8 heavy chain and light chain variable regions were constructed by annealing together overlapping oligonucleotides and ligating them into the pUC57 cloning vector containing a human antibody constant region. Humanized heavy chain and light chain variable regions may also be constructed using PCR mutagenesis or site-directed mutagenesis. Design of the oligonucleotides included optimization of codon usage for CHO cell expression and removal of restriction enzyme sites.

Figure 4B:
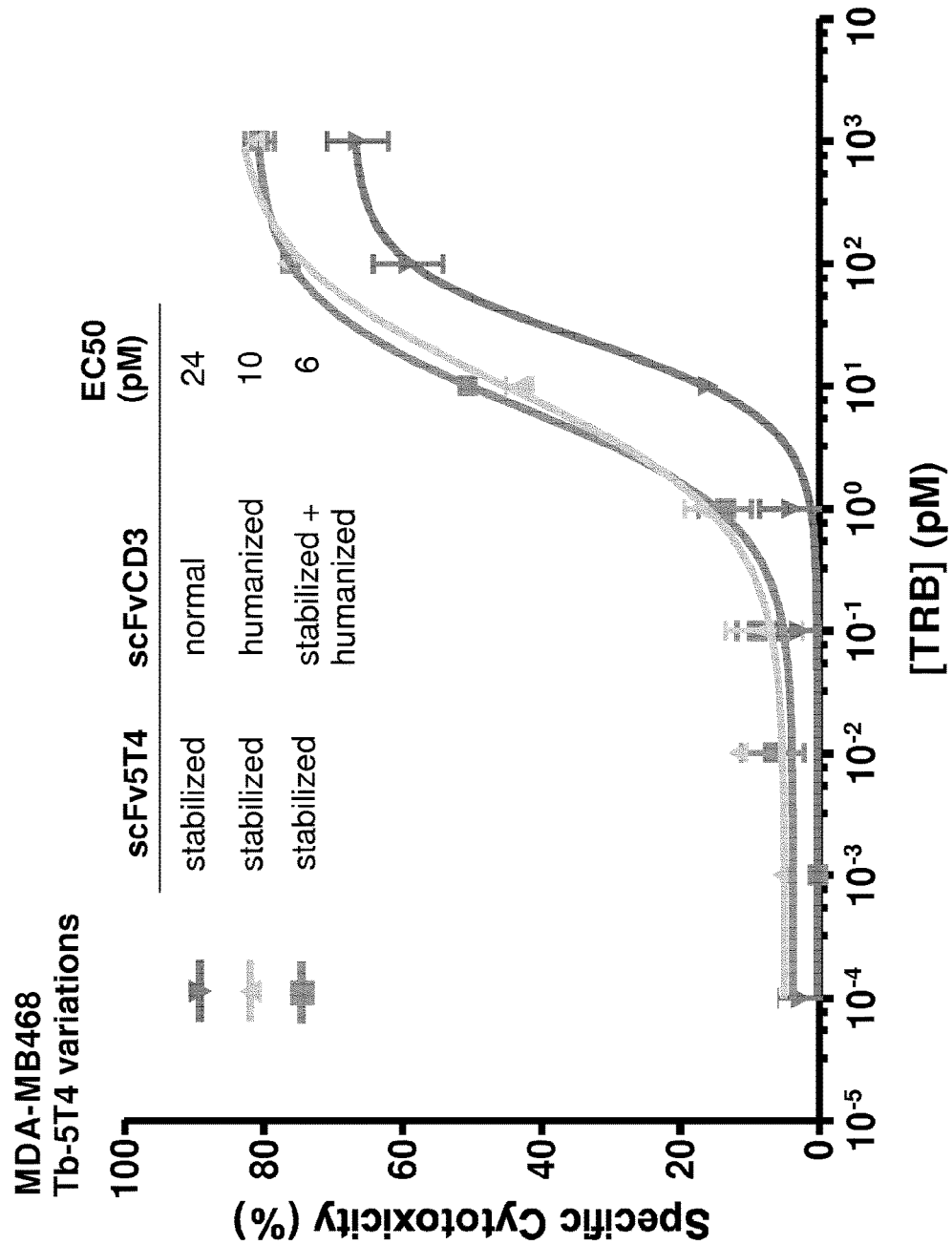

A further optimization was performed by substituting either VH CDR1, VH CDR2, VL CDR1 or VL CRD2 with a closest homologous germline sequence. Variants were ranked according to yield and binding activity. The VH CDR1 substitution is of particular interest since it had an unexpected enhancement of the number of molecules that effectively formed a stabilizing disulfide bond in the scFv as described in EP0703926 (see FIG. 4A and FIGS. 4B-A, B and C).

FIG. 5 shows analysis based on Gel Filtration, MALDI-TOFF and analytical ion exchange showing expected behaviour and comparability of the humanized form with the mouse based antibody (FIG. 5B, C, D). Analytical gel filtration again indicates a slightly more compact form of Tb535H (humanized) as compared with Tb535C (chimeric: containing mouse V-domains).

FIG. 8 shows comparable binding to 5T4 as well as CD3 and comparable activity of Tb535H (based on SEQ ID 06 and SEQ ID 19) as compared to a Tribody based on the murine variable domains (SEQ ID 02 and SEQ ID 17).

EXAMPLE 3 BINDING ASSAYS

FACS Analysis: Decoration, Titration, PBMC Binding

The cell lines to be tested (tumour cell lines, PBMCs) were collected (1×10<6> cells/sample), washed in PBS and incubated with 1 µg of the binding molecules (e.g, antibody/Tribody) in PBS/10% FBS for 1 hour on ice. For the characterization of the 5T4 expression by tumour cell lines a commercial anti-5T4 antibody was used (Cat-No: MAB49751, R&D Systems).

To access the binding of anti-5T4 molecules (scFv, Fab and Tribody format) to the human 5T4 domain, the biphasic mesothelioma cell line MSTO-211H (ATCC CRL-2081) was tested by FACS binding assay with direct labelled molecules with Allophycocyanin (APC) by the Lightning-Link® APC kit from Innova Biosciences, following the manufacturer instructions. For the determination of equilibrium dissociation constant (KD) the Tb535 concentrations were ranging from 0,05 to 500 nM.

Cells are then washed twice with PBS and binding to cell surface is accessed by flow cytometry using a BD FACsalibur apparatus.

Jurkat Cell-Based ELISA

To access the binding of the structures to the human CD3 domain, a cell based ELISA T-cell lymphoma (CD3+) cell line was used. Jurkat cells are collected, washed and aliquoted into each well of a round-bottom ELISA plate. Tribody and single chains dilutions were prepared in PBS and added to the cells. Following a wash step, detection antibody is added to the samples (alkaline phosphatase conjugated monoclonal anti-FLAG, Cat-No: A9469, Sigma). Secondary antibody is detected by development of a colorimetric reaction upon addition of p-NPP (Cat-No: N7653, Sigma) and the absorbance quantified on a microwell plate reader and processed by non-linear regression using graph Pad Prism software.

Cell-based or protein based ELISA was performed according to standard protocols (Sambrook, Molecular Cloning; A Laboratory Manual, 3rd edition, Cold Spring Harbour Laboratory Press, Cold Spring Harbour, N.Y. (2001)).

For Affinity to the human CD3 domain, a cell based ELISA with a T-cell lymphoma (CD3+) cell line, Jurkat, was used. Jurkat cells are collected, washed and aliquoted into each well of a round-bottom 96 well microplate. Tribody/sample dilutions were prepared in PBS, added to the cells and incubated. Following wash steps, detection antibody is added to the samples (anti-human Kappa light chain AP; e.g. Sigma, Cat. No. K4377). Bound detection antibody is measured by development of a colorimetric reaction upon addition of p-NPP (Cat-No: N7653, Sigma) and the absorbance quantified on a micro-well plate reader and processed by non-linear regression using graph Pad Prism software.

For Affinity to 5T4 target antigen an ELISA with the 5T4 antigen is used. Target antigen, 5T4 extra cellular domain, produced in house is coated to polystyrene flat bottom 96 well microplate and blocked. Tribody/sample dilutions were prepared in TBS with 0.2% w/v powdered milk, added to the plate and incubated. Following wash steps, detection antibody is added to the samples (anti-human Kappa light chain AP; e.g. Sigma, Cat. No. K4377). Bound detection antibody is measured by development of a colorimetric reaction upon addition of p-NPP (Cat-No: N7653, Sigma) and the absorbance quantified on a micro-well plate reader and processed by non-linear regression using graph Pad Prism software.

TABLE 1 affinity of various formats binding to 5T4 recombinant protein.
KD (ELISA on 5T4-ECD)

| | |
|---|---|
| dsFv | 2.3 nM |
| BiTE | 2 nM |
| Fab | 2.9 nM |
| Tb535H | 0.9 nM |
| Tb535C | 1 nM |
| IgG | 0.7 nM |

As shown in table 1, the bivalent binding Tb535 has a 2-3 fold higher affinity as compared to monovalent formats such as the comparable BiTEs (scFv-scFv format). Using the Tribody format affinities for 5T4 close to the IgG format are obtained (see FIGS. 3A, B and C). FIGS. 3 C and D shows a clear advantage in binding of Tribody over monovalent forms such as scFv and Fab.

The anti-CD3 binding in the Tb535 configuration remains effective as demonstrated by binding to Jurkat cells as well as to PBMC of different donors (FIG. 3F)

EXAMPLE 4 ACTIVITY ASSAYS

Target Cell Labelling

For the analysis of cell lysis in flow cytometry assays, the fluorescent membrane dye DiOCi8 (DiO) (Molecular Probes Cat-No: V22886) was used to label human or macaque 5T4-transfected CHO cells or 5T4-expressing human cells as target cells and distinguish them from effector cells. Briefly, cells were harvested, washed once with PBS and adjusted to $10^{<6>}$ cell/mL in PBS containing 2% (v/v) FBS and the membrane dye DiO (5 µl/$10^{<6>}$ cells). After incubation for 3 min at 37° C., cells were washed twice in complete RPMI medium and the cell number adjusted to 1.25×$10^{<5>}$ cells/mL. The vitality of cells was determined using 0.5% (v/v) isotonic EosinG solution (Roth Cat-No: 45380).

FACS-Based Cytotoxicity Assay with Human PBMC

Human peripheral blood mononuclear cells (PBMC) were prepared by Ficoll density gradient centrifugation from enriched lymphocyte preparations (buffy coats), a side product of blood banks collecting blood for transfusions. Buffy coats were supplied by a local blood bank and PBMC were prepared on the same day of blood collection. After Ficoll density centrifugation and extensive washes with Dulbecco's PBS (Gibco), remaining erythrocytes were removed from PBMC via incubation with erythrocyte lysis buffer (155 mM NH4CI, 10 mM KHC03, 100 mM EDTA). Platelets were removed via the supernatant upon centrifugation of PBMC at 100×g. Remaining lymphocytes mainly encompass B and T lymphocytes, NK cells and monocytes. PBMC were kept in culture at 37° C./5% C02 in RPMI medium (Gibco) with 10% FCS (Gibco).

Bioactivity of the Tribodies was analysed by a FACS-based in vitro cytotoxicity assay using different tumour cell lines: MDA-MB468 (ATCC HTB-132), MSTO-211H (ATCC CRL-2081), NCI-H2052 (ATCC CRL-5915), NCI-H2452 (ATCC CRL-5946), NCI-H28 (ATCC CRL-5820), MDA-MB231 (ATCC HTB-26), HS-578T (ATCC HTB-126), BT-549 (ATCC HTB-122), SW-620 ATCC CCL-227), HCT-116 (ATCC CCL-247), HCT-15 (ATCC CCL-225) as target cells. Human PBMCs were used as effector cells after CD3/CD28/IL-2 stimulation. For stimulation a T-flaks (75 cm3) was coated with 5 µg/ml αCD3 (ImmunoTools Cat-No: 21620030,) in 7.5 ml PBS 1× for 2 h at 37° C. The flask was rinsed with PBS before whole PBMC were added in RPMI-1640 (Sigma Cat-No: R8758) supplemented with 10% FBS (PAA Cat-No: A15-151), 5 µg/ml αCD28 (ImmunoTools Cat-No: 21330280) and 30 U/mL of human recombinant IL-2 (ImmunoTools Cat-No: 11340023). After 3 days of stimulation at 37° C. and 5% CO2, PBMC were transferred to an uncoated T-Flask and incubated for another 24 h in RPMI-1640 with 10% FBS and 30 U/ml of IL-2 in order to allow internalized T cell receptor to be redelivered to cell surface. Target cells were labelled with PKH67 dye (Sigma Cat-No: MINI67-1KT) according to the manufacturer's instructions and incubated overnight for cell adhesion.

Human PBMCs (Tebu Cat-No: 192PMBC) were added at an Effector:Target ratio of 5:1 and Tribodies were prepared with a concentration range from 1000 to 0,001 ng/ml, in duplicate. Targets, effector cells and Tribody were incubated for 48 h at 37° C. and 5% $CO_2$. After incubation, cells were harvested and resuspended in PBS containing Propidium iodide (Sigma Cat-No: P4864), except for the cells with no Tribody. Specific cytotoxicity was determined as a function of intact living targets cells (PKH67+ cells) over dead cells (PI+).

Cells were accessed by flow cytometry using a BD FACsalibur apparatus and using cell quest software. For determination of estimated Tribody concentration at which half-maximal lysis of target cells occurred (EC50), specific cytotoxicity values were plotted against Tribody concentration and processed by non-linear regression using Graph-Pad Prism software.

Activity of Tb535 5T4×CD3 Tribody was always in the low-picomolar range measured in a series of cell lines representing several cancerous indications (e.g. FIGS. 9A and B). Surprisingly, a 5T4×CD3 Tribody showed a higher percentage of cell killing as compared to the BiTE scFv-scFv format, even when measured in vitro under saturating binding conditions (see FIG. 7D).

Detection of T-Cell Activation Markers

PBMCs a healthy donors (Tebu-Bio) were incubated with TB535H in the presence and absence of target MSTO-211H cells in duplicate. PBMCs were defrosted and incubated in RPMI for 24 h at 37° C. and 5% CO2. MSTO-211H cells were seeded at 8×104 cells/well in the 24-well plate and incubated overnight for cell adhesion. PBMC were added at an effector:target of 10:1 (non-activated) with a range of Tribody concentrations.

After 24 h incubation of hPBMC and Tribody in the present and absence of MSTO-211H cell line, PBMCs (supplier: Tebu-Bio) were harvested by centrifugation (300× g, 5 minutes, room temperature) and stained with APC-labelled anti-CD69 (Immunotools Cat-No: 21270564) and FITC conjugated anti-CD3 (Immunotools Cat-No: 21620033), at a concentration of 1 μg antibody/million cells. For determination of CD25, another T-cell activation marker, cells were harvested after 48 incubation and stained with APC-anti-CD25 (Immunotools Cat-No: 21270256) and FTIC anti-CD3. Antibodies were incubated for 1 hour at 4° C. in the dark. Cells were washed 3 times in PBS and results accessed by flow cytometry in a FACSCalibur apparatus.

FIG. 12C shows that ex-vivo co-culture of tumour cells with PBMC induces Tb535 concentration dependent T-cell activation marker expression, while this is not present in the absence of target cells even in concentrations up to 1 μM.

Cytotoxicity Assay with CD4+, CD8+ and NK Subpopulations

Commercially available CD4+, CD8+ and CD56+ enriched cells were purchased (Supplier: Tebu-bio) in order to evaluate the cytotoxic activity of CD4+ T-helper cells, CD8+ effector T-cells and NK cells.

The bioactivity of Tb535H was evaluated by a FACS-based in-vitro cytotoxicity assay with an alteration on the preparation of effector cells. Identically to the PBMC, these cell populations were also thawed and cultured overnight before being used in the cytotoxicity assay. However, instead of using a fixed E:T ratio of 10:1, as for the PBMC, the amount of effector cells was adapted for each cell subpopulation. Typically, CD4+ T-helper cells, CD8+ effector T-cells and NK cells represent 50%, 25% and 10% of the full population of PBMC. With this assumption the E:T ratios used in this cytotoxicity assay were 5:1 for CD4+ T-helper cells, 2,5: 1 for CD8+ effector T-cells and 1:1 for NK cells. As a control the assay was also performed with the full population of PBMCs at a E:T of 10:1. Additionally, a mixing of CD4+ and CD8+ cells was also tested.

The cytotoxic activity of these cell populations was determined with the incubation of Tb535 at 100.000 pM. Specific cytotoxicity was determined as a function of intact living targets cells (PKH67+ cells) over dead cells (PI+).

As demonstrated in FIG. 13 CD8+ T cells are the main effector cells, and the effectivity is enhanced by inclusion of CD4+ cells. NK cells are not stimulated to kill the target cells by Tb535.

EXAMPLE 5 STABILITY

Thermofluor Analysis

The scFv-PO3 and scFv-SP34 samples were diluted in PBS pH 7.4 to a final concentration of 0.1 mg/ml. 5 μl of 200× diluted Sypro Red gel stain (Cat-No: S-6653, Invitrogen) were added to 55 μl of diluted sample. 20 μl of each prepared sample was loaded to a capillary and centrifuged, 700 g for 5 s. For detection, the thermocycler (Roche Lightcycler 1.5) was set at 640 nm and programmed with a first step at 37° C. for 10 s followed by rising up to 95° C. at 0.5° C. per second with continuous data acquisition.

Analytical Size Exclusion (Gel Filtration).

Analysis to quantify Tribody and determine purity, proportion of monomer vs higher molecular weight soluble aggregated forms, e.g. dimers, trimer etc, and smaller molecular weight fragmented forms e.g. free light chains, was carried out on a Bio SEC-5, 5 um, 300A, 7,8×300 mm, column (Agilent) at 1 ml min$^{-1}$ with Sodium Phosphate/NaCl pH7.0 buffer on an Ultimate 3000 HPLC (Dionex) with detection by UV at 280 nm. Quantification is carried using AUC against a calibration curve generated using a purified standard.

Tribody formats—and especially when containing disulfide stabilized single chains—are found to be more stable than comparable scFv-scFv (BiTE) formats and surprisingly even when compared to an IgG format containing identical V-domain sequences (FIG. 6A-D).

The remarkable stability of Tb535 is further illustrated by incubation in either PBS or human serum for 3 days at 37° C. There is no change in monomeric soluble fraction (FIG. 6B-A) and no loss in activity (FIG. 6B-B).

EXAMPLE 6 ANALYSIS

Analytical Cation Exchange Analysis to characterize and determine proportion of charged isoforms was carried out on a MabPac SCX-10 3 μm, 4×50 mm, column (Thermofisher) at 0.5 ml min$^{-1}$ with MES pH 5.6 buffer using salt gradient elution on an Ultimate 3000 HPLC (Dionex) with detection by UV at 280 nm.

Isoelectric Focusing was carried out using non-equilibrium pH gel electrophoresis using IEF 3-10 precast gels (Serva) run in a XCell Surelock Mini-Cell (Invitrogen) with BIO-RAD Power Pac HV and stained with SimplyBlue SafeStain (Invitrogen)

SDS PAGE was carried out on NuPAGE Novex Bis-Tris 4-12% gels (Invitrogen) run in a XCell Surelock™ Mini-Cell (Invitrogen) with BIO-RAD Power Pac HV, MOPs buffer, and stained with SimplyBlue™ SafeStain (Invitrogen). For analysis samples were diluted with loading buffer, NuPAGE LDS (Invitrogen) and for reducing SDS PAGE additionally reduced with DTT.

For Western Blots sample are first separated by non-reducing SDS PAGE, NuPAGE Novex Bis-Tris 4-12% gels (Invitrogen) run in a XCell Surelock Mini-Cell (Invitrogen) with BIO-RAD Power Pac HV, MOPs buffer, transferred to a PVDF membrane and detected using anti-human Kappa light chain AP; e.g. Sigma, Cat. No. K4377. Bound detection antibody is developed using a AP conjugate kit, Cat. No. 170-6432, Biorad.

EXAMPLE 7 PHARMACOKINETICS AND PHARMACODYNAMICS IN MOUSE MODELS

Determination of Half-Life Via Cytotoxicity Assay 30 mice (FOXP3-GFP; mixed gender; 2 males and 1 female per time-point) were injected 10 mg/kg of Tb535 and sacrificed in groups of 3 mice at different time points: 5 and 30 min, 1, 2, 3, 4, 6, 8, 12 and 16 h post injection. The bioactivity of Tb535H in serum samples was evaluated by a FACS-based in-vitro cytotoxicity assay as previous described. Briefly, target cells (MSTO-211H) were labelled with PKH67 dye (Sigma-Aldrich) according to the manufacturer's instructions and incubated overnight for cell adhesion. Commercial Human Peripheral Blood Mononuclear Cells (PBMCs) were activated with CD3/CD28/IL2 and used as effector cells with an Effector to Target ratio of 5:1. For each serum sample 2 to 3 dilutions were prepared, added to the target cells and incubated for 72 h at 37° C. and 5% CO2. As a control, Tb535H samples with known concentration were also included to establish a calibration curve that correlates Tribody concentration with a cytotoxicity value for this specific PBMC donor. After incubation, cells were harvested and specific cytotoxicity was determined as a function of intact living targets cells (PKH67+ cells) over dead cells (PI+) as assessed by flow cytometry using a BD FACSCalibur apparatus and using cell quest software. For determination of estimated Tb535H concentration and half-life by this method specific cytotoxicity values were plotted against time and processed by linear regression considering an $\alpha$ and $\beta$ phase.

FIG. 10 shows an example of a half-life determination showing a large volume of distribution and relative slow clearance.

Determination of Effectivity: Early Treatment

To test the efficacy of Tribody (10; 1; 0.1; 0.01 mg/kg) on an early tumor model, NOD/SCID mice were sub-cutaneous injected with $2.5 \times 10^6$ mesothelioma tumour cells mixed with $2.5 \times 10^6$ or $5 \times 10^6$ human PBMC. Tribody was given i.v. at days 0, 2, 4, 7, 9 and 11 post-tumour injection. Tumour growth was measured with a calliper.

To mimic an orthotopic mesothelioma model $2.5 \times 10^6$ mesothelioma tumour cells were intra-pleurally injected. Animals were checked regularly for breading difficulties and >20% weight loss to determine humane end points as approved by local ethical committee.

FIG. 11A-ABC shows the effectivity of Tb535 in treatment of subcutaneous xenografted NOD/SCID mice reconstituted with human PBMC, and FIGS. 11A-D and E illustrates activity in an orthotopic (intra-pleural injected) mesothelioma tumour model.

Determination of Effectivity: Late Treatment

Treatment of established tumours was demonstrated usng xenograft studies in NSG mice (NOD-scid IL2Rgamma<null>, The Jackson Laboratory), seven days after subcutaneous implantation of $5.10^6$ cancer cells, mice were injected three times with $10.10^6$ activated PBMC every six days via IP. For all studies, two days after the initial PBMC infusion, mice were treated intravenously with seven doses of Tb535 or saline every other day. Tumours were measured twice a week with callipers, and tumor volume was calculated by W×L×H.

FIG. 11B shows Tb535 is also active against established tumours.

EXAMPLE 8 EX-VIVO CYTOTOXICITY

Cytokine Release Assay

PBMCs from 4 healthy donors were incubated with TB535H in the presence and absence of target MSTO-211H cells. PBMCs were defrosted and incubated in RPMI for 24 h at 37° C. and 5% CO2. MSTO-211H cells were seeded at 8×104 cells/well in the 24-well plate and incubated overnight for cell adhesion. PBMC were added at an effector: target of 10:1 (non-activated) with a range of Tribody concentrations. Upon 24 or 48 h incubation at 37° C. and 5% CO2, cells were harvested and centrifuged (300×g, 5 minutes, room temperature) ans supernatant was collected to a new tube and assayed for cytokine release.

Cytokine release into the culture medium was accessed by ELISA using the following kits, according to manufacturer's instructions: IL-2, Mabtech 3445-1H-6; IFN-gamma Mabtech 3420-1H-6; TNF-alfa Mabtech 3510-1H-6; TGF-beta 1 R&D DY240-05; IL-4 R&D DY204-05 and IL-6 R&D DY206. Some samples had to be diluted so that the result would fit into the standard curve, namely for TGF1-beta (1:7 dilution), IL-6 (1:10 dilution) and IFN-gamma (1:40 dilution in NOEL target samples for Tb535H concentrations of 10 ng/ml and higher). Samples were measured after 24 h incubation for quantification of IL-2, IFN-gamma, TNF-alfa and IL-6. IL-4 and TGF-beta 1 were quantifies from culture medium after 48 h incubation.

FIG. 12A shows cytokine induction in ex-vivo co-culture of tumour cells with PBMC of the type I response, and FIG. 12B shows lack of significant cytokine induction in the absence of target cells (only PBMC+Tb535).

TABLE 1

Amino Acid Sequences

| SEQ ID | Sequence |
| --- | --- |
| 01 | EVQLQQSGPDLVKPGASVKISCKASGYSFTGYYMHWVKQSHGKSLEWIGRI NPNNGVTLYNQKFKDKAILTVDKSSTTAYMELRSLTSEDSAVYYCARSTMIT NYVMDYWGVTTSVTVSS |
| 02 | EVQLQQSGPDLVKPGASVKISCKASGYSFTGYYMHWVKQSPGKGLEWIGRI NPNNGVTLYNQKFKDKATLTVDKSSTTAYMELRSLTSEDSAVYYCARSTMI TNYVMDYWGQGTSVTVSS |

TABLE 1-continued

Amino Acid Sequences

| SEQ ID | Sequence |
|---|---|
| 03 | QVQLVQSGAEVKKPGASVKVSCKASGYSFTGYYMHWVKQSPGQGLEWIGR<br>INPNNGVTLYNQKFKDRVTMTRDTSISTAYMELSRLRSDDTAVYYCARSTMI<br>TNYVMDYWGQGTLVTVSS |
| 04 | QVQLVQSGAEVKKPGASVKVSCKASGYSFTGYYMHWVRQAPGQGLEWMG<br>RINPNNGVTLYNQKFKDRVTMTRDTSISTAYMELSRLRSDDTAVYYCARST<br>MITNYVMDYWGQGTLVTVSS |
| 05 | QVQLVQSGAEVKKPGASVKVSCKASGYSFTGYYMHWVRQAPGQGLEWMG<br>RINPNNGVTLYNQKFKDRVTITRDTSTSTAYMELSSLRSEDTAVYYCARSTM<br>ITNYVMDYWGQGTLVTVSS |
| 06 | QVQLVQSGAEVKKPGASVKVSCKASGYSFTSYYMHWVKQSPGQGLEWIGR<br>INPNNGVTLYNQKFKDRVTMTRDTSISTAYMELSRLRSDDTAVYYCARSTMI<br>TNYVMDYWGQGTLVTVSS |
| 07 | QVQLVQSGAEVKKPGASVKVSCKASGYSFTGYYMHWVKQSPGQGLEWIG<br>WINPNSGGTNYAQKFQGRVTMTRDTSISTAYMELSRLRSDDTAVYYCARST<br>MITNYVMDYWGQGTLVTVSS |
| 08 | QVQLVQSGSELKKPGASVKVSCKASGYSFTGYYMHWVRQAPGQGLEWMG<br>RINPNNGVTLYNQKFKDKFVFSLDTSVSTAYLQICSLKAEDTAVYYCARSTM<br>TNYVMDYWGQGTLVTVSS |
| 09 | QVQLVQSGAEVKKPGASVKVSCKVSGYSFTGYYMHWVRQAPGKGLEWMG<br>RINPNNGVTLYNQKFKDKVTMTEDTSTDTAYMELSSLRSEDTAVYYCATST<br>MITNYVMDYWGQGTLVTVSS |
| 10 | IQMQLVQSGPEVKKPGTSVKVSCKASGYSFTGYYMHWVRQARGQRLEWIG<br>RINPNNGVTLYNQKFKDKVTITRDMSTSTAYMELSSLRSEDTAVYYCAAST<br>MITNYVMDYWGQGTLVTVSS |
| 11 | QVQLVQSGAEVKKPGASVKVSCKASGYSFTGYYMHWVRQAPGQRLEWMG<br>RINPNNGVTLYNQKFKDKVTITRDTSASTAYMELSSLRSEDTAVYYCARSTM<br>ITNYVMDYWGQGTLVTVSS |
| 12 | QVQLVQSGAEVKKPGSSVKVSCKASGYSFTGYYMHWVRQAPGQGLEWMG<br>RINPNNGVTLYNQKFKDKVTITADKSTSTAYMELSSLRSEDTAVYYCARST<br>MITNYVMDYWGQGTLVTVSS |
| 13 | QVQLVQSGSELKKPGASVKVSCKASGYSFTGYYMHWVRQAPGQGLEWMG<br>RINPNNGVTLYNQKFKDKVTITADKSTSTAYMELSSLRSEDTAVYYCARST<br>MITNYVMDYWGQGTLVTVSS |
| 14 | QVKLQQSGPGLVTPSQSLSITCTVSGYSFTGYYMHWVRQSPGQGLEWLGRI<br>NPNNGVTLYNQKFKDKKSISKDNSKSQVFLKMNSLQADDTAVYYCARSTMI<br>TNYVMDYWGQGTTVTVSS |
| 15 | QVQLQESGPGLVKPSQTLSLTCTVSGYSFTGYYMHWVRQPPGKGLEWIGRI<br>NPNNGVTLYNQKFKDKVTISVDTSKNQFSLKLSSVTAADTAVYYCARSTMI<br>TNYVMDYWGQGTLVTVSS |
| 16 | DIVMTQTPTFLLVSACDRVTITCKASQSVSNDVAWYQQKPGQSPTLLISYTSS<br>RYAGVPDRFIGSGYGTDFTFTISTLQAEDLAVYFCQQDYNSPPTFGGGTKLEI<br>K |
| 17 | ASIVMTQTPTSLLVSAGDRVTITCKASQSVSNDVAWYQQKPGQSPKLLISYT<br>SSRYAGVPDRFSGSGYGTDFTLTISSVQAEDAAVYFCQQDYNSPPTFGGGTK<br>LEIK |
| 18 | DIVMTQSPDSLAVSLGERATINCKASQSVSNDVAWYQQKPGQSPKLLISYTS<br>SRYAGVPDRFSGSGSGTDFTLTISSLQAEDVAVYFCQQDYNSPPTFGGGTKL<br>IEIK |
| 19 | DIVMTQSPDSLAVSLGERATINCKASQSVSNDVAWYQQKPGQPPKLLIYYTS<br>SRYAGVPDRFSGSGSGTDFTLTISSLQAEDVAVYYCQQDYNSPPTFGGGTKL<br>EIK |
| 20 | IDIVMTQSPDSLAVSLGERATINCRASQGIRNDLGWYQQKPGQPPKLLIYYTS<br>SRYAGVPDRFSGSGSGTDFTLTISSLQAEDVAVYYCQQDYNSPPTFGGGTKL<br>EIK |

TABLE 1-continued

Amino Acid Sequences

| SEQ ID | Sequence |
|---|---|
| 21 | DIVMTQSPDSLAVSLGERATINCKASQSVSNDVAWYQQKPGQPPKLLIYAAS SLQSGVPDRFSGSGSGTDFTLTISSLQAEDVAVYYCQQDYNSPPTFGGGTKL EIK |
| 22 | DIQMTQSPSSLSASVGDRVTITCKASQSVSNDVAWYQQKPGKAPKRLIYYTS SRYAGVPSRFSGSGSGTEFTLTISSLQPEDFATYYCQQDYNSPPTFGGGTKLEI K |
| 23 | DIVMTQSPDSLAVSLGERATINCKASQSVSNDVAWYQQKPGQPPKLLIYYTS SRYAGVPDRFSGSGSGTDFTLTISSLQAEDVAVYYCQQDYNSPPTFGGGTKL IEIK |
| 24 | EIVMTQSPSTLSASVGDRVIITCKASQSVSNDVAWYQQKPGKAPKLLIYYTSS RYAGVPSRFSGSGSGAEFTLTISSLQPDDFATYYCQQDYNSPPTFGQGTKLTV L |
| 25 | EIVLTQSPATLSLSPGERATLSCKASQSVSNDVAWYQQKPGQAPRLLIYDAS NRATGIPARFSGSGPGTDFTLTISSLEPEDFAVYYCQQRSNWHFGQGTKVEIK |
| 26 | QVQLVQSGGGVVQPGRSLRLSCKASGYTFTRYTMHWVRQAPGKGLEWIGY INPSRGYTNYNQKVKDRFTISRDNSKNTAFLQMDSLRPEDTGVYFCARYYD DHYCLDYWGQGTPVTVSS |
| 27 | QVQLVQSGGGVVQPGRSLRLSCKASGYTFTRYTMHWVRQAPGKGLEWIGY NPSRGYTNYNQKVKDRFTISRDNSKNTAFLQMDSLRPEDTGVYFCARYYD DHYSLDYWGQGTPVTVSS |
| 28 | DVQLVQSGAEVKKPGASVKVSCKASGYTFTRYTMHWVRQAPGQGLEWIG YINPSRGYTNYADSVKGRFTITTDKSTSTAYMELSSLRSEDTATYYCARYYD DHYCLDYWGQGTTVTVSS |
| 29 | QVQLVQSGAELKKPGASVKVSCKASGYTFTRYTMHWVRQAPGQCLEWMG YINPSRGYTNYNQKFKDKATLTADKSTSTAYMELRSLRSDDTAVYYCARYY DDHYSLDYWGQGTLVTVSS |
| 30 | QVQLVESGGGVVQPGRSLRLSCAASGFKFSGYGMHWVRQAPGKGLEWVA VIWYDGSKKYYVDSVKGRFTISRDNSKNTLYLQMNSLRAEDTAVYYCARQ MGYWHFDLWGRGTLVTVSS |
| 31 | QVQLQQSGAELARPGASVKMSCKASGYTFTSYTMHWVKQRPGQGLEWIGY INPS SGYTKYNQKFKDKATLTADKSSSTAYHQLSSLTSEDSAVYYCARWQD YDVYFDYWGQGTT |
| 32 | EVQLVESGGGLVQPGGSLRLSCAASGYSFTGYTMNWVRQAPGKGLEWVAL INPYKGVTTYADSVKGRFTISVDKSKNTAYLQMNSLRAEDTAVYYCARSGY YGDSDWYFDVWGQGTLVTVSS |
| 33 | QVQLQQSGAELARPGASVKMSCKASGYTFISYTMHWVKQRPGQGLEWIGI NPRSGYTHYNQKLKDKATLTADKSSSSAYMQLSSLTSEDSAVYYCARSAYY DYDGFAYWGQGTLVTVSA |
| 34 | DIQMTQSPSSLSASVGDRVTITCSASSSVSYMNWYQQTPGKAPKRWIYDTSK LASGVPSRFSGSGSGTDYTFTISSLQPEDIATYYCQQWSSNPFTFGQGTKLQIT |
| 35 | QIVLTQSPAIMSASPGEKVTMTCSASSSVSYMNWYQQKSGTSPKRWIYDTSK LASGVPAHFRGSGSGTSYSLTISGMEAEDAATYYCQQWSSNPFTFGSGTKLE IN |
| 36 | DIQMTQSPSSLSASVGDRVTITCRASQSVSYMNWYQQKPGKAPKRWIYDTS KVASGVPARFSGSGSGTDYSLTINSLEAEDAATYYCQQWSSNPLTFGGGTKV IEIK |
| 37 | DIQLTQSPSILSASVGDRVTITCRASSSVSYMNWYQQKPGKAPKRWIYDTSK VASGVPYRFSGSGSGTEYTLTISSMQPEDFATYYCQQWSSNPLTFGCGTKVEI KRT |
| 38 | EIVLTQSPATLSLSPGERATLSCRASQSVSSYLAWYQQKPGQAPRLLIYDASN RATGIPARFSGSGSGTDFTLTISSLEPEDFAVYYCQQRSNWPPLTFGGGTKVEI K |
| 39 | QIVLSQSPALLSASPGEKVTMTCRASSSYMHWYQQKPGSSPKPWIYATSNLA SGVPARFSGSGSGTSYSLTISRVEAEDAATYYCQQWSSNPPTFGGGTKLETK |

TABLE 1-continued

Amino Acid Sequences

| SEQ ID | Sequence |
|---|---|
| 40 | DIQMTQSPSSLSASVGDRVTITCRASQDIRNYLNWYQQKPGKAPKLLIYYTS RLESGVPSRFSGSGSGTDYTLTISSLQPEDFATYYCQQGNTLPWTFGQGTKV EIK |
| 41 | QIVLTQSPAIMSASPGEKVTMTCSASSSVSYMNWYKQKSGTSPKRWTYDTS KLASGVPARFSGSGSGTSYSLTISSMEAEDAATYYCQQWSSNPPTFGSGTKL EIK |
| 42 | EVQLQQSGPDLVKPGASVKISCKASGYSFTGYYMHWVKQSPGKGLEWIGRI NPNNGVTLYNQKFKDKATLTVDKSSTTAYMELRSLTSEDSAVYYCARSTMI TNYVMDYWGQGTSVTVSSASGGGGSGGGGSGGGGSAGASIVMTQTPTSLL VSAGDRVTITCKASQSVSNDVAWYQQKPGQSPKLLISYTSSRYAGVPDRFSG SGYGTDFTLTISSVQAEDAAVYFCQQDYNSPPTFGGGTKLEIK |
| 43 | QVQLVQSGAEVKKPGASVKVSCKASGYSFTGYYMHWVKQSPGQGLEWIGRI NPNNGVTLYNQKFKDRVTMTRDTSISTAYMELSRLRSDDTAVYYCARSTMI TNYVMDYWGQGTLVTVSSASGGGGSGGGGSGGGGSAGDIVMTQSPDSLAV SLGERATINCKASQSVSNDVAWYQQKPGQPPKLLIYYTSSRYAGVPDRFSGS GSGTDFTLTISSLQAEDVAVYYCQQDYNSPPTFGGGTKLEIK |
| 44 | QVQLVQSGAEVKKPGASVKVSCKASGYSFTSYYMHWVKQSPGQCLEWIGR NPNNGVTLYNQKFKDRVTMTRDTSISTAYMELSRLRSDDTAVYYCARSTMI TNYVMDYWGQGTLVTVSSASGGGGSGGGGSGGGGSAGDIVMTQSPDSLAV SLGERATINCKASQSVSNDVAWYQQKPGQPPKLLIYYTSSRYAGVPDRFSGS GSGTDFTLTISSLQAEDVAVYYCQQDYNSPPTFGCTKLEIK |
| 45 | QVQLQQSGAELARPGASVKMSCKASGYTFTRYTMHWVKQRPGQGLEWIG YINPSRGYTNYNQKFKDKATLTTDKSSSTAYMQLSSLTSEDSAVYYCARYY DDHYCLDYWGQGTTLTVSSASGGGGSGGGGSGGGGSAGQIVLTQSPAIMSA SPGEKVTMTCSASSSVSYMNWYQQKSGTSPKRWIYDTSKLASGVPAHFRGS GSGTSYSLTISGMEAEDAATYYCQQWSSNPFTFGSGTKLEIN |
| 46 | QVQLVQSGAELKKPGASVKVSCKASGYTFTRYTMHWVRQAPGQGLEWMG YINPSRGYTNYNQKFKDKATLTADKSTSTAYMELRSLRSDDTAVYYCARYY DDHYSLDYWGQGTLVTVSSASGGGGSGGGGSGGGGSAGDIQLTQSPSILSA SVGDRVTITCRASSSVSYMNWYQQKPGKAPKRWIYDTSKVASGVPYRFSGS GSGTEYTLTISSMQPEDFATYYCQQWSSNPLTFGGGTKVEIK |
| 47 | QVQLVQSGAELKKPGASVKVSCKASGYTFTRYTMHWVRQAPGQCLEWMG YINPSRGYTNYNQKFKDKATLTADKSTSTAYMELRSLRSDDTAVYYCARYY DDHYSLDYWGQGTLVTVSSASGGGGSGGGGSGGGGSAGDIQLTQSPSILSA SVGDRVTITCRASSSVSYMNWYQQKPGKAPKRWIYDTSKVASGVPYRFSGS GSGTEYTLTISSMQPEDFATYYCQQWSSNPLTFGCGTKVEIK |
| 48 | EVQLVESGGGLVQPGGSLRLSCAASGYSFTGYTMNWVRQAPGKCLEWVAL NPYKGVTTYADSVKGRFTISVDKSKNTAYLQMNSLRAEDTAVYYCARSGY YGDSDWYFDVWGQGTLVTVSSASGGGGSGGGGSGGGGSAGDIQMTQSPSS LSASVGDRVTITCRASQDIRNYLNWYQQKPGKAPKLLIYYTSRLESGVPSRFS GSGSGTDYTLTISSLQPEDFATYYCQQGNTLPWTFGCGTKVEIK |
| 49 | EVQLQQSGPDLVKPGASVKISCKASGYSFTGYYMHWVKQSPGKGLEWIGRI NPNNGVTLYNQKFKDKATLTVDKSSTTAYMELRSLTSEDSAVYYCARSTMI NYVMDYWGQGTSVTVSSASTKGPSVFPLAPSSKSTSGGTAALGCLVKDYF PEPVTVSWNSGALTSGVHTFPAVLQSSGLYSLSSVVTVPSSSLGTQTYICNVN HKPSNTKVDKKVEPKSCDKTHTGPGGGSPGQVQLVQSGAELKKPGASVKVS CKASGYTFTRYTMHWVRQAPGQCLEWMGYINPSRGYTNYNQKFKDKATL TADKSTSTAYMELRSLRSDDTAVYYCARYYDDHYSLDYWGQGTLVTVSSA SGGGGSGGGGSGGGGSAGDIQLTQSPSILSASVGDRVTITCRASSSVSYMNW YQQKPGKAPKRWIYDTSKVASGVPYRFSGSGSGTEYTLTISSMQPEDFATYY CQQWSSNPLTFGCGTKVEIK |
| 50 | SIVMTQTPTSLLVSAGDRVTITCKASQSVSNDVAWYQQKPGQSPKLLISYTSS RYAGVPDRFSGSGYGTDFTLTISSVQAEDAAVYFCQQDYNSPPTFGGGTKLE IKRTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKSF NRGECGPGGGSPGEVQLVQSGPDDVKPGGSVKISCKASGYSFTGYYMHWV KQSPGKCLEWIGRINPNNGVTLYNQKFKDKATLTVDKSSTTAYMELRSLTSE DSAVYYCARSTMITNYVMDYWGQGTLVTVSSASGGGGSGGGGSGGGGSA GDIVMTQTPTSLLVSAGDRVTITCKASQSVSNDVAWYQQKPGQSPKLLISYT SSRYAGVPDRFSGSGYGTDFTLTISSVQAEDAAVYFCQQDYNSPPTFGCGTK LEIKSG |
| 51 | QVQLVQSGAEVKKPGASVKVSCKASGYSFTSYYMHWVKQSPGQGLEWIGR INPNNGVTLYNQKFKDRVTMTRDTSISTAYMELSRLRSDDTAVYYCARSTMI |

TABLE 1-continued

Amino Acid Sequences

| SEQ ID | Sequence |
|---|---|
| | TNYVMDYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICNVN HKPSNTKVDKKVEPKSCDKTHTGPGGGSPGQVQLVQSGAELKKPGASVKVS CKASGYTFTRYTMHWVRQAPGQCLEWMGYINPSRGYTNYNQKFKDKATL TADKSTSTAYMELRSLRSDDTAVYYCARYYDDHYSLDYWGQGTLVTVSSA SGGGGSGGGGSGGGGSAGDIQLTQSPSILSASVGDRVTITCRASSSVSYMNW YQQKPGKAPKRWIYDTSKVASGVPYRFSGSGSGTEYTLTISSMQPEDFATYY CQQWSSNPLTFGCGTKVEIKSG |
| 52 | DIVMTQSPDSLAVSLGERATINCKASQSVSNDVAWYQQKPGQPPKLLIYYTS SRYAGVPDRFSGSGSGTDFTLTISSLQAEDVAVYYCQQDYNSPPTFGGGTKL EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGECGPGGGSPGQVQLVQSGAEVKKPGASVKVSCKASGYSFTSYYMHW VKQSPGQCLEWIGRINPNNGVTLYNQKFKDRVTMTRDTSISTAYMELSRLRS DDTAVYYCARSTMITNYVMDYWGQGTLVTVSSASGGGGSGGGGSGGGGS AGDIVMTQSPDSLAVSLGERATINCKASQSVSNDVAWYQQKPGQPPKLLIY YTSSRYAGVPDRFSGSGSGTDFTLTISSLQAEDVAVYYCQQDYNSPPTFGCG TKLEIKSG |

The invention claimed is:

1. A heterodimer of fusion proteins comprising two different chains, wherein (i) one chain comprises two VH antibody binding domains, one VL antibody binding domain and one CH1 or CL antibody domain, and (ii) the other chain comprises two VL antibody binding domains, one VH antibody binding domain and one CL or CH1 antibody domain, provided that the fusion protein contains one heterodimer interaction between the CH1 antibody domain of one chain and the CL antibody domain of the other chain, characterized in that (a) two combined VH/VL binding domains formed within said heterodimer of fusion proteins are capable of binding to the extracellular 5T4 antigen; and (b) the remaining one combined VH/VL binding domain formed within said heterodimer of fusion proteins is capable of binding to the CD3 receptor complex on T cells, wherein one chain has at least 90% identity with SEQ ID NO: 51 and comprises the following CDR sequences:
SYYMH (SEQ ID NO: 53),
RINPNNGVTLYNQKFKD (SEQ ID NO: 54),
STMITNYVMDY (SEQ ID NO: 55),
SGYTFTRYTMH (SEQ ID NO: 56),
YINPSRGYTNYNQKFKD (SEQ ID NO: 57),
YYDDHYSL (SEQ ID NO: 58),
RASSSVSYMN (SEQ ID NO: 59),
DTSKVAS (SEQ ID NO: 60), and
QQWSSNPL (SEQ ID NO: 61),
and the other chain has at least 90% identity with SEQ ID NO: 52 and comprises the following CDR sequences:
KASQSVSNDVA (SEQ ID NO: 62),
YTSSRYA (SEQ ID NO: 63),
QQDYNSPPT (SEQ ID NO: 64),
SYYMH (SEQ ID NO: 53),
RINPNNGVTLYNQKFKD (SEQ ID NO: 54), and
STMITNYVMDY (SEQ ID NO: 55).

2. A heterodimer of fusion proteins fusion protein according to claim 1, wherein one chain comprises at least 95% identity with SEQ ID NO: 51 and the other chain comprises at least 95% identity with SEQ ID NO: 52.

3. A heterodimer of fusion proteins according to claim 1, wherein one chain comprises SEQ ID NO: 51 and the other chain comprises SEQ ID NO: 52.

4. A pharmaceutical composition comprising a heterodimer of fusion proteins according to claim 1.

5. A kit comprising a heterodimer of fusion proteins as defined in claim 1.

6. A nucleic acid sequence encoding a heterodimer of fusion proteins as defined in claim 1.

7. A process for the production of a heterodimer of fusion proteins, said process comprising culturing a host cell comprising the nucleic acid of claim 6 under conditions allowing the expression of the heterodimer of fusion proteins and recovering the produced heterodimer of fusion proteins from the culture.

* * * * *